United States Patent
Riether et al.

(10) Patent No.: US 10,738,031 B2
(45) Date of Patent: Aug. 11, 2020

(54) N-[(HETEROARYLOXY)PROPANYL] HETEROARYL CARBOXAMIDES AS ANTAGONISTS OF OREXIN SUBTYPE 1 RECEPTOR ACTIVITY

(71) Applicant: Boehringer Ingelheim International GmbH, Ingelheim am Rhein (DE)

(72) Inventors: Doris Riether, Biberach an der Riss (DE); Marco Ferrara, San Donato Milanese (IT); Niklas Heine, Bierach an der Riss (DE); Uta Lessel, Maselheim (DE); Janet Rachel Nicholson, Oberhoefen (DE); Anton Pekcec, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/090,632

(22) PCT Filed: Apr. 7, 2017

(86) PCT No.: PCT/EP2017/058321
§ 371 (c)(1),
(2) Date: Oct. 2, 2018

(87) PCT Pub. No.: WO2017/178344
PCT Pub. Date: Oct. 19, 2017

(65) Prior Publication Data
US 2019/0112292 A1   Apr. 18, 2019

(30) Foreign Application Priority Data
Apr. 15, 2016   (EP) .................................. 16165535

(51) Int. Cl.
| | | |
|---|---|---|
| *A61K 31/16* | (2006.01) | |
| *C07C 233/57* | (2006.01) | |
| *C07D 401/14* | (2006.01) | |
| *C07D 403/12* | (2006.01) | |
| *C07D 413/14* | (2006.01) | |
| *C07D 401/12* | (2006.01) | |
| *C07D 239/34* | (2006.01) | |
| *C07D 213/81* | (2006.01) | |

(52) U.S. Cl.
CPC ......... *C07D 401/14* (2013.01); *C07D 213/81* (2013.01); *C07D 239/34* (2013.01); *C07D 401/12* (2013.01); *C07D 403/12* (2013.01); *C07D 413/14* (2013.01)

(58) Field of Classification Search
CPC .............................. A61K 31/16; C07C 233/57
USPC ........................................... 514/613; 564/123
See application file for complete search history.

(56) References Cited

U.S. PATENT DOCUMENTS

| | | | |
|---|---|---|---|
| 7,468,367 B2 | 12/2008 | Coulton | |
| 9,884,854 B2 | 2/2018 | Riether | |
| 2015/0166523 A1 | 6/2015 | Araki et al. | |
| 2019/0112291 A1 | 4/2019 | Riether | |
| 2019/0112295 A1 | 4/2019 | Riether | |

FOREIGN PATENT DOCUMENTS

| | | |
|---|---|---|
| EP | 2862855 A1 | 4/2015 |
| WO | 03051872 A1 | 6/2003 |
| WO | 2009011775 A1 | 1/2009 |
| WO | 2014091876 A1 | 6/2014 |
| WO | 2015152367 A1 | 10/2015 |
| WO | 2016034882 A1 | 3/2016 |
| WO | 2017178338 A1 | 10/2017 |
| WO | 2017178339 A1 | 10/2017 |
| WO | 2017178340 A1 | 10/2017 |
| WO | 2017178343 A1 | 10/2017 |
| WO | 2017178344 A1 | 10/2017 |
| WO | WO 17/178344 | * 10/2017 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/EP2017/058312 dated 5/2412017.
Written Search Report for PCT/EP2017/058312 dated May 4, 2017.
Suzuki, Discovery and invitro and in vivo profiles of N-ethyl-N-[2-[3-(5-fluoro-2-pyridinyl-)-1H-pyrazol-1-yl-ethyl]-2-(2H-1,2,3-triazol-2-yl)-benzamide asa novel class of dual orexin receptor antagonist, Bioorganic and Medicinal Chemistry, 2014.
International Search Report for PCT/EP2017/058314, dated May 19, 2017.
Written Opinion of the Internation Search Authority for PCT/EP2017/058314 dated May 19, 2017.
International Search Report for PCT/EP2017/058315 dated May 9, 2017.
International Search Report and Written Opinion for PCT/EP2017/058320 dated May 24, 2017.
International report on Patentability for PCT/EP2017/058314, dated Nov. 2, 2018.
English abstract for WO2014091876 cited herein.
English abstract for WO20151522367 cited herein.
International Search Report on Patentability for PCT/EP2017/058321, dated Nov. 5, 2018.

(Continued)

*Primary Examiner* — Douglas M Willis
(74) *Attorney, Agent, or Firm* — Robert J. Kajubi

(57) ABSTRACT

This invention relates to compounds of formula (I), a process for their preparation, pharmaceutical compositions containing them and their use in the treatment of conditions having an association with the orexin sub-type 1 receptor. $Ar^1$ and $Ar^2$ have meanings given in the description.

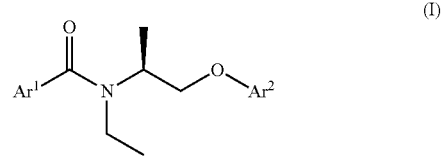

(I)

9 Claims, No Drawings

(56) References Cited

OTHER PUBLICATIONS

Scammell, Annu. Rev. Pharmal. Orexin Receptors, 2011.
Blouin, Nature Communications, Huma hypocretin and melanin concentrating hormone levels are linked to emotion, 2012.
Piccoli, Role of Orexin-1 receptor Mechanisms on Compulsive Food Consumption in a model of binge eating on female rats, Neuropsychopharmacology, vol. 37, 2012.

* cited by examiner

N-[(HETEROARYLOXY)PROPANYL] HETEROARYL CARBOXAMIDES AS ANTAGONISTS OF OREXIN SUBTYPE 1 RECEPTOR ACTIVITY

FIELD OF THE INVENTION

The present invention relates to N-[(heteroaryloxy)propanyl]heteroaryl carboxamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep—wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more).

Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8): e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders such as borderline personality disorder, eating disorders such as binge eating disorder, or attention deficit hyperactivity disorder. Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-ethyl-N-[(2S)-1-(heteroaryloxy)propan-2-yl]pyridine, pyrazine and pyrimidine carboxamide derivatives of formula I

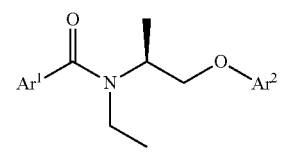

in which

Ar¹ represents

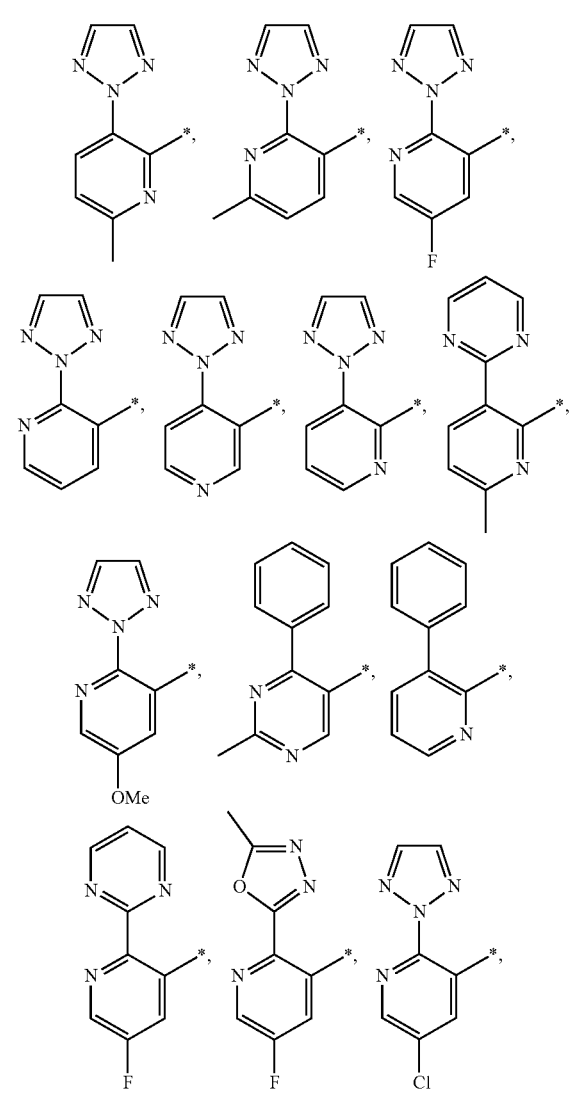

-continued

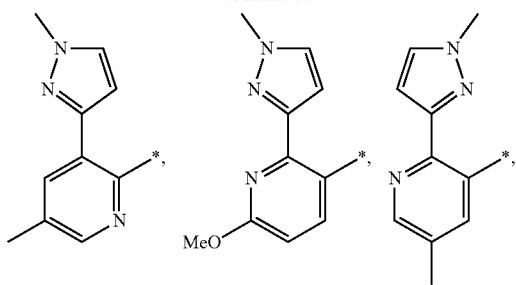

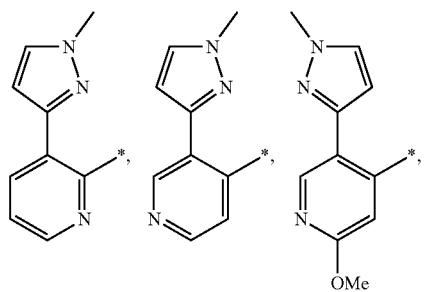

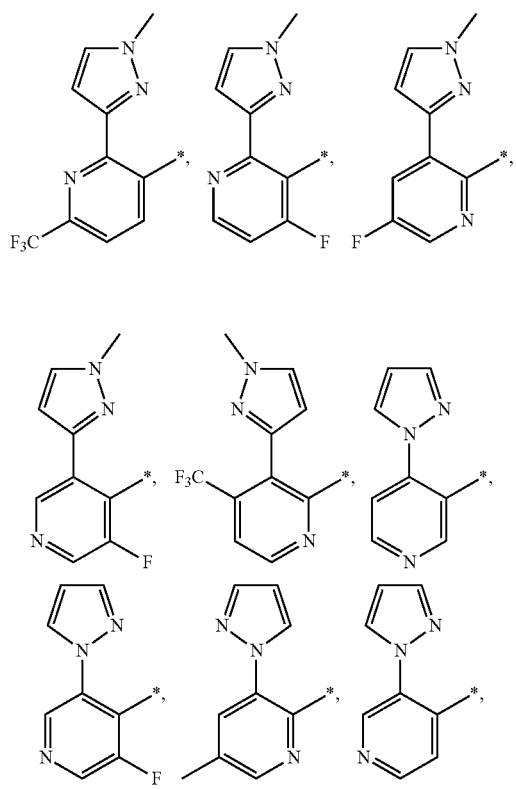

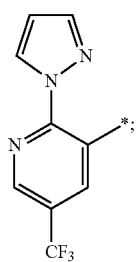

$Ar^2$ represents

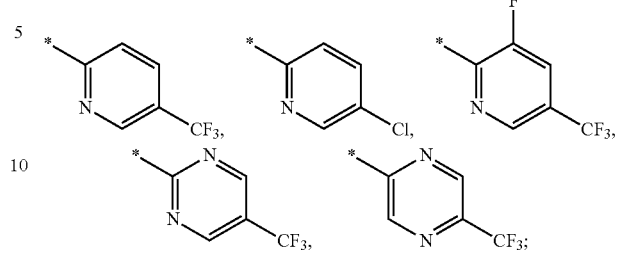

or a salt thereof, particularly a physiologically acceptable salt thereof.

In another embodiment, in the general formula I, $Ar^2$ has the same meaning as defined in the preceding embodiment, and
$Ar^1$ represents

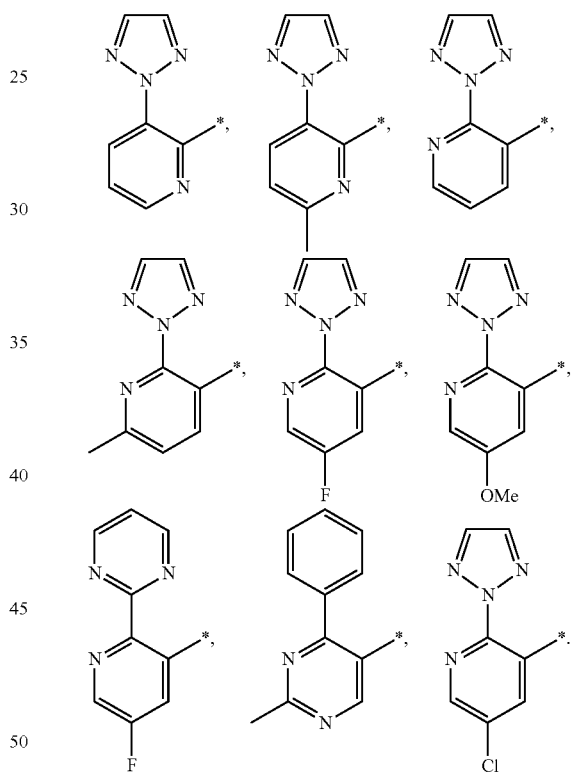

In another embodiment, in the general formula I, $Ar^1$ has the same meaning as defined in the preceding embodiment, and
$Ar^2$ represents

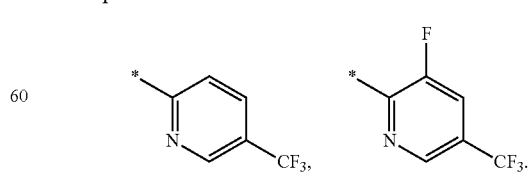

In another embodiment, in the general formula I, $Ar^2$ has the same meaning as defined in the preceding embodiment, and Ar[1] represents

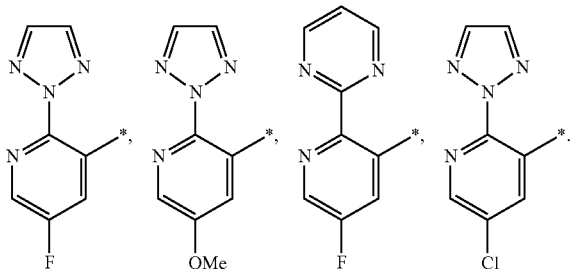

Compounds of the present invention are potent OX1R antagonists. They are more selective over the OX2R than preferred examples disclosed in WO2013/187466. Compounds of the present invention differ structurally from those disclosed in WO2013/187466 in that they contain a substituted —O-pyrimidyl, —O-pyrazinyl or —O-pyridinyl moiety in place of a Het1-Het2 moiety in which Het2 is phenyl or pyridyl. These structural differences unexpectedly result in an explicit enhancement in selectivity over the OX2R.

Compounds of the present invention differ structurally from Example 73, 46, 84, 47, 70, and 71 in WO2016/034882 (closest prior art) in that they contain a central N-ethyl-(propan-2-yl)amino moiety in place of the N-methyl- or N-ethyl-[butan-2-yl]amino moiety, and contain a —O-pyrimidyl, —O-pyrazinyl or —O-pyridinyl moiety in place of a —N-pyrimidyl, —N-pyrazinyl or —N— pyridinyl moiety. The structural differences unexpectedly result in superior pharmacokinetic properties demonstrated by improved stability in human liver microsomes. Therefore, compounds of the present invention are expected to have a medium to low in vivo clearance and thus a longer duration of action and better tolerability due to the lager window between efficacy and undesired effects such as drowsiness and sleep. Consequently, compounds of the present invention must be more viable for human use.

General Definitions

Terms not specifically defined herein should be given the meanings that would be given to them by one skilled in the art in light of the disclosure and the context.
Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.
Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays

Abbreviations
IP1 D-myo-Inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:
A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOX1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 10000 cells/25 µL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM and/or 50 nM) dissolved in assay buffer is added to the assay plate. The assay plate is incubated for 60 minutes at 37° C. Then 5 µL per well of Anti-IP1-Cryptate Tb solution and 5 µL per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOX2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 µL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay. On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM) dissolved in assay buffer is added to the assay plate. The assay plate is incubated for 60 minutes at 37° C. Then 5 µL per well of Anti-IP1-Cryptate Tb solution and 5 µL per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

Biological Data

Comparison of Assays A and B with the Assays Described in WO2013/187466

Assays described in WO2013/187466 differ from assays A and B in:

The technology and readout: fluorescence measurement of intracellular $Ca^{2+}$ changes (WO2013/187466) instead of luminescence measurement of IP1 (assays A and B)

OX1R and OX2R overexpressing cell lines used for the assays described in WO 2013/187466 are of different origin as cell lines used for assays A and B Use of modified orexin A (2 amino acids substituted) as agonist instead of orexin A Agonist concentration of 300 pM used for the OX1R assay and 3 nM for the OX2R assay (EC75 vs. EC100; according to Okumura T. et al., Biochemical and Biophysical Research Communications, 2001) (WO2013/187466). $IC_{50}$ values that have been reported are dependent on the agonist concentration. Selectivity ratios calculated from these $IC_{50}$ values cannot be compared with the selectivity ratios calculated from the agonist concentration independent Kb values obtained from assay A and B.

Due to these differences between the assays, a direct comparison has to be established. Therefore, examples 69, 70 (the most selective ones) and 5 (one of the most potent ones) described in WO 2013/187466 are tested in assays A and B so as to be directly compared with compounds of the present invention (see Table 1).

TABLE 1
In vitro potencies of compounds of WO2013/187466 as reported therein versus as determined in the Assays A and B (described above)
| Structure Example # in WO2013/187466 | As described in WO2013/187466 | | | As determined in Assays A and B | | |
|---|---|---|---|---|---|---|
| | OX1R IC$_{50}$ [nM] | OX2R IC$_{50}$ [nM] | OX2R IC$_{50}$/ OX1R IC$_{50}$ | OX1R Kb [nM] (Orexin A concentration used) | OX2R Kb [nM] (0.5 nM Orexin A concentration) | OX2R Kb/ OX1R Kb |
| 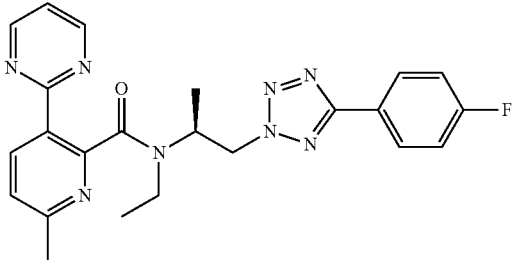 [SMILES: CCN(C(=O)c1nc(C)ccc1-c1ncccn1)[C@@H](C)Cn1nnc(-c2ccc(F)cc2)n1]  Example 69 | 1.6 | 1896 | 1185 | 2.25 (0.5 nM) | 98 | 43 |
| 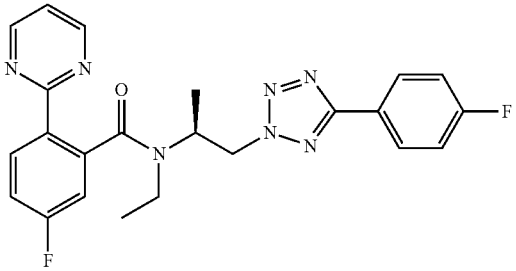 [SMILES: CCN(C(=O)c1cc(F)ccc1-c1ncccn1)[C@@H](C)Cn1nnc(-c2ccc(F)cc2)n1]  Example 70 | 1.1 | 452 | 411 | 0.72 (50 nM) | 29 | 40 |
| 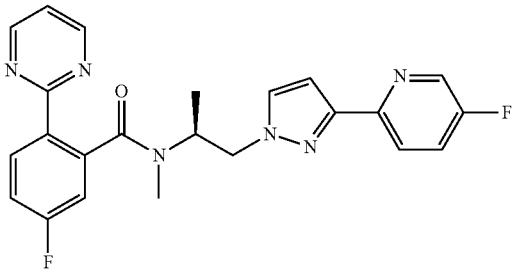 [SMILES: C[C@@H](Cn1ccc(-c2ccc(F)cn2)n1)N(C)C(=O)c1cc(F)ccc1-c1ncccn1]  Example 5 | 0.5 | 76 | 152 | 0.94 (50 nM) | 28 | 30 |

TABLE 2

In vitro potencies of the structurally closest prior art compounds
(Example 73, 46, 84, 47, 70, 71) WO2016/034882 as reported therein:

As described in WO2016/034882 (Table 1, page 178)

| Structure<br>Example # in WO2016/034882 | OX1R | OX2R | OX2R IC$_{50}$/<br>OX1R IC$_{50}$ |
|---|---|---|---|
| Example 73 | Table 1 and 2:<br>not reported<br>Table 3:<br>pIC$_{50}$ = 8.8<br>corresponds to<br>IC$_{50}$ = 1.6 nM | Table 1 and 2:<br>not reported<br>Table 3:<br>pIC$_{50}$ < 6.0<br>corresponds to<br>IC$_{50}$ > 1000 nM | Table 3:<br>>625 |
| Example 46 | Table 1:<br>pIC$_{50}$ = 7.7<br>corresponds to<br>IC$_{50}$ = 20 nM<br>Table 2:<br>pIC$_{50}$ = 7.5<br>corresponds to<br>IC$_{50}$ = 32 nM<br>Table 3:<br>pIC$_{50}$ = 8.5<br>corresponds to<br>IC$_{50}$ = 3.2 nM | Table 1:<br>pIC$_{50}$ = 5.1<br>corresponds to<br>IC$_{50}$ = 7800 nM<br>Table 2:<br>pIC$_{50}$ < 5.0<br>corresponds to<br>IC$_{50}$ > 10000 nM<br>Table 3:<br>pIC$_{50}$ < 5.0<br>corresponds to<br>IC$_{50}$ = 10000 nM | Table 1:<br>390<br>Table 2:<br>>312<br>Table 3:<br>3200 |
| Example 84 | Table 1 and 2:<br>not reported<br>Table 3:<br>pIC$_{50}$ = 8.7<br>corresponds to<br>IC$_{50}$ = 1.9 nM | Table 1 and 2:<br>not reported<br>Table 3:<br>pIC$_{50}$ = 6.0<br>corresponds to<br>IC$_{50}$ = 1000 nM | Table 3:<br>526 |
| Example 47 | Table 1:<br>pIC$_{50}$ = 7.5<br>corresponds to<br>IC$_{50}$ = 32 nM<br>Table 2:<br>pIC$_{50}$ = 8.4<br>corresponds to<br>IC$_{50}$ = 3.9 nM<br>Table 3:<br>pIC$_{50}$ = 8.6<br>corresponds to<br>IC$_{50}$ = 2.5 nM | Table 1:<br>pIC$_{50}$ = 5.2<br>corresponds to<br>IC$_{50}$ = 6300 nM<br>Table 2:<br>pIC$_{50}$ < 5.1<br>corresponds to<br>IC$_{50}$ > 7900 nM<br>Table 3:<br>pIC$_{50}$ < 5.4<br>corresponds to<br>IC$_{50}$ > 3950 nM | Table 1:<br>197<br>Table 2:<br>>2026<br>Table 3:<br>>1580 |

TABLE 2-continued

In vitro potencies of the structurally closest prior art compounds
(Example 73, 46, 84, 47, 70, 71) WO2016/034882 as reported therein:

As described in WO2016/034882 (Table 1, page 178)

| Structure<br>Example # in WO2016/034882 | OX1R | OX2R | OX2R IC$_{50}$/<br>OX1R IC$_{50}$ |
|---|---|---|---|
| Example 70 | Table 1 and 2:<br>not reported<br>Table 3:<br>pIC$_{50}$ = 8.8<br>corresponds to<br>IC$_{50}$ = 1.6 nM | Table 1 and 2:<br>not reported<br>Table 3:<br>pIC$_{50}$ = 5.3<br>corresponds to<br>IC$_{50}$ > 5000 nM | Table 3:<br>>3125 |
| Example 71 | Table 1 and 2:<br>not reported<br>Table 3:<br>pIC$_{50}$ = 9.0<br>corresponds to<br>IC$_{50}$ = 1 nM | Table 1 and 2:<br>not reported<br>Table 3:<br>pIC$_{50}$ = 6.6<br>corresponds to<br>IC$_{50}$ = 320 nM | Table 3:<br>320 |

Table 3 shows a comparison of biological data on the OX1R and OX2R potencies as well as stability in human liver microsomes of compounds of the present invention with those of the closest prior art compounds in WO 2016/034882. These data demonstrate that compounds of the present invention are more stable in human liver microsomes.

Examples 23 and 30 of the present invention differ structurally from Example 73 and 46 in WO2016/034882, the closest prior art compounds, in that they a) contain a central N-ethyl-(propan-2-yl)amino moiety in place of the N-methyl- or N-ethyl-[butan-2-yl]amino moiety and b) contain a —O-pyrimidyl moiety instead of the —N-pyrimidyl substituent. Example 30 differs structurally farther from Example 73 and 46 in WO2016/034882 in that it has the pyridine nitrogen and the methyl substituent in a different position.

Unexpectedly, these structural differences lead to a markedly improved stability in human liver microsomes.

Examples 15 and 11 of the current invention differ structurally from Example 84 in WO2016/034882, the closest prior art compound, in that they a) contain a central N-ethyl-(propan-2-yl)amino moiety in place of the N-methyl-[butan-2-yl]amino moiety and b) contain a —O-pyrimidyl moiety instead of the —N-pyrimidyl substituent. Example 15 differs structurally further in that it lacks the methyl substituent on the pyridine and the pyridine is substituted with a phenyl instead of a pyrimidyl group. Unexpectedly, these structural differences lead to a markedly improved stability in human liver microsomes.

Example 11 differs structurally further from Example 84 in WO2016/034882 in that it has a pyrimidine instead of the pyridine, which is substituted with a phenyl instead of a pyrimidyl group. Further the methyl substituent is in a different position. Unexpectedly, these structural differences lead to a markedly improved stability in human liver microsomes as well as an increase in OX1R selectivity.

Examples 10, 33, and 9 of the present invention differ structurally from Example 47 and 70 in WO2016/034882, the closest prior art compounds, in that they a) contain a central N-ethyl-(propan-2-yl)amino moiety in place of the N-methyl- or N-ethyl-[butan-2-yl]amino moiety and b) contain a —O-pyrazinyl moiety instead of the —N-pyrazinyl substituent. Example 33 differs structurally farther from Example 47 and 70 in WO2016/034882 in that it has the pyridine nitrogen and the methyl substituent in a different position. Example 9 differs structurally further in that it has a pyrimidine instead of the pyridine, which is substituted with a phenyl instead of a triazoyl group. Further, the methyl substituent is in a different position. Unexpectedly, these structural differences lead to a markedly improved stability in human liver microsomes.

Examples 53 and 45 of the present invention differ structurally from Example 84 in WO2016/034882, the closest prior art compound, in that they a) contain a central N-ethyl-(propan-2-yl)amino moiety in place of the N-methyl-[butan-2-yl]amino moiety and b) contain a —O-pyrazinyl instead of the —N-pyrimidyl moiety. Unexpectedly, the structural differences lead to a markedly improved stability in human liver microsomes of Example 53.

Example 45 differs structurally farther from Example 84 in WO2016/034882 in that it has the pyridine nitrogen in a different position and the pyridine has a fluoro instead of a methyl substituent. Unexpectedly, these structural differences lead to a markedly improved stability in human liver microsomes and to an increase in OX1R selectivity as well as.

Examples 5, 12, 8, 26, 57, 71, 6, 17, 36, 56, 61, 72, 21, 22, 42, 43, 44, 48, 51, 54, 60, 20, 34, 37, 50, 64, 3, 24, 27, 28, 29, 32, 38, 40, 58, 69, and 59 of the present invention differ structurally from Example 71 in WO2016/034882, the closest prior art compound, in that they a) contain a central N-ethyl-(propan-2-yl)amino moiety in place of the N-ethyl-[butan-2-yl]amino moiety and b) contain an —O-pyridyl instead of the —N-pyridyl moiety. Examples 12, 8, 57, 71, 21, 22, 42, 43, 44, 48, 51, 54, and 60 differ structurally farther from Example 71 in WO2016/034882 in that the O-pyridyl is substituted with an additional fluoro-substituent, or a CI-substituent instead of the CF$_3$-group. Examples 26, 57, 71, 6, 17, 36, 56, 61, 72, 21, 22, 42, 43, 44, 48, 51, 54, 60, 20, 34, 37, 50, 64, 3, 24, 27, 28, 29, 32, 38, 40, 58, 69, and 59 differ structurally further from Example 71 in WO2016/034882 in that they lack the methyl substituent on the pyridyl, or have it in a different position, or they have a substituent such as methoxy, fluoro chloro or CF$_3$ instead of the methyl substituent in the same or a different position. In addition, in some instances, the pyridine nitrogen is in a different position. Even further, Examples 20, 34, 37, 50, 64, 3, 24, 27, 28, 29, 32, 38, 40, 58, 69, and 59 have a different 5-membered heteroaryl ring instead of the triazoyl group. These structural differences unexpectedly result in a markedly improved stability in human liver microsomes as compared to Example 71 in WO2016/034882.

Examples 35 and 70 of the present invention differ structurally from Example 84 in WO2016/034882, the closest prior art compound, in that a) they contain a central N-ethyl-(propan-2-yl)amino moiety in place of the N-methyl-[butan-2-yl]amino moiety and contain a —O—pyridyl moiety instead of the —N-pyrimidyl substituent; and b) the pyridine, which is a substituted with fluoro instead of methyl, is a different isomer (nitrogen in a different position). These structural differences unexpectedly result in a markedly improved stability in human liver microsomes, as well as in an increase in OX1R selectivity

TABLE 3

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST t$_{1/2}$ [min] |
|---|---|---|---|---|---|
| Ex 73 in WO2016/ 034882 | 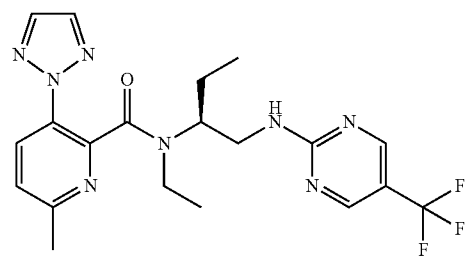 [SMILES: CC[C@@H](CNc1ncc(C(F)(F)F)cn1)N(CC)C(=O)c1nc(C)ccc1-n1nccn1] | 0.309 (50 nM) | 145 | 469 | 11 |
| Ex 46 in WO2016/ 034882 | 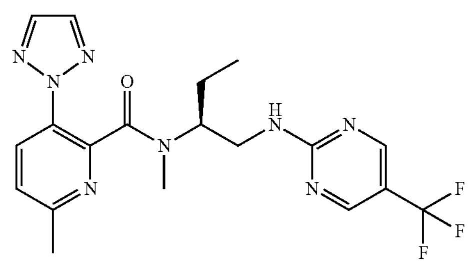 [SMILES: CC[C@@H](CNc1ncc(C(F)(F)F)cn1)N(C)C(=O)c1nc(C)ccc1-n1nccn1] | 1.558 (50 nM) | 372 | 240 | 32 |
| 23 | 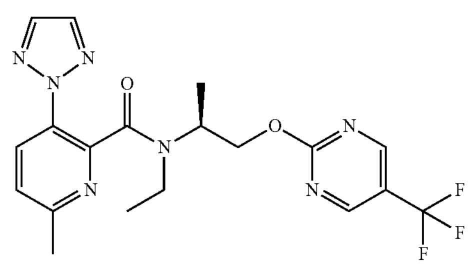 [SMILES: CCN(C(=O)c1nc(C)ccc1-n1nccn1)[C@@H](C)COc1ncc(C(F)(F)F)cn1] | 6.6 (0.5 nM) | 2898 | 439 | 110 |

TABLE 3-continued

*Comparison of biological data of the compounds of the present invention with the closest prior art compounds in WO2016/034882*

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 30 | 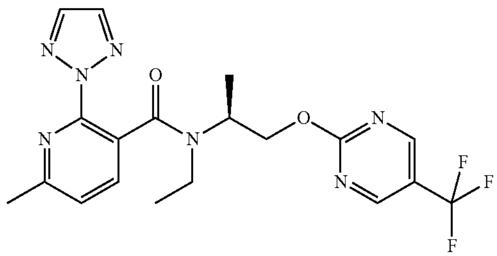 [SMILES: CCN(C(=O)c1ccc(C)nc1-n1nccn1)[C@@H](C)COc1ncc(C(F)(F)F)cn1] | 5.6 (0.5 nM) | 3592 | 641 | >130 |
| Ex 84 in WO2016/ 034882 | 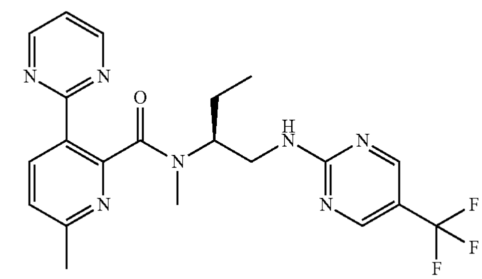 [SMILES: CC[C@@H](CNc1ncc(C(F)(F)F)cn1)N(C)C(=O)c1nc(C)ccc1-c1ncccn1] | 2.20 (0.5 nM) | 229 | 104 | 41 |
| 15 | 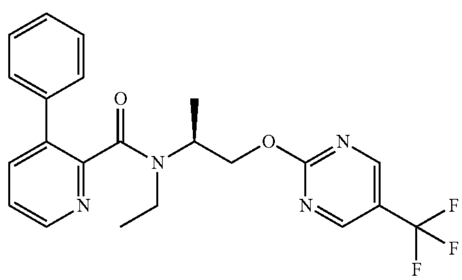 [SMILES: CCN(C(=O)c1ncccc1-c1ccccc1)[C@@H](C)COc1ncc(C(F)(F)F)cn1] | 4.5 (0.5 nM) | 705 | 157 | 96 |
| 11 | 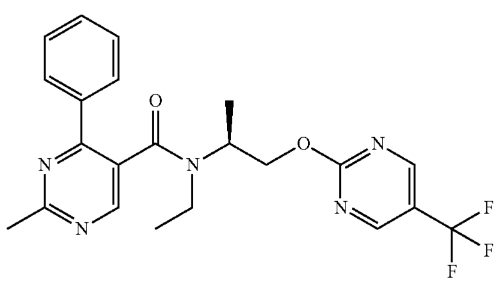 [SMILES: CCN(C(=O)c1cnc(C)nc1-c1ccccc1)[C@@H](C)COc1ncc(C(F)(F)F)cn1] | 1.5 (0.5 nM) | 1290 | 860 | 88 |
| Ex 47 in WO2016/ 034882 | 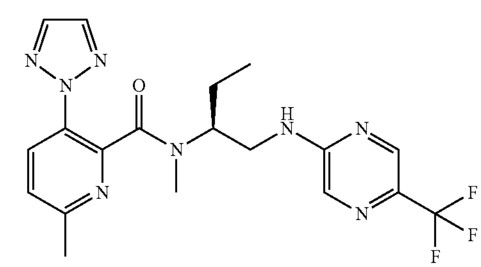 [SMILES: CC[C@@H](CNc1cnc(C(F)(F)F)cn1)N(C)C(=O)c1nc(C)ccc1-n1nccn1] | 0.84 (0.5 nM) 0.53 (50 nM) | 107 | 127 203 | 14 |

TABLE 3-continued

*Comparison of biological data of the compounds of the present invention with the closest prior art compounds in WO2016/034882*

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST t$_{1/2}$ [min] |
|---|---|---|---|---|---|
| Ex 70 in WO2016/ 034882 | 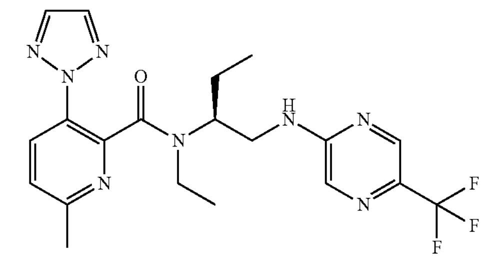 [SMILES: CC[C@@H](CNc1cnc(C(F)(F)F)cn1)N(CC)C(=O)c1nc(C)ccc1-n1nccn1] | 0.135 (50 nM) | 43 | 319 | 20 |
| 10 | 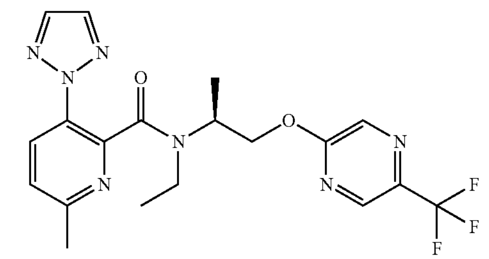 [SMILES: CCN(C(=O)c1nc(C)ccc1-n1nccn1)[C@@H](C)COc1cnc(C(F)(F)F)cn1] | 2.5 (0.5 nM) | 749 | 300 | >130 |
| 33 | 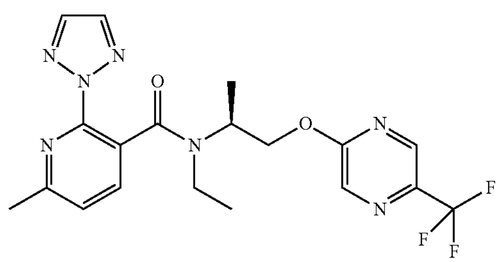 [SMILES: CCN(C(=O)c1ccc(C)nc1-n1nccn1)[C@@H](C)COc1cnc(C(F)(F)F)cn1] | 7.8 (0.5 nM) | 3283 | 421 | >130 |
| 9 | 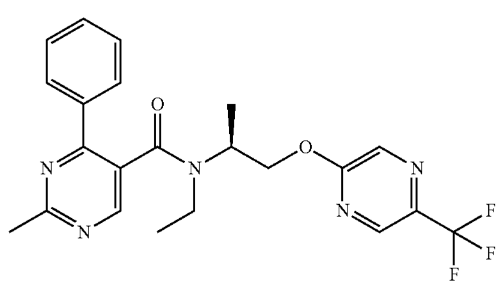 [SMILES: CCN(C(=O)c1cnc(C)nc1-c1ccccc1)[C@@H](C)COc1cnc(C(F)(F)F)cn1] | 1.8 (0.5 nM) | 939 | 522 | >130 |
| Ex 84 in WO2016/ 034882 | 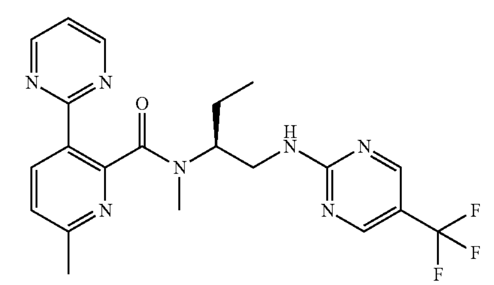 [SMILES: CC[C@@H](CNc1ncc(C(F)(F)F)cn1)N(C)C(=O)c1nc(C)ccc1-c1ncccn1] | 2.20 (0.5 nM) | 229 | 104 | 41 |

TABLE 3-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
| --- | --- | --- | --- | --- | --- |
| 53 | 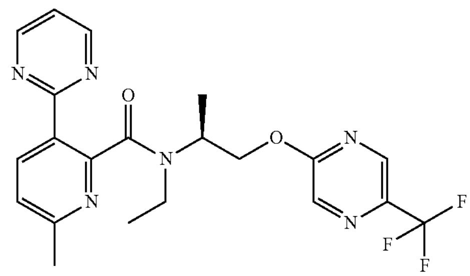 [SMILES: CCN(C(=O)c1nc(C)ccc1-c1ncccn1)[C@@H](C)COc1cnc(C(F)(F)F)cn1] | 3.2 (0.5 nM) | 337 | 105 | >130 |
| 45 | 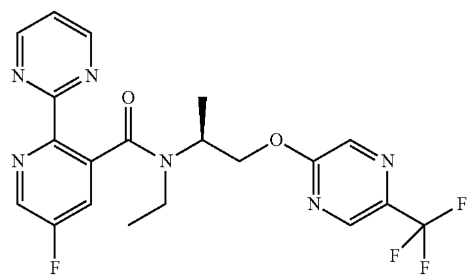 [SMILES: CCN(C(=O)c1cc(F)cnc1-c1ncccn1)[C@@H](C)COc1cnc(C(F)(F)F)cn1] | 20 (0.5 nM) | 6645 | 332 | >130 |
| Ex 71 in WO2016/ 034882 | 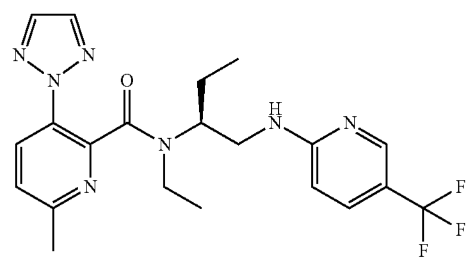 [SMILES: CC[C@@H](CNc1ccc(C(F)(F)F)cn1)N(CC)C(=O)c1nc(C)ccc1-n1nccn1] | 0.030 (50 nM) | 27 | 905 | 4.5 |
| 5 | 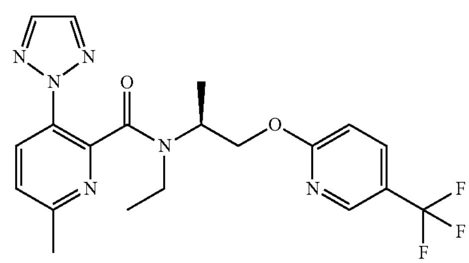 [SMILES: CCN(C(=O)c1nc(C)ccc1-n1nccn1)[C@@H](C)COc1ccc(C(F)(F)F)cn1] | 0.15 (50 nM) | 59 | 393 | 25 |
| 12 | 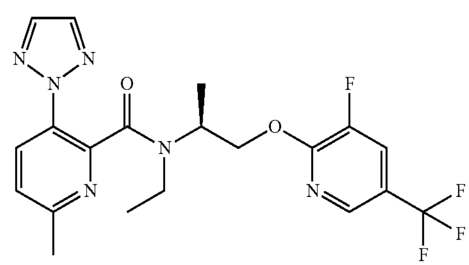 [SMILES: CCN(C(=O)c1nc(C)ccc1-n1nccn1)[C@@H](C)COc1ncc(C(F)(F)F)cc1F] | 0.77 (0.5 nM) | 206 | 268 | 13 |

TABLE 3-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 8 | 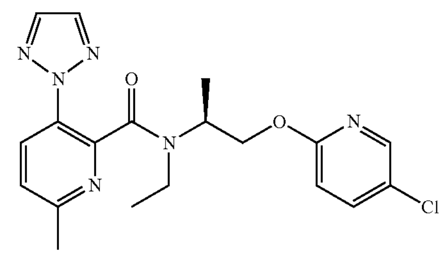 [SMILES: CCN(C(=O)c1nc(C)ccc1-n1nccn1)[C@@H](C)COc1ccc(Cl)cn1] | 0.45 (50 nM) | 71 | 158 | 25 |
| 26 | 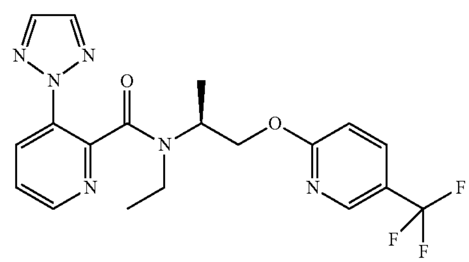 [SMILES: CCN(C(=O)c1ncccc1-n1nccn1)[C@@H](C)COc1ccc(C(F)(F)F)cn1] | 0.95 (0.5 nM) | 267 | 281 | >130 |
| 57 | 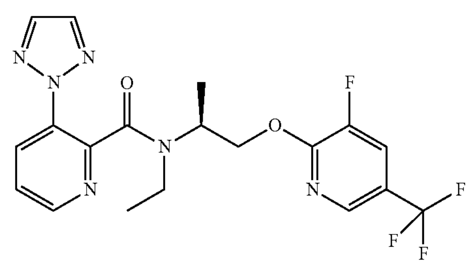 [SMILES: CCN(C(=O)c1ncccc1-n1nccn1)[C@@H](C)COc1ncc(C(F)(F)F)cc1F] | 1.8 (0.5 nM) | 419 | 233 | 56 |
| 71 | 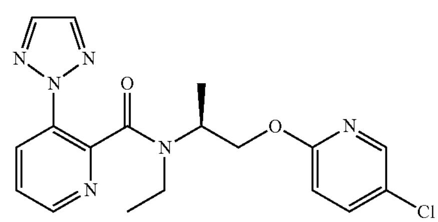 [SMILES: CCN(C(=O)c1ncccc1-n1nccn1)[C@@H](C)COc1ccc(Cl)cn1] | 3.0 (0.5 nM) | 339 | 113 | 63 |
| 6 | 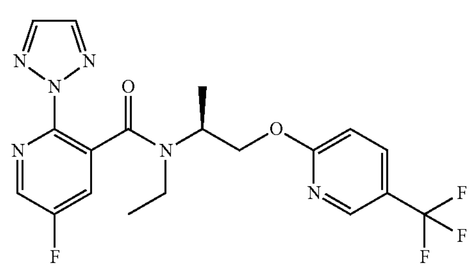 [SMILES: CCN(C(=O)c1cc(F)cnc1-n1nccn1)[C@@H](C)COc1ccc(C(F)(F)F)cn1] | 1.2 (0.5 nM) 1.5 (50 nM) | 844 | 703 563 | >130 |

TABLE 3-continued

Comparison of biological data of the compounds of the present
invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 17 | 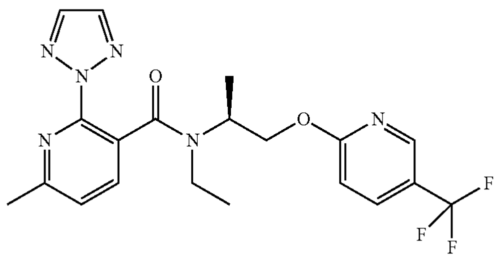 [SMILES: CCN(C(=O)c1ccc(C)nc1-n1nccn1)[C@@H](C)COc1ccc(C(F)(F)F)cn1] | 0.22 (50 nM) | 356 | 1618 | 59 |
| 36 | 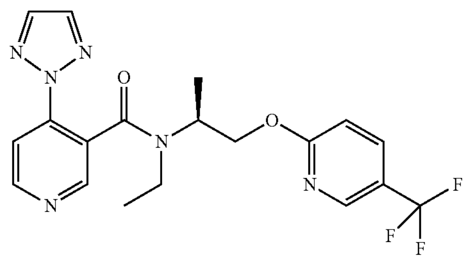 [SMILES: CCN(C(=O)c1cnccc1-n1nccn1)[C@@H](C)COc1ccc(C(F)(F)F)cn1] | 1.0 (0.5 nM) | 240 | 240 | 15 |
| 56 | 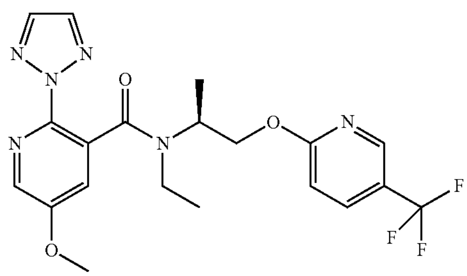 [SMILES: CCN(C(=O)c1cc(OC)cnc1-n1nccn1)[C@@H](C)COc1ccc(C(F)(F)F)cn1] | 0.50 (0.5 nM) 0.49 (50 nM) | 260 | 520 526 | >130 |
| 61 | 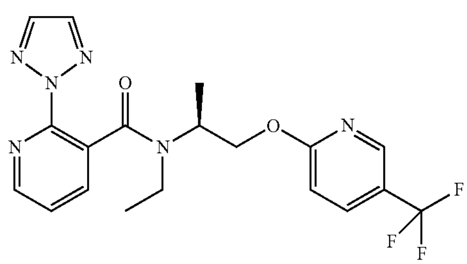 [SMILES: CCN(C(=O)c1cccnc1-n1nccn1)[C@@H](C)COc1ccc(C(F)(F)F)cn1] | 2.31 (0.5 nM) | 678 | 294 | >130 |
| 72 | 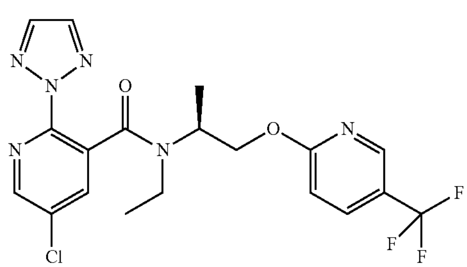 [SMILES: CCN(C(=O)c1cc(Cl)cnc1-n1nccn1)[C@@H](C)COc1ccc(C(F)(F)F)cn1] | 0.37 (0.5 nM) 0.24 (50 nM) | 250 | 675 1041 | >130 |

TABLE 3-continued

*Comparison of biological data of the compounds of the present invention with the closest prior art compounds in WO2016/034882*

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 21 | 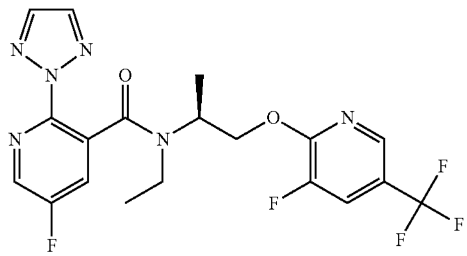 [SMILES: CCN(C(=O)c1cc(F)cnc1-n1nccn1)[C@@H](C)COc1ncc(C(F)(F)F)cc1F] | 3.3 (0.5 nM) | 2696 | 817 | >130 |
| 22 | 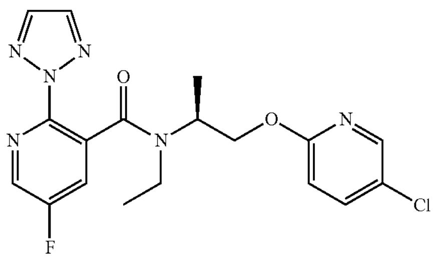 [SMILES: CCN(C(=O)c1cc(F)cnc1-n1nccn1)[C@@H](C)COc1ccc(Cl)cn1] | 4.7 (0.5 nM) | 1009 | 215 | 82 |
| 42 | 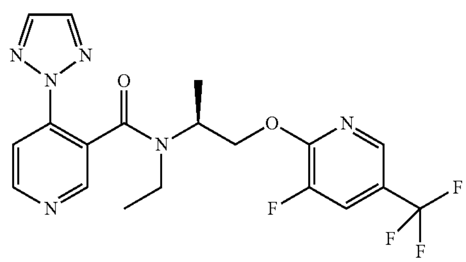 [SMILES: CCN(C(=O)c1cnccc1-n1nccn1)[C@@H](C)COc1ncc(C(F)(F)F)cc1F] | 2.3 (0.5 nM) | 483 | 210 | 13 |
| 43 | 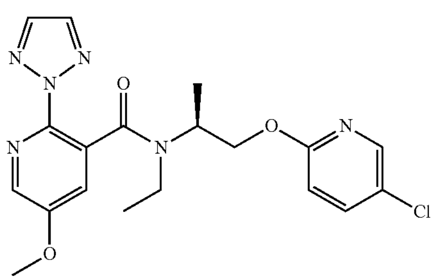 [SMILES: CCN(C(=O)c1cc(OC)cnc1-n1nccn1)[C@@H](C)COc1ccc(Cl)cn1] | 1.9 (0.5 nM) | 325 | 171 | 110 |
| 44 | 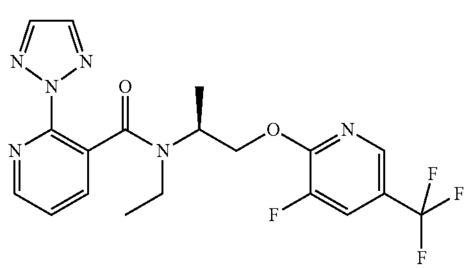 [SMILES: CCN(C(=O)c1cccnc1-n1nccn1)[C@@H](C)COc1ncc(C(F)(F)F)cc1F] | 4.2 (0.5 nM) | 1212 | 289 | >130 |

TABLE 3-continued

Comparison of biological data of the compounds of the present
invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 48 | 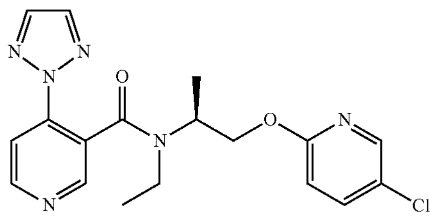 [SMILES: CCN(C(=O)c1cnccc1-n1nccn1)[C@@H](C)COc1ccc(Cl)cn1] | 2.6 (0.5 nM) | 381 | 147 | 33 |
| 51 | 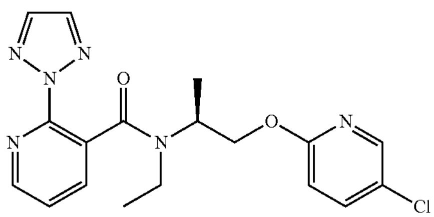 [SMILES: CCN(C(=O)c1cccnc1-n1nccn1)[C@@H](C)COc1ccc(Cl)cn1] | 8.3 (0.5 nM) | 1143 | 138 | >130 |
| 54 | 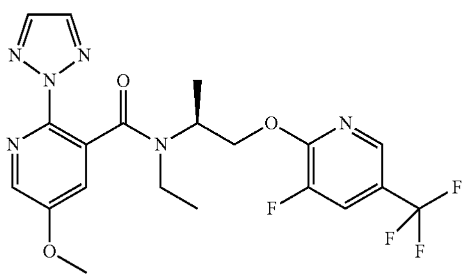 [SMILES: CCN(C(=O)c1cc(OC)cnc1-n1nccn1)[C@@H](C)COc1ncc(C(F)(F)F)cc1F] | 0.89 (0.5 nM) | 578 | 649 | >130 |
| 60 | 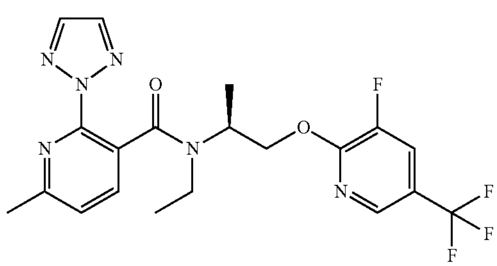 [SMILES: CCN(C(=O)c1ccc(C)nc1-n1nccn1)[C@@H](C)COc1ncc(C(F)(F)F)cc1F] | 0.67 (0.5 nM) 0.66 (50 nM) | 882 | 1316 1347 | >130 |
| 20 | 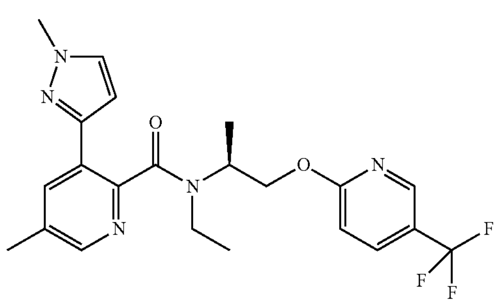 [SMILES: CCN(C(=O)c1ncc(C)cc1-c1ccn(C)n1)[C@@H](C)COc1ccc(C(F)(F)F)cn1] | 0.25 (50 nM) | 415 | 1660 | 24 |

TABLE 3-continued

Comparison of biological data of the compounds of the present
invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 34 | 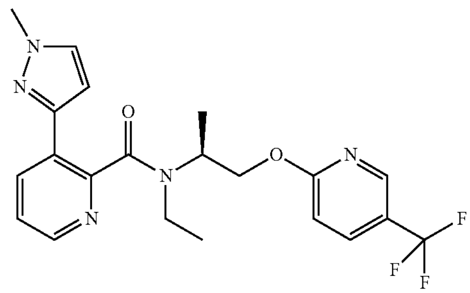 [SMILES: CCN(C(=O)c1ncccc1-c1ccn(C)n1)[C@@H](C)COc1ccc(C(F)(F)F)cn1] | 1.5 (0.5 nM) | 285 | 190 | 81 |
| 37 | 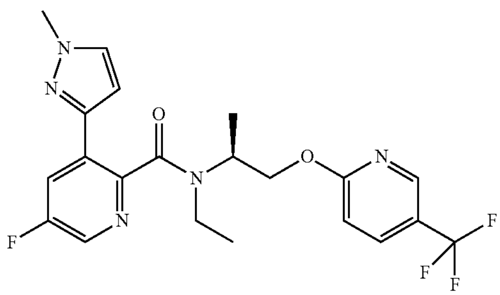 [SMILES: CCN(C(=O)c1ncc(F)cc1-c1ccn(C)n1)[C@@H](C)COc1ccc(C(F)(F)F)cn1] | 3.3 (0.5 nM) | 802 | 243 | 24 |
| 50 | 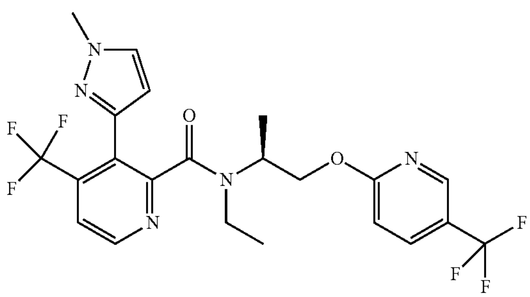 [SMILES: CCN(C(=O)c1nccc(C(F)(F)F)c1-c1ccn(C)n1)[C@@H](C)COc1ccc(C(F)(F)F)cn1] | 0.11 (50 nM) | 26 | 236 | 23 |
| 64 | 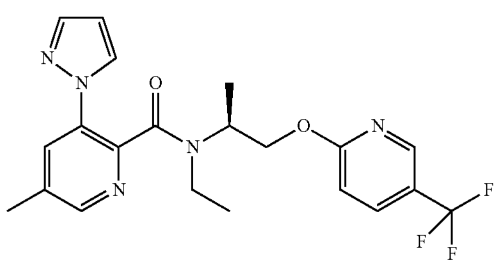 [SMILES: CCN(C(=O)c1ncc(C)cc1-n1cccn1)[C@@H](C)COc1ccc(C(F)(F)F)cn1] | 0.40 (50 nM) | 275 | 688 | 20 |
| 3 | 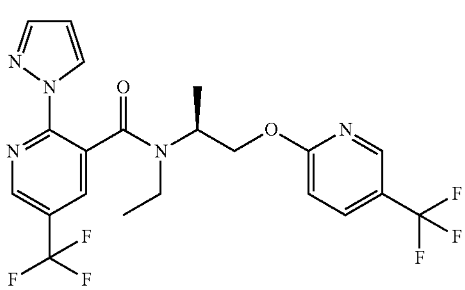 [SMILES: CCN(C(=O)c1cc(C(F)(F)F)cnc1-n1cccn1)[C@@H](C)COc1ccc(C(F)(F)F)cn1] | 1.2 (0.5 nM and 50 nM) | 212 | 177 | 83 |

TABLE 3-continued

Comparison of biological data of the compounds of the present invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 24 | 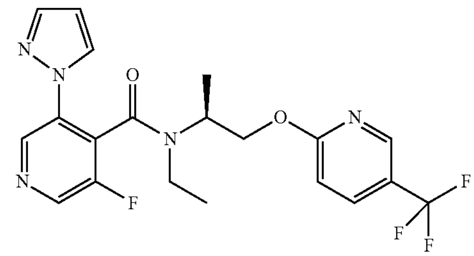 [SMILES: CCN(C(=O)c1c(F)cncc1-n1cccn1)[C@@H](C)COc1ccc(C(F)(F)F)cn1] | 6.4 (0.5 nM) | 1068 | 167 | 29 |
| 27 | 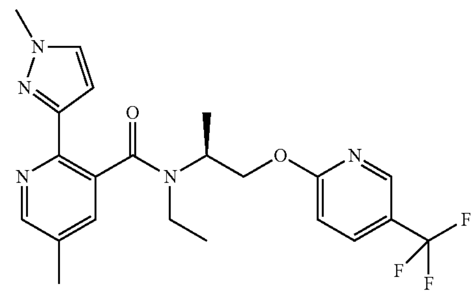 [SMILES: CCN(C(=O)c1cc(C)cnc1-c1ccn(C)n1)[C@@H](C)COc1ccc(C(F)(F)F)cn1] | 0.87 (0.5 nM) 0.69 (50 nM) | 134 | 154 194 | 31 |
| 28 | 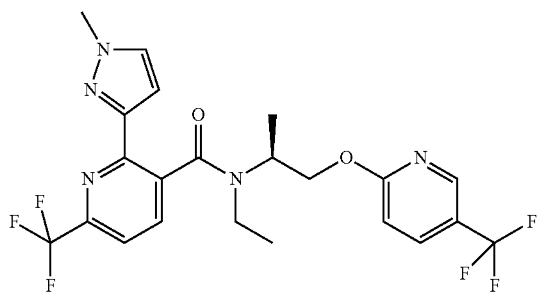 [SMILES: CCN(C(=O)c1ccc(C(F)(F)F)nc1-c1ccn(C)n1)[C@@H](C)COc1ccc(C(F)(F)F)cn1] | 2.0 (0.5 nM) | 705 | 353 | 11 |
| 29 | 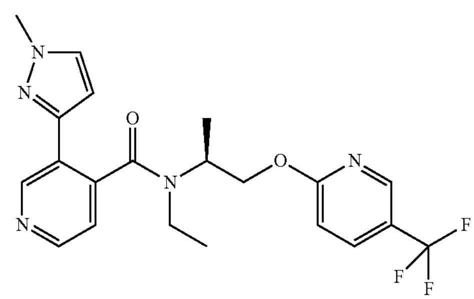 [SMILES: CCN(C(=O)c1ccncc1-c1ccn(C)n1)[C@@H](C)COc1ccc(C(F)(F)F)cn1] | 8.7 (0.5 nM) | 1603 | 184 | 11 |
| 32 | 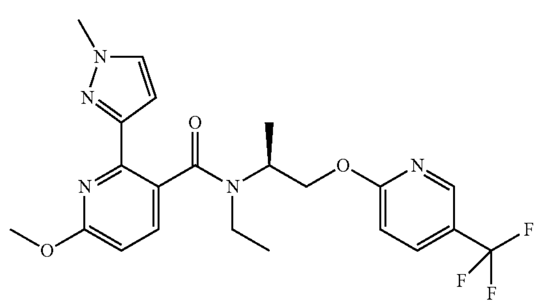 [SMILES: CCN(C(=O)c1ccc(OC)nc1-c1ccn(C)n1)[C@@H](C)COc1ccc(C(F)(F)F)cn1] | 0.15 (50 nM) | 106 | 707 | 12 |

TABLE 3-continued

Comparison of biological data of the compounds of the present
invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| 38 | 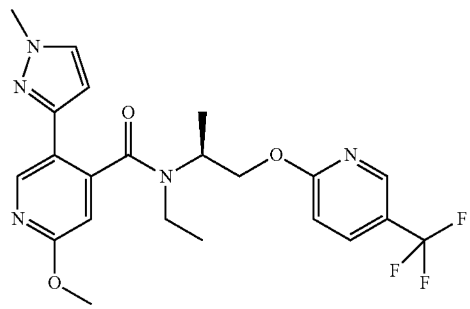 [SMILES: CCN(C(=O)c1cc(OC)ncc1-c1ccn(C)n1)[C@@H](C)COc1ccc(C(F)(F)F)cn1] | 2.4 (0.5 nM) | 323 | 135 | 12 |
| 40 | 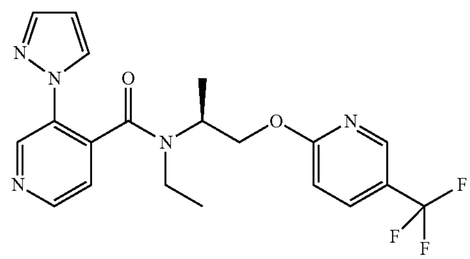 [SMILES: CCN(C(=O)c1ccncc1-n1cccn1)[C@@H](C)COc1ccc(C(F)(F)F)cn1] | 13 (0.5 nM) | 1565 | 120 | 10 |
| 58 | 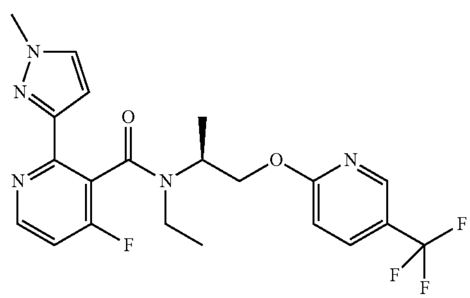 [SMILES: CCN(C(=O)c1c(F)ccnc1-c1ccn(C)n1)[C@@H](C)COc1ccc(C(F)(F)F)cn1] | 3.5 (0.5 nM) | 327 | 93 | 41 |
| 69 | 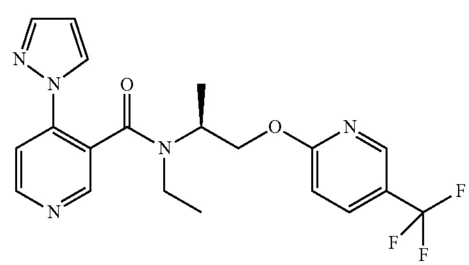 [SMILES: CCN(C(=O)c1cnccc1-n1cccn1)[C@@H](C)COc1ccc(C(F)(F)F)cn1] | 2.2 (0.5 nM) | 305 | 139 | 13 |
| 59 | 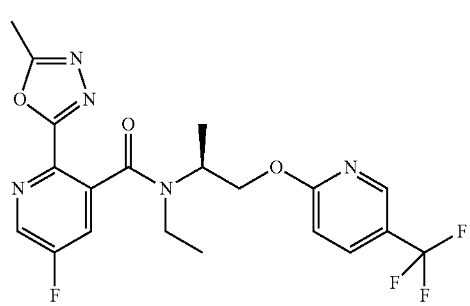 [SMILES: CCN(C(=O)c1cc(F)cnc1-c1nnc(C)o1)[C@@H](C)COc1ccc(C(F)(F)F)cn1] | 31 (0.5 nM) | 6637 | 214 | >130 |

TABLE 3-continued

Comparison of biological data of the compounds of the present
invention with the closest prior art compounds in WO2016/034882

| Example | Structure | Assay A OX1R Kb [nM] (Orexin A concentration) | Assay B OX2R Kb [nM] (0.5 nM Orexin A concentration) | OX2RKb/ OX1R Kb | Assay C: Human MST $t_{1/2}$ [min] |
|---|---|---|---|---|---|
| Ex 84 in WO2016/ 034882 | 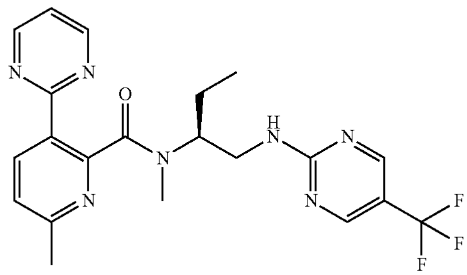 [SMILES: CC[C@@H](CNc1ncc(C(F)(F)F)cn1)N(C)C(=O)c1nc(C)ccc1-c1ncccn1] | 2.20 (0.5 nM) | 229 | 104 | 41 |
| 35 | 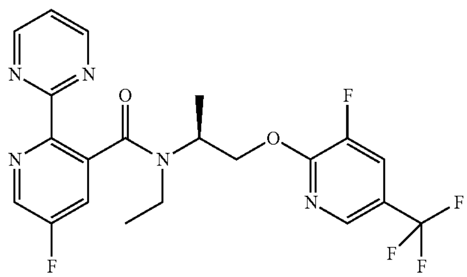 [SMILES: CCN(C(=O)c1cc(F)cnc1-c1ncccn1)[C@@H](C)COc1ncc(C(F)(F)F)cc1F] | 4.6 (0.5 nM) | 3249 | 706 | >130 |
| 70 | 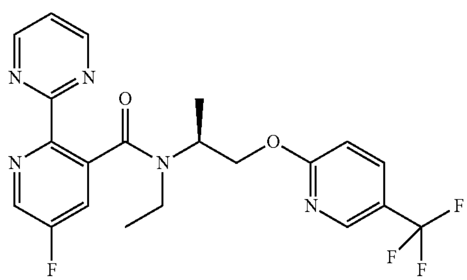 [SMILES: CCN(C(=O)c1cc(F)cnc1-c1ncccn1)[C@@H](C)COc1ccc(C(F)(F)F)cn1] | 1.5 (0.5 nM) | 1036 | 691 | >130 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/ seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole. Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

Antidepressants
Mood stabilizers
Antipsychotics
Anxiolytics
Antiepileptic drugs
Sleeping agents
Cognitive enhancer
Stimulants
Non-stimulant medication for attention deficit hyperactivity disorder
Additional psychoactive drugs.

General Synthetic Methods

The invention also provides a process for making compounds of Formula (I). Unless specified otherwise, $Ar^1$ and $Ar^2$ in the formulas below shall have the meaning as defined for formula I in the detailed description of the invention above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), liquid chromatography-mass spectrometry (LC-MS) if desired, and intermediates and products may be purified by chromatography and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) may be synthesized by the method illustrated in Scheme 1:

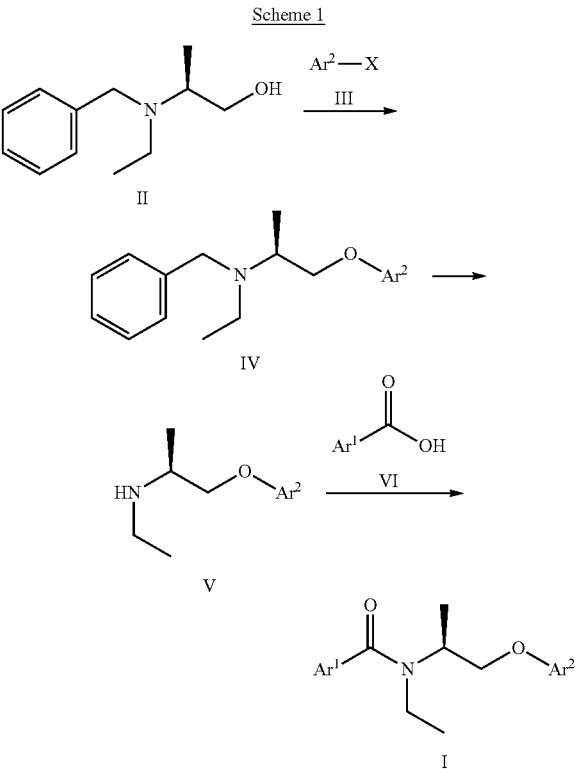

As shown in scheme 1, reacting the alcohol of formula II with an aryl halide III (X=halide) in a nucleophilic aromatic substitution reaction, in a suitable solvent such as dioxane, THF or DMF and in the presence of a suitable base such as potassium tert-butoxide or NaH, provides an ether of formula IV. Debenzylation reactions are described in 'Protective Groups in Organic Synthesis', 3' edition, T. W. Greene and P. G. M. Wuts, Wiley-Interscience (1999). Debenzylation of compound IV using 1-chloroethylchloroformate as a hydrogenating reagent may be used in a suitable solvent such as 1,2-dichloroethane to provide an amine of formula V. Alternatively, for compounds of formula IV, in which Ar² is a substituted pyridine the debenzylation may also be performed under a pressure of hydrogen in the presence of a suitable catalyst such as Pd/C or Pd(OH)₂ in a suitable solvent such as methanol.

Peptide coupling reactions known to the person skilled in the art (see for example M. Bodanszky, 1984, The Practice of Peptide Synthesis, Springer-Verlag) can be applied to react the secondary amine of formula V with a carboxylic acid of formula VI to yield a compound of formula I. For example, amine V and carboxylic acid VI in a suitable solvent such as acetonitrile or DMF in the presence of a base such as DIPEA yields upon treatment with the coupling agent 2-chloro-4,5-dihydro-1,3-dimethyl-1H-imidazolium hexafluorophosphate (CIP) or 1-[bis(dimethylamino)methylene]-1H-1,2,3-triazolo[4,5-b]pyridinium 3-oxide hexafluorophosphate (HATU) a compound of formula I.

Alternatively, compounds of Formula I can be synthesized as illustrated in Scheme 2:

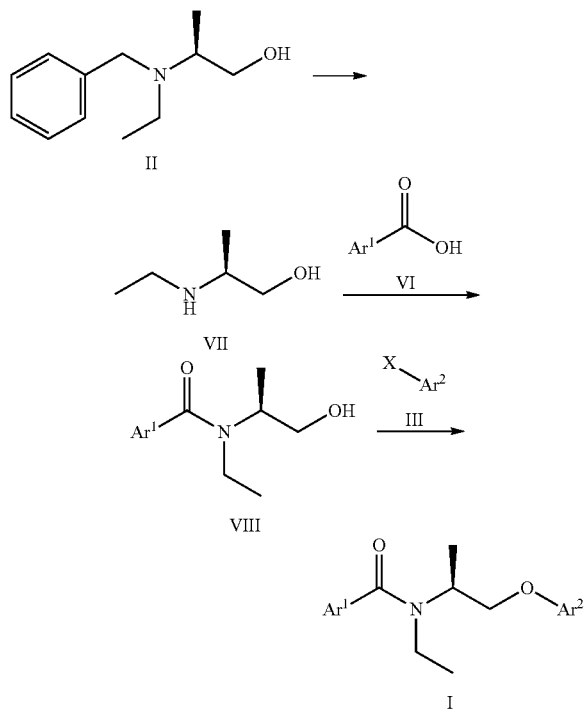

Debenzylation reactions are described in 'Protective Groups in Organic Synthesis', 3' edition, T. W. Greene and P. G. M. Wuts, Wiley-Interscience (1999). Debenzylation of compound II in a suitable solvent such as MeOH, under a pressure of hydrogen in the presence of a suitable catalyst such as Pd/C results in a secondary amine of formula VII.

Peptide coupling reactions known to the person skilled in the art (see for example M. Bodanszky, 1984, The Practice of Peptide Synthesis, Springer-Verlag) can be applied to react the secondary amine of formula VII with a carboxylic acid of formula VI to yield a compound of formula VIII. For example, carboxylic acid VI in a suitable solvent such as DCM, DMF and toluene upon treatment with thionyl chloride or oxalyl chloride yields an acid chloride which is then treated with an amine of formula VII, in a suitable solvent such as DCM, DMF or THF, in the presence of a suitable base such as TEA, to provide a compound of formula VIII. Other peptide coupling reagents such as HATU in a suitable solvent such as DMF in the presence of a suitable base such as DIPEA may be used.

Reacting the alcohol of formula VIII with an aryl halide III in a nucleophilic aromatic substitution reaction, in a suitable solvent such as dioxane, DMSO or DMF and in the presence of a suitable base such as potassium tert-butoxide or NaH, provides a compound of formula I.

Alternatively, an amine of Formula V can be synthesized as illustrated in Scheme 3:

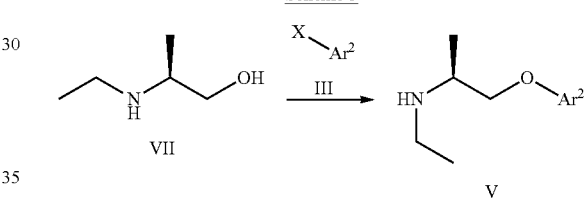

Reacting the alcohol of formula VII with an aryl halide III (X=halide) in a nucleophilic aromatic substitution reaction, in a suitable solvent such as dioxane, DMSO and DMF and in the presence of a suitable base such as potassium tert-butoxide or NaH, provides a compound of formula V.

Alternatively, compounds of Formula I can be synthesized as illustrated in Scheme 4:

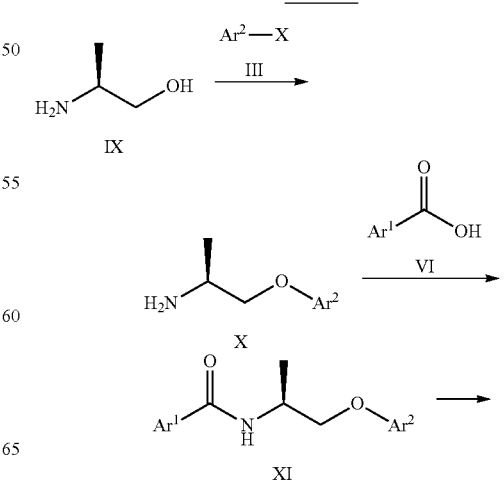

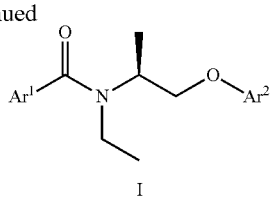

I

Reacting the alcohol of formula IX with an aryl halide III in a nucleophilic aromatic substitution reaction, in a suitable solvent such as dioxane or DMF and in the presence of a suitable base such as potassium tert-butoxide or NaH, provides a compound of formula X.

Peptide coupling reactions known to the person skilled in the art (see for example M. Bodanszky, 1984, The Practice of Peptide Synthesis, Springer-Verlag) can be applied to react a secondary amine of formula X with a carboxylic acid of formula VI to yield a compound of formula XI. For example, a peptide coupling reagents such as TBTU or HATU in a suitable solvent such as DMF in the presence of a suitable base such as DIPEA may be used. Alkylation of amide XI using a suitable alkylation agent such as ethyl iodide in a suitable solvent such as DMF and a suitable base such as NaH or potassium tert-butoxide provides a compound of formula I.

Alternatively, compounds of Formula I can be synthesized as illustrated in Scheme 5:

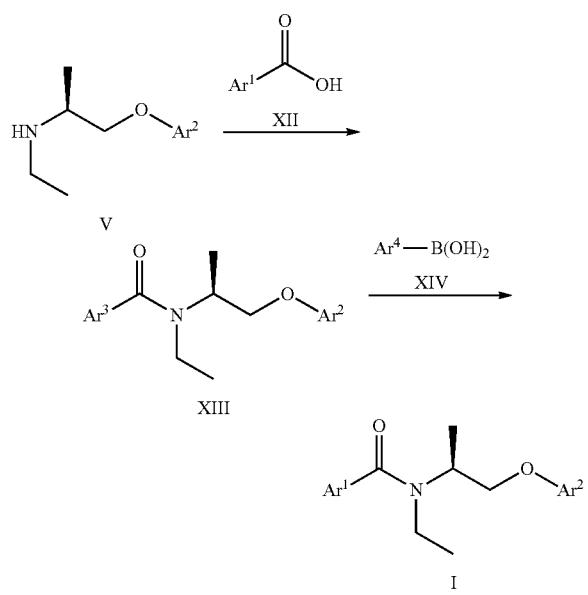

Scheme 5 wherein
$Ar^3$ represents a halosubstituted heteroaryl corresponding to the core of the $Ar^1$ group as defined for formula I in the detailed description of the invention above;
$Ar^4$ represents a heteroaryl group corresponding to the peripheral aromatic moiety of the Ar1 group as defined for formula I in the detailed description of the invention above.

Peptide coupling reactions known to the person skilled in the art (see for example M. Bodanszky, 1984, The Practice of Peptide Synthesis, Springer-Verlag) can be applied to react the secondary amine of formula V with a halo substituted heteroaryl ($Ar^3$) carboxylic acid of formula XII to yield a compound of formula XIII. For example, amine V and halo substituted heteroaryl ($Ar^3$) carboxylic acid XII in a suitable solvent such as acetonitrile or DMF in the presence of a base such as DIPEA yields upon treatment with the coupling agent CIP or HATU an amide of formula XIII. Via metal-catalyzed reactions such as a Stille or Suzuki-type cross-coupling reactions or Cu-catalyzed N-arylation reactions known to the person skilled in the art an amide of formula XIII can be converted to compounds of Formula I. For example, an amide XIII and an heteroaryl ($Ar^4$) boronic acid or ester of formula XIV in a suitable solvent such as dioxane, DMF or THF in the presence of a suitable base such as $Cs_2CO_3$ or $K_2CO_3$ and in the presence of a suitable catalyst such as Pd-PEPPSI-IPent or Pd(dppf)$Cl_2$.DCM yields compounds of formula I. Alternatively, an amide XIII and an NH-heteroaryl ($Ar^4$) moiety such as pyrazole or triazole in a suitable solvent such as acetonitrile or DMF, in the presence of a suitable Cu-catalyst such as $Cu_2O$ or CuI and a suitable base such as $Cs_2CO_3$ or $K_2CO_3$ yields compounds of formula I.

Alternatively, an alcohol of formula VIII can be synthesized as illustrated in Scheme 6:

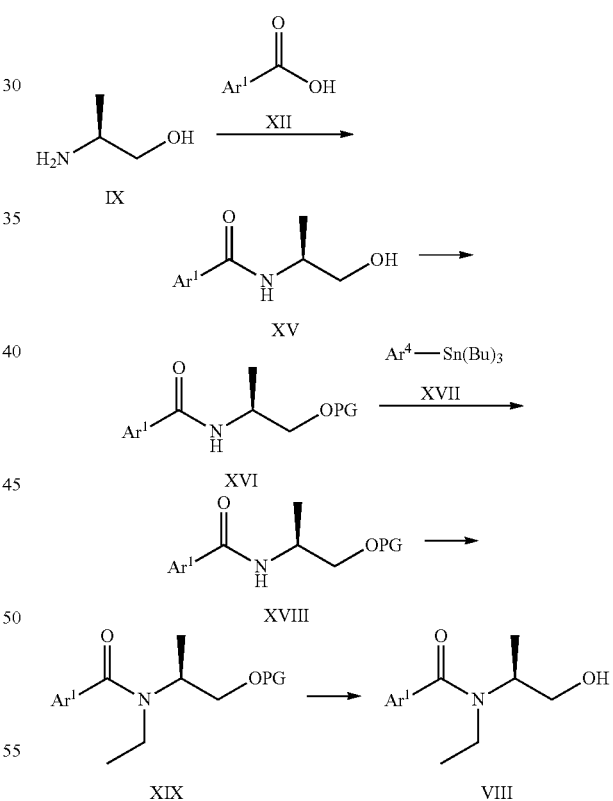

Scheme 6 wherein
$Ar^3$ represents a halosubstituted heteroary group I corresponding to the core of the $Ar^1$ group as defined for formula I in the detailed description of the invention above;
$Ar^4$ represents a heteroaryl group corresponding to the peripheral aromatic moiety of the Ar1 group as defined for formula I in the detailed description of the invention above.

Peptide coupling reactions known to the person skilled in the art (see for example M. Bodanszky, 1984, The Practice of Peptide Synthesis, Springer-Verlag) can be applied to react the secondary amine of formula IX with a carboxylic acid of formula XII to yield a compound of formula XV. For example, a halo substituted heteroaryl (Ar$^3$) carboxylic acid of formula XII in a suitable solvent such as DCM upon treatment with CDI yields an amide of formula XV. Protecting alcohols are described in 'Protective Groups in Organic Synthesis', 3' edition, T. W. Greene and P. G. M. Wuts, Wiley-Interscience (1999). For example, silyl protecting groups (PG) such as the tert-butyldimethylsilyl (TBDMS) group can be introduced by reacting the amide XV with TBDMS-Cl in a suitable solvent such as DCM in the presence of imidazole provides amides of formula XVI.

Via a metal-catalysed coupling reaction, such as a Stille reaction the amide of formula XVI can be transformed to an amide of formula XVIII. For example, the amide of formula XVI is converted with an aryl (Ar$^4$) tributyltin of formula XVII in a suitable solvent such as 1,2-dimethoxyethane, in the presence of a suitable catalyst such as Pd(PPh$_3$)$_4$ and in the presence of CuI to the amide of formula XVIII. Alkylation of the amide XVIII using a suitable alkylation agent such as ethyl iodide in a suitable solvent such as DMF and a suitable base such as NaH or potassium tert-butoxide provides an amide of formula XIX. Deprotection reactions described in 'Protective Groups in Organic Synthesis', 3' edition, T. W. Greene and P. G. M. Wuts, Wiley-Interscience (1999) can be applied in providing alcohol VIII from compound XVIII. For example tetra-n-butylammonium fluoride in a suitable solvent such as THF may be used.

Further modifications of compounds of formula I can be performed following methods known to the person skilled in the art. For example a fluoropyridine can be reacted with an alcohol in a nucleophilic aromatic substitution reaction to provide a compound of formula I.

Intermediate carboxylic acids VI and XII are commercially available or they may be synthesized according or in analogy to methods described in the literature.

EXPERIMENTAL SECTION

List of Abbreviations
RT room temperature
ESI-MS electrospray ionization mass spectrometry
CIP 2-chloro-4,5-dihydro-1,3-dimethyl-1H-imidazolium hexafluorophosphate
CDI 1,1'-carbonyldiimidazole
dppf 1,1'-bis(diphenylphosphanyl)ferrocene
PEPPSI-IPr [1,3-bis(2,6-diisopropylphenyl)imidazol-2-ylidene](3-chloropyridyl)palladium(II) dichloride
APCI atmospheric pressure chemical ionization
aq. aqueous
MS mass spectrum
MeOH methanol
EtOH ethanol
EA ethyl acetate
DMF N,N-dimethylformamide
DMA N,N-dimethylacetamide
DCM dichloromethane
DMSO dimethylsulfoxide
THF tetrahydrofuran
DIPEA N,N-diisopropylethylamine
HATU 1-[bis(dimethylamino)methylene]-1H-1,2,3-triazolo[4,5-b]pyridinium 3-oxide hexafluorophosphate
TBTU O-(benzotriazol-1-yl)-N,N,N',N'-tetramethyl-uronium tetrafluoroborate
TEA triethylamine
Rt retention time
h hour(s)
d day(s)
sat. saturated
ACN acetonitrile
TFA trifluoroacetic acid
TBDMS tert-butyldimethylsilyl
TBAF tetra-n-butylammonium fluoride
M molarity
N normality
HPLC high-performance liquid chromatography
HPLC-MS high-performance liquid chromatography-mass spectrometry
TLC thin layer chromatography
LC-MS liquid chromatography-mass spectrometry HPLC-Methods:

Method Name: A

Column: Venusil XBP-C18, 2.1×50 mm, 5 μm

Column Supplier: Agilent

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 100 | 0 | 1.0 | 50 |
| 0.30 | 100 | 0 | 1.0 | 50 |
| 2.10 | 40 | 60 | 1.0 | 50 |
| 2.48 | 40 | 60 | 1.0 | 50 |
| 2.50 | 100 | 0 | 1.0 | 50 |
| 3.00 | 100 | 0 | 1.0 | 50 |

Method Name: B

Column: Xselect CSH Phenyl-Hexyl, 4.6×50 mm, 2.5 μm,

Column Supplier: Waters

| Gradient/Solvent Time [min] | % Sol [90% H$_2$O + 10% ACN + 0.1% HCOOH] | % Sol [90% ACN + 10% H$_2$O] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: C

Column: Chromolith Flash RP-18e 25-2 mm

Column Supplier: Merck

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Method Name: D
Column: Acquity BEH C18 2.1×100 mm, 1.7 µm
Column Supplier: Waters

| Gradient/Solvent Time [min] | % Sol [10 mm $CH_3COONH_4$ in $H_2O$] | % Sol [ACN] | Flow [mL/min] | Temp [° C.] |
|---|---|---|---|---|
| 0.00 | 95 | 5 | 0.3 | 35 |
| 0.60 | 95 | 5 | 0.3 | 35 |
| 1.50 | 85 | 15 | 0.3 | 35 |
| 4.00 | 45 | 55 | 0.3 | 35 |
| 5.50 | 5 | 95 | 0.3 | 35 |
| 7.80 | 5 | 95 | 0.3 | 35 |
| 9.00 | 95 | 5 | 0.3 | 35 |
| 10.0 | 95 | 5 | 0.3 | 35 |

Method Name: E
Column: XBridge C18, 4.6×30 mm, 3.5 µm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: F
Column: XBridge C18, 3×30 mm, 2.5 µm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: G
Column: Sunfire C18, 3.0×30 mm, 2.5 µm
Column Supplier: Waters

| Gradient/Solvent Time [min] | % Sol [ACN 0.08% TFA] | Flow [mL/min] | Temp [° C.] |
|---|---|---|---|
| 0.0 | 5.0 | 1.5 | 40 |
| 1.3 | 100.0 | 1.5 | 40 |
| 1.5 | 100.0 | 1.5 | 40 |
| 1.6 | 5.0 | 1.5 | 40 |

Method Name: H
Column: Sunfire, 3×30 mm, 2.5 µm
Column Supplier: Waters

| Gradient/Solvent Time [min] | % Sol [$H_2O$, 0.1% TFA] | % Sol [ACN] | Flow [mL/min] | Temp [° C.] |
|---|---|---|---|---|
| 0.00 | 97 | 3 | 2.2 | 60 |
| 0.02 | 97 | 3 | 2.2 | 60 |
| 1.00 | 0 | 100 | 2.2 | 60 |
| 1.25 | 0 | 100 | 3 | 60 |
| 1.40 | 0 | 100 | 3 | 60 |

Method Name: I
Column: Sunfire C18_3.0×30 mm_2.5 µm
Column Supplier: Waters

| Gradient/Solvent Time [min] | % Sol [$H_2O$, 0.1% TFA (v/v)] | % Sol [ACN] | Flow [mL/min] | Temp [° C.] |
|---|---|---|---|---|
| 0.0 | 98.0 | 2.0 | 2.0 | 60 |
| 1.2 | 0.0 | 100.0 | 2.0 | 60 |
| 1.4 | 0.0 | 100.0 | 2.0 | 60 |

Method Name: J
Column: Sunfire C18_3.0×30 mm_2.5 µm
Column Supplier: Waters

| Gradient/Solvent Time [min] | % Sol [$H_2O$, 0.1% TFA] | % Sol [ACN, 0.08% TFA] | Flow [mL/min] | Temp [° C.] |
|---|---|---|---|---|
| 0.00 | 95 | 5 | 1.5 | 60 |
| 1.30 | 100 | 0 | 1.5 | 60 |
| 1.50 | 100 | 0 | 1.5 | 60 |
| 1.60 | 95 | 5 | 1.5 | 60 |

Method Name: K
Column: XBridge C18_3.0×30 mm_2.5 µm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 95 | 5 | 1.5 | 60 |
| 1.30 | 100 | 0 | 1.5 | 60 |
| 1.50 | 100 | 0 | 1.5 | 60 |
| 1.60 | 95 | 5 | 1.5 | 60 |

Method Name: L
Column: XBridge BEH C18, 2.1×30 mm, 1.7 µm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: M
Column: Atlantis T3, 3.0 μm 2.1×50 mm
Column Supplier: Waters

| Gradient/ Solvent Time [min] | % Sol [90% H$_2$O + 10% ACN + 0.1% HCOOH] | % Sol [90% ACN + 10% H$_2$O] | Flow [mL/min] | Temp [° C.] |
|---|---|---|---|---|
| 0.00 | 100 | 0 | 0.7 | 35 |
| 2.40 | 0 | 100 | 0.7 | 35 |
| 2.70 | 0 | 100 | 0.7 | 35 |
| 2.80 | 100 | 0 | 0.7 | 35 |
| 3.00 | 100 | 0 | 0.7 | 35 |

Method Name: N
Column: Synergi Hydro RP100A, 2.5 μm, 3×50 mm
Column Supplier: Phenomenex

| Gradient/ Solvent Time [min] | % Sol [90% H$_2$O + 10% ACN + 10 nM NH$_4$COOH] | % Sol [90% ACN + 10% H$_2$O + 10 nM NH$_4$COOH] | Flow [mL/min] | Temp [° C.] |
|---|---|---|---|---|
| 0.00 | 100 | 0 | 1.2 | RT |
| 0.50 | 100 | 0 | 1.2 | RT |
| 6.50 | 0 | 100 | 1.2 | RT |
| 7.50 | 0 | 100 | 1.2 | RT |
| 8.00 | 100 | 0 | 1.2 | RT |
| 9.00 | 100 | 0 | 1.2 | RT |

Method Name: O
Column: HSS C18, 1.8 μm, 2.1×50 mm
Column Supplier: Waters

| Gradient/ Solvent Time [min] | % Sol [90% H$_2$O + 10% ACN + 0.1% CF$_3$COOH] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: P
Column: BEH C18, 1.7 μm, 2.1×50 mm
Column Supplier: Waters

| Gradient/ Solvent Time [min] | % Sol [90% H$_2$O + 10% ACN + 5 nM NH$_4$COOH] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: Q
Column: CSH C18, 1.7 μm, 2.1×50 mm
Column Supplier: Waters

| Gradient/ Solvent Time [min] | % Sol [90% H$_2$O + 10% ACN + 0.1% HCOOH] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: R
Column: Xselect CSH, 2.5 μm, 4.6×50 mm
Column Supplier: Waters

| Gradient/ Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: S
Column: XBridge C18_3.0×30 mm_2.5 μm
Column Supplier: Waters

| Gradient/Solvent Time [min] | % Sol [H$_2$O, 0.1% NH$_3$] | % Sol [ACN] | Flow [mL/min] | Temp [° C.] |
|---|---|---|---|---|
| 0.0 | 95.0 | 5.0 | 1.5 | 40 |
| 1.3 | 0.0 | 100.0 | 1.5 | 40 |
| 1.5 | 0.0 | 100.0 | 1.5 | 40 |
| 1.6 | 95.0 | 5.0 | 1.5 | 40 |

Method Name: T
Column: Zorbax Eclipse XDB-C18, 3.5 μm, 4.6×50 mm
Column Supplier: Agilent

| Gradient/ Solvent Time [min] | % Sol [90% H$_2$O + 10% ACN + 5 nM NH$_4$COOH] | % Sol [90% ACN + 10% H$_2$O] | Flow [mL/min] | Temp [° C.] |
|---|---|---|---|---|
| 0.00 | 100 | 0 | 1.3 | 35 |
| 4.50 | 0 | 100 | 1.3 | 35 |
| 5.80 | 0 | 100 | 1.3 | 35 |
| 6.00 | 100 | 0 | 1.3 | 35 |

Method Name: U
Column: BEH C18, 1.7 μm, 2.1×50 mm
Column Supplier: Waters

| Gradient/ Solvent Time [min] | % Sol [90% H$_2$O + 10% ACN + 5 nM NH$_4$HCO$_3$] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |

-continued

| Gradient/ Solvent Time [min] | % Sol [90% H$_2$O + 10% ACN + 5 nM NH$_4$HCO$_3$] | % Sol [90% ACN + 10% H$_2$O] | Flow [mL/min] | Temp [° C.] |
|---|---|---|---|---|
| 1.55 | 100 | 0 | 0.7 | 35 |
| 1.75 | 100 | 0 | 0.7 | 35 |

Method Name: V
Column: Luna-C18, 2.0×50 mm, 5 μm
Column Supplier: Agilent

| Gradient/ Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 99 | 1 | 0.8 | 40 |
| 0.40 | 99 | 1 | 0.8 | 40 |
| 3.40 | 0 | 100 | 0.8 | 40 |
| 3.85 | 0 | 100 | 0.8 | 40 |
| 3.86 | 99 | 1 | 0.8 | 40 |
| 4.50 | 99 | 1 | 0.8 | 40 |

Method Name: X
Column: Sunfire C18, 3.0×30 mm, 2.5 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |

Method Name: Z
Column: Luna-C18 5 μm, 2.0*50 mm
Column Supplier: Phenomenex

| Gradient/ Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 99 | 1 | 0.8 | 40 |
| 0.40 | 99 | 1 | 0.8 | 40 |
| 3.40 | 0 | 100 | 0.8 | 40 |
| 3.85 | 0 | 100 | 0.8 | 40 |
| 3.86 | 99 | 1 | 0.8 | 40 |
| 4.50 | 99 | 1 | 0.8 | 40 |

HPLC traces and NMR spectra of the examples and some advanced intermediates are of increased complexity due to the fact that these compounds exist in an equilibrium of multiple rotameric forms. In the case of multiple peaks in the HPLC spectrum, the retention time of the main peak is reported.

Preparation of intermediates

Acid Intermediates

| Intermediate | Name | Structure | Reference / Source |
|---|---|---|---|
| A-1 | 6-Methyl-3-[1,2,3]triazol-2-yl-pyridine-2-carboxylic acid | 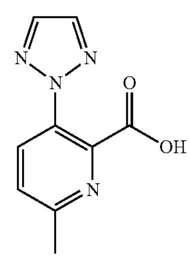 | WO2012/89606, Page 44, Intermediate D40 |
| A-2 | 3-(4-Fluoro-phenyl)-pyridine-2-carboxylic acid | 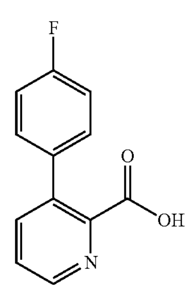 [SMILES: O=C(O)c1ncccc1-c1ccc(F)cc1] | commercially available from Combi-Blocks catalog number YA-6147, MDL number: MFCD14700040 |

-continued

| Intermediate | Name | Structure | Reference / Source |
|---|---|---|---|
| A-3 | 6-Methyl-3-pyrimidin-2-yl-pyridine-2-carboxylic acid | 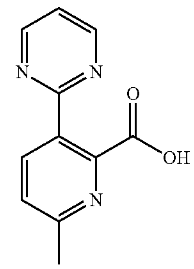 [SMILES: Cc1ccc(-c2ncccn2)c(C(=O)O)n1] | commercially available from FCHGROUP catalog number FCH1789175, MDL number: MFCD24479765 |
| A-4 | 2-Methyl-4-phenyl-pyrimidine-5-carboxylic acid | 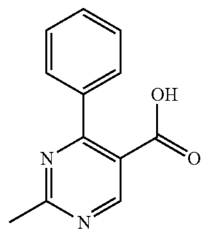 [SMILES: Cc1ncc(C(=O)O)c(-c2ccccc2)n1] | commercially available from Fluorochem catalog number 322095, MDL number: MFCD02682072 |
| A-5 | 3-Phenyl-pyridine-2-carboxylic acid | 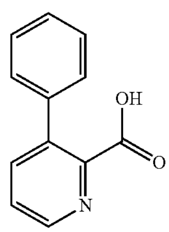 [SMILES: O=C(O)c1ncccc1-c1ccccc1] | commercially available from Fluorochem catalog number 065974, MDL number: MFCD04114112 |
| A-6 | 4-Phenyl-pyrimidine-5-carboxylic acid | 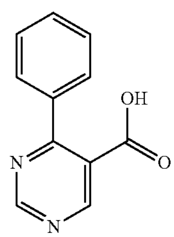 [SMILES: O=C(O)c1cncnc1-c1ccccc1] | commercially available from Emolecules catalog number 45773153, MDL number: MFCD09835877 |
| A-7 | 3-Bromo-5-methyl-pyridine-2-carboxylic acid | 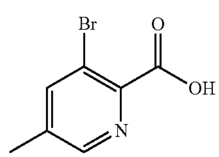 | commercially available from Fluorochem catalog number 093353, MDL number: MFCD17214206 |
| A-8 | 2-Chloro-6-methoxy-nicotinic a | 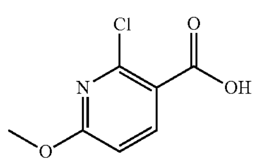 | e.g. J. Chem. Soc., Perkin Trans. 1, 1988, page 227; commercially available from Sigma-Aldrich, catalog number ADE000607, MDL number MFCD08236845 |
| A-9 | 2-Chloro-5-methyl-nicotinic ac | 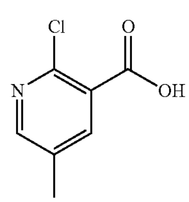 | WO2005/9965 Page 42, Preparation 2; commercially available from Fluorochem catalog number 078345, MDL number: MFCD07375371 |

-continued

| Intermediate | Name | Structure | Reference / Source |
|---|---|---|---|
| A-10 | 4-Bromo-nicotinic acid | 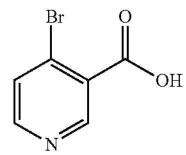 | US2011/230495 Page 21, Intermediate 196; commercially available from Sigma-Aldrich catalog number 721999, MDL number: MFCD04114236 |
| A-11 | 3-Bromo-pyridine-2-carboxylic ac | 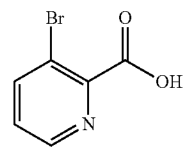 | J. Am. Chem. Soc., 2008, 130, 9942; commercially available from Fluorochem catalog number 012713, MDL number: MFCD01320380 |
| A-12 | 3-Chloro-6-methoxy-pyridine-2-carboxylic acid | 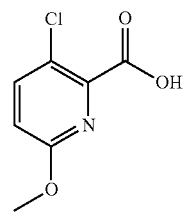 | US2005/192294 Page 16, Intermediate J; commercially available from Fluorochem catalog number 235425, MDL number: MFCD11044291 |
| A-13 | 5-Chloro-2-methoxy-isonicotinic acid | 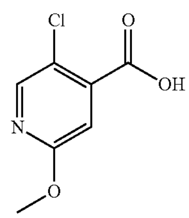 | WO2007/084455 Page 120, Intermediate 321; commercially available from Fluorochem catalog number 077591, MDL number: MFCD07375110 |
| A-14 | 2-Chloro-6-trifluoromethyl-nicotinic acid | 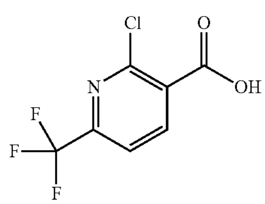 [SMILES: O=C(O)c1ccc(C(F)(F)F)nc1Cl] | e.g. Eur. J. Org. Chem., 2004, (18), 3793; commercially available from Fluorochem catalog number 009102, MDL number: MFCD01862658 |
| A-15 | 2-Chloro-4-fluoro-nicotinic ac | 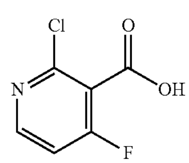 [SMILES: O=C(O)c1c(F)ccnc1Cl] | WO2011/053574 Page 44, Intermediate 64-2; commercially available from Fluorochem catalog number 324998, MDL number: MFCD11040264 |
| A-16 | 3-Bromo-5-fluoro-pyridine-2-carboxylic acid | 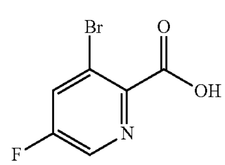 | Commercially available from Sigma-Aldrich catalog number 772518, MDL number: MFCD12827684 |
| A-17 | 3-Bromo-isonicotinic acid | 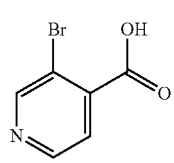 | e.g. Bioorg. Med. Chem., 2015, 23, 3013; Commercially available from Sigma-Aldrich catalog number 714658, MDL number: MFCD00040944 |

| Intermediate | Name | Structure | Reference / Source |
|---|---|---|---|
| A-18 | 2-Chloro-5-trifluoromethyl-nicotinic acid | 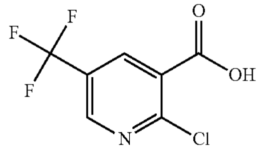 [SMILES: O=C(O)c1cc(C(F)(F)F)cnc1Cl] | e.g. Eur. J. Org. Chem., 2003, (8), 1559; Commercially available from Sigma-Aldrich catalog number 734926, MDL number: MFCD08741353 |
| A-19 | 4-Bromo-6-trifluoromethyl-nicotinic acid | 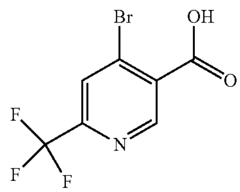 [SMILES: O=C(O)c1cnc(C(F)(F)F)cc1Br] | Commercially available from Emolecules catalog number 44825736, MDL number: MFCD13188815 |
| A-20 | 3-Chloro-5-trifluoromethyl-pyridine-2-carboxylic acid | 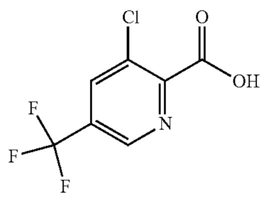 [SMILES: O=C(O)c1ncc(C(F)(F)F)cc1Cl] | U.S. Pat. No. 4,367,336, Page 4, Example 5; commercially available from Fluorochem catalog number 047406, MDL number: MFCD00277482 |
| A-21 | 3-Bromo-5-fluoro-isonicotinic acid | 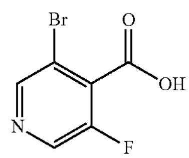 [SMILES: O=C(O)c1c(F)cncc1Br] | e.g. WO2007/123936 Page 67, Intermediate 6; commercially available from Fluorochem catalog number 223271, MDL number: MFCD13181633 |
| A-22 | 3-Chloro-4-trifluoromethyl-pyridine-2-carboxylic acid | 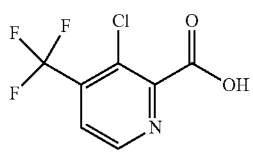 [SMILES: O=C(O)c1nccc(C(F)(F)F)c1Cl] | e.g. Eur. J. Org. Chem., 2004, (18), 3793; commercially available from Manchester catalog number D15517, MDL number: MFCD14581664 |
| A-32 | 2-chloro-5-fluoropyridine-3-carboxylic acid | 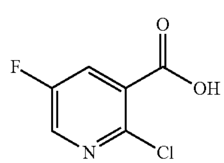 | commercially available from Frontier catalog number C2054, MDL number: MFCD03092932 |

6-Methyl-2-[1,2,3]triazol-2-yl-nicotinic acid A-23

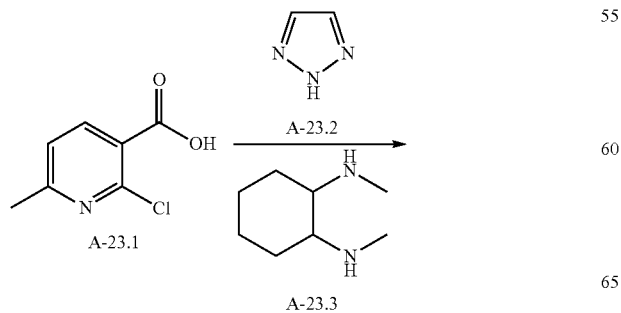

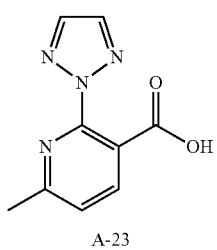

Step 1: In a sealed vial a mixture of A-23.1 (2.00 g, 11.0 mmol), A-23.2 (1.40 mL, 23.0 mmol), CuI (0.22 g, 1.20 mmol), A-23.3 (0.33 mL, 2.30 mmol) and Cs$_2$CO$_3$ (7.60 g, 23.0 mmol) in dry DMF (30 mL) is heated at 110° C. overnight. The cool mixture is poured into water and extracted with Et$_2$O. The aq. phase is acidified with HCl (4N aq. solution) and extracted with EA. The combined organic phases are dried and concentrated to give the crude product which is purified by flash column chromatography on silica gel (using a solvent gradient DCM/MeOH+0.5% HCOOH=100/0 to 95/5) to provide 0.98 g of A-23. ES+/−: 205 [M+H]$^+$; HPLC (Rt): 0.76 min (Method M).

5-Fluoro-2-[1,2,3]triazol-2-yl-nicotinic acid A-24

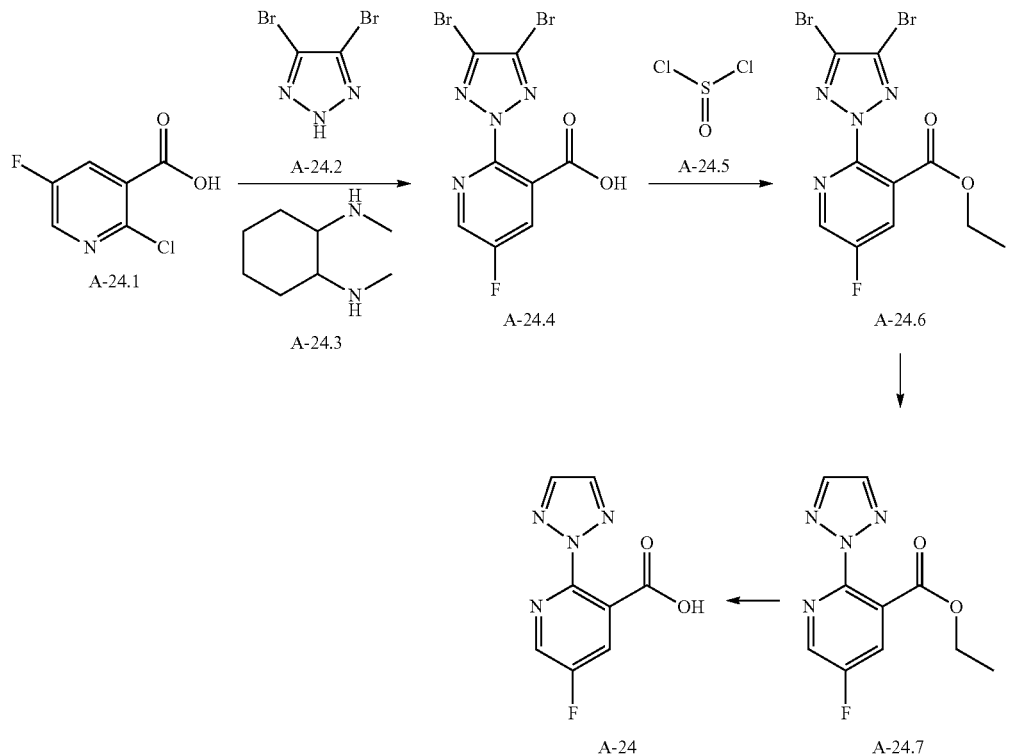

Step 1: A mixture of A-24.1 (2.00 g, 11.0 mmol), A-24.2 (3.80 g, 17.0 mmol), CuI (0.13 g, 0.68 mmol), A-24.3 (0.14 mL, 1.00 mmol) and K$_2$CO$_3$ (2.30 g, 17.0 mmol) in dry DMF (10 mL) is heated to 120° C. by microwave irradiation and stirred for 40 min. The mixture is poured into water and extracted with Et$_2$O. The aq. phase is acidified with HCl (4N aq. solution) and extracted with EA. The combined organic phases are dried and concentrated to give the crude product which is purified by flash column chromatography on silica gel (using a solvent gradient from 100% EA to EA/MeOH=9/1) to provide 3.6 g of A-24.4. APCl+/−: 365 [M+H]$^+$; HPLC (Rt): 1.10 min (Method N).

Step 2: To A-24.4 (3.60 g, 7.90 mmol) in EtOH (36 mL), A-24.5 (0.86 mL, 12.0 mmol) is added dropwise. The mixture is heated at reflux overnight before being cooled to room temperature. Solvents are evaporated. The crude product is purified by flash column chromatography on silica gel. The product is taken up into DCM and washed with NaHCO$_3$ (sat. aq. solution). The organic phase is dried and concentrated to provide 2.3 g of A-24.6. ES+/−: 395 [M+H]$^+$; HPLC (Rt): 1.23 min (Method P).

Step 3: To A-24.6 (2.00 g, 5.00 mmol) in EtOH (25 mL) are added TEA (1.40 mL, 10.0 mmol) and Pd/C (10%, 0.20 g, 1.90 mmol). The reaction vessel is stirred under an atmosphere of hydrogen (2 bar) and stirred overnight. The mixture is filtered through a Celite pad and concentrated. The residue is dissolved in DCM and washed with citric acid (sat. aq. solution). The organic phase is dried and concentrated to afford 1.4 g of A-24.7. ES+/−: 237 [M+H]$^+$; HPLC (Rt): 0.88 min (Method P).

Step 4: To a mixture of A-24.7 (0.85 g, 2.50 mmol) in water (5.0 mL) and THF (15 mL) is added LiOH.H$_2$O (0.32 g, 7.60 mmol) and the mixture is stirred at RT overnight. Solvent is evaporated and the water phase is acidified with HCl (4N aq. solution) and extracted with DCM. The organic phase is dried and concentrated to afford 0.6 g of A-24. ES+/−: 209 [M+H]$^+$; HPLC (Rt): 0.61 min (Method O).

Alternative Route for A-24:

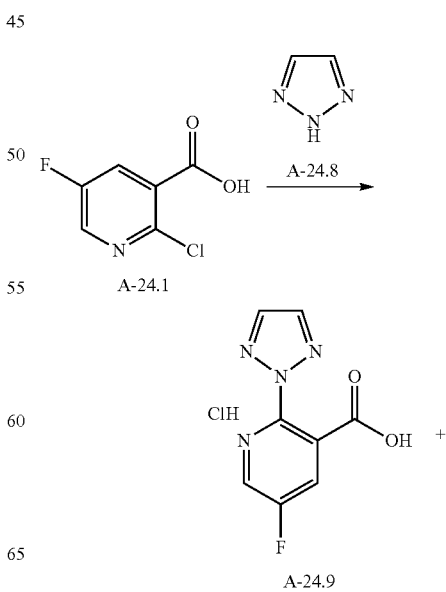

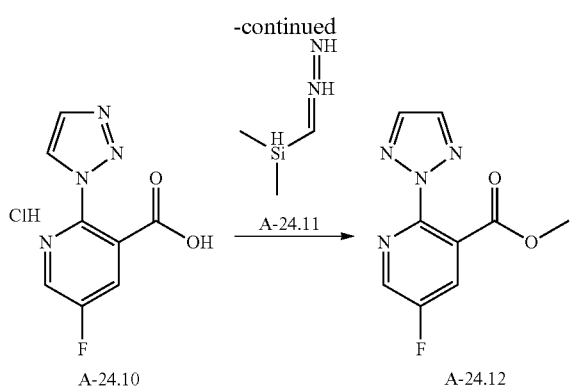

Step 1: A mixture of A-24.1 (15.0 g, 81.0 mmol), A-24.8 (11.0 g, 0.16 mol), CuI (0.94 g, 4.90 mmol) and $Cs_2CO_3$ (53.0 g, 0.16 mol) in 1,4-dioxane (60 mL) and $H_2O$ (0.5 mL) is heated to 100° C. by microwave irradiation and stirred for 10 min. The cold mixture is poured into water and extracted with EA. The organic phase is washed with water and the aq. phase is acidified with HCl (5N aq. solution) and extracted with EA. The combined organic phases are washed with brine, dried and concentrated to afford 12 g of a mixture of A-24.9 and A-24.10.

Step 2: This mixture of A-24.9 and A-24.10 (4.00 g, 6.50 mmol) is dissolved in MeOH (50 mL) and A-24.11 (2M solution in $Et_2O$, 16.4 mL, 32.7 mmol) is added dropwise to the mixture at 0° C. The reaction is stirred at RT overnight. The mixture is quenched with acetic acid and extracted with EA. The organic phase is washed with water and brine, dried and concentrated. The crude product is purified by preparative HPLC (using a solvent gradient $H_2O$/ACN with $NH_4HCO_3$) to afford 2.6 g of A-24.12 as a single isomer. ESI-MS: 223 [M+H]$^+$; HPLC (Rt): 0.77 min (Method P).

The following acid was made in analogy to the above described procedure and the hydrolysis step described for A-24.7 to A-24:

| Acid | Structure | ESI-MS [M + H]$^+$ | HPLC (Rt) [min] | HPLC method |
|---|---|---|---|---|
| A-33 | ![structure] | 225 | 2.05 | Z |

6-Methyl-3-phenyl-pyridine-2-carboxylic acid A-25

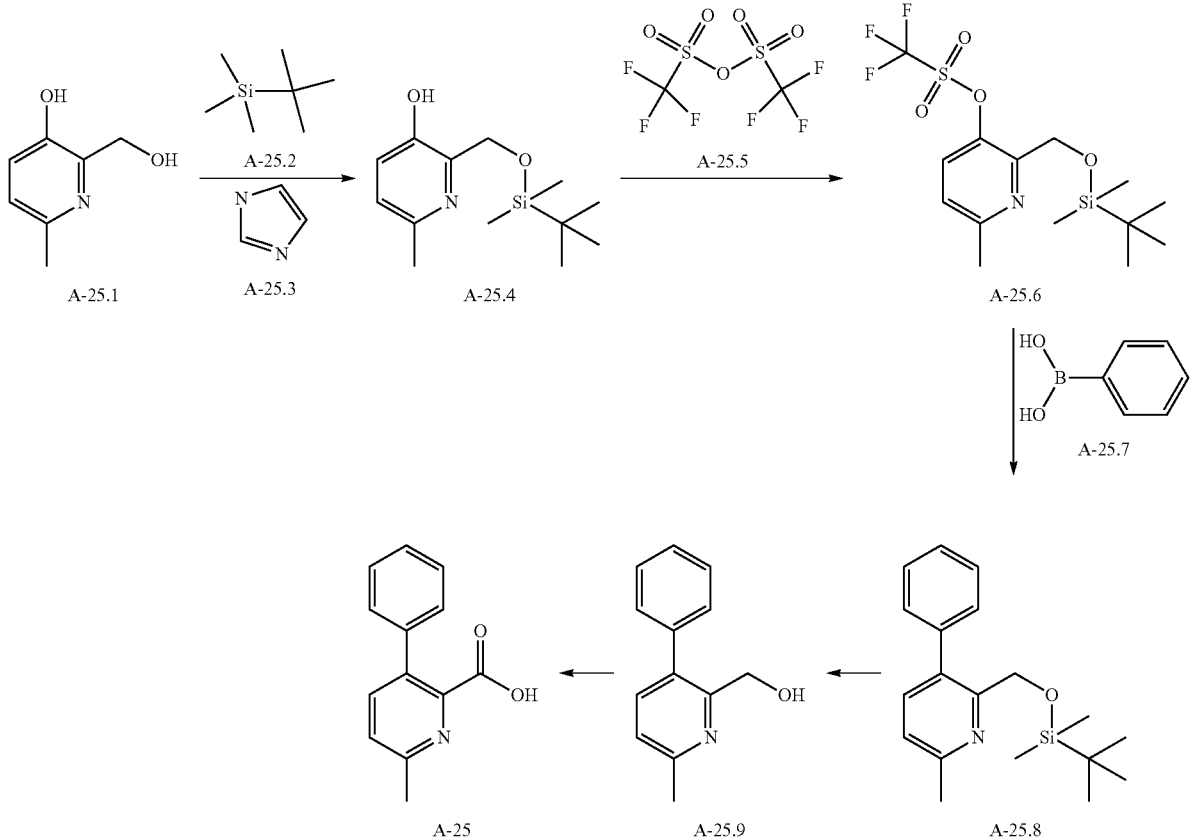

Step 1: To DMF (200 mL) at 0° C. is added A-25.1 (20.0 g, 0.14 mol), A-25.2 (23.0 g, 0.16 mol) and A-25.3 (19.0 g, 0.29 mol) and the mixture is heated to 60° C. and stirred for 16 h. The reaction is cooled to RT and quenched with ice water. The precipitate is filtered, dried and concentrated to yield 19 g of A-25.4.

(10% aq. solution) is added to adjust the pH to 5. The aq. layer is extracted with DCM and the combined organic phases are dried and concentrated to afford 2.2 g of A-25. ES-API: 214 [M+H]$^+$; HPLC (Rt): 3.02 min (Method D).

6-Methyl-4-[1,2,3]triazol-2-yl-nicotinic acid A-26

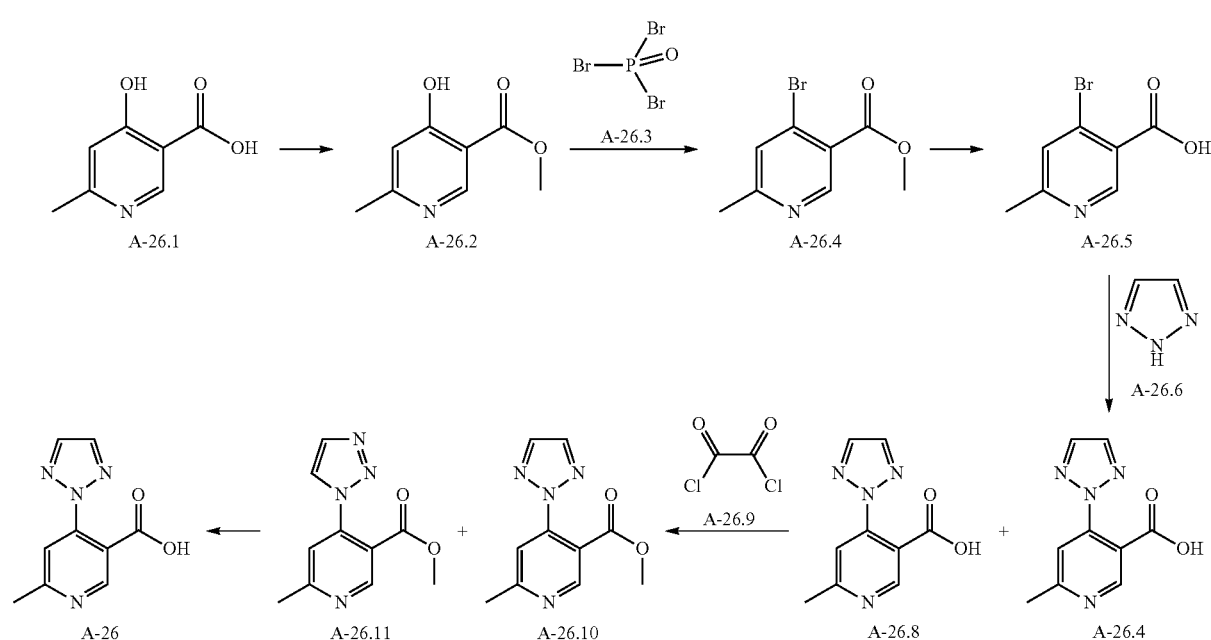

Step 2: To a mixture of A-25.4 (19.0 g, 70.0 mmol) in DCM (250 mL) at 0° C. and under a nitrogen atmosphere are added dropwise DIPEA (37.0 mL, 0.22 mol) and A-25.5 (19.0 mL, 0.11 mol) and the mixture is stirred at RT for 4 h. The reaction is diluted with DCM, washed with ice water, the organic phase is dried and concentrated. The obtained crude product is purified by flash column chromatography on silica gel (using petroleum ether/EA 90/10) to afford 20 g of A-25.6.

Step 3: To a mixture of A-25.6 (20.0 g, 50.0 mmol) and A-25.7 (13.0 g, 0.10 mol) in toluene (200 mL) is added K$_2$CO$_3$ (11.0 g, 80.0 mmol) and the mixture is degassed with argon for 15 min. Pd(PPh$_3$)$_4$ (0.60 g, 0.52 mmol) is added and the mixture is heated to 100° C. and stirred for 6h. The reaction is cooled to RT, diluted with EA and washed with water. The organic phase is dried and concentrated. The obtained crude is purified by flash column chromatography on silica gel (using petroleum ether/EA 95/5 as eluent) to afford 14 g of A-25.8.

Step 4: To A-25.8 (14.0 g, 40.0 mmol) in THF (100 mL) at 0° C. is added dropwise TBAF (140 mL, 140 mmol) and the mixture is stirred at RT for 2h. The reaction is quenched with HCl (1N aq. solution) and the aq. layer is extracted with EA. The combined organic extracts are dried and concentrated. The obtained crude product is purified by flash column chromatography on silica gel (using petroleum ether/EA 90/10) to afford 8.0 g of A-25.9.

Step 5: To a mixture of A-25.9 (8.00 g, 40.0 mmol) in H$_2$O (100 mL) at 0° C. is added KMnO$_4$ (8.50 g, 50.0 mmol). The reaction is filtered, the filtrate is cooled to 0° C. and HCl Step 1: A-26.1 (50.0 g, 0.33 mol) is stirred in HCl (4N in MeOH, 1 L) at 80° C. for 14 h. The mixture is concentrated to afford 50 g of A-26.2. ES-API: 168 [M+H]$^+$; HPLC (Rt): 0.10 min (Method C).

Step 2: To a mixture of A-26.2 (20.0 g, 0.11 mol) in toluene (200 mL) is added A-26.3 (49.0 g, 0.16 mol) and the mixture is heated to 70° C. and stirred for 5 h. The reaction is then cooled to −30° C. and MeOH is added dropwise. The solution is concentrated, dissolved in EA and the organic phase is washed with NaHCO$_3$ (sat. aq. solution) and brine, dried and concentrated. The obtained crude product is purified by flash column chromatography on silica gel (using petroleum ether:EA from 10:1 to 1:1) to afford 20 g of A-26.4. ES-API: 230 [M+H]$^+$; HPLC (Rt): 0.57 min (Method C).

Step 3: To a mixture of A-26.4 (10.0 g, 36.0 mmol) in MeOH (50 mL), THF (50 mL) and H$_2$O (50 mL) is added LiOH.H$_2$O (6.50 g, 0.15 mol). The mixture is stirred at 25° C. for 6 h, then concentrated to provide 12 g of crude A-26.5 which is used without further purification in the next step. ES-API: 216 [M+H]$^+$; HPLC (Rt): 0.74 min (Method A).

Step 4: A mixture of A-26.5 (11.0 g, 40.0 mmol), A-26.6 (6.20 g, 90.0 mmol), CuI (0.97 g, 4.00 mmol), and K$_2$CO$_3$ (14.0 g, 90.0 mmol) in DMF (100 mL) is heated to 120° C. and stirred for 6 h. The mixture is cooled to RT, concentrated and the crude product is purified by preparative HPLC. 4.7 g of a mixture of A-26.7 and A-26.8 is obtained.

Step 5: To a mixture of A-26.7+A-26.8 (3.00 g, 10.0 mmol) in DCM (40 mL) at 0° C. and under a nitrogen atmosphere is added A-26.9 (2.70 g, 20.0 mmol) dropwise. The reaction is stirred at RT for 2 h then cooled to 0° C. and MeOH (30 mL) is added dropwise and the mixture is stirred at RT for 2 h. It is then concentrated, the crude product is taken up in EA and washed with water, dried and concentrated. The crude product is purified by flash column chromatography on silica gel (using a solvent gradient from 1% to 50% EA in petroleum ether) to obtain 0.9 g of A-26.10. ES-API: 219 [M+H]+; HPLC (Rt): 1.61 min (Method A).

Step 6: To A-26.10 (0.80 g, 3.60 mmol) in MeOH (5.0 mL), THF (5.0 mL) and H2O (5.0 mL) is added LiOH.H2O (0.63 g, 14.0 mmol) and the mixture is stirred at RT for 6 h and concentrated. The crude product is purified by preparative HPLC-MS (using a solvent gradient H2O+0.075% TFA with 5-35% ACN) to afford 0.6 g of A-26. ES-API: 205 [M+H]+; HPLC (Rt): 0.62 min (Method A).

3-[1,2,3]Triazol-2-yl-pyridine-2-carboxylic acid A-27

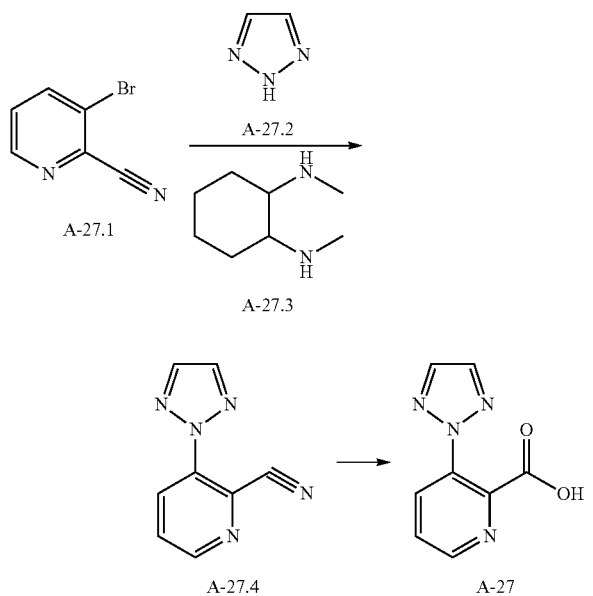

Step 1: A mixture of A-27.1 (1.00 g, 5.50 mmol), A-27.2 (0.60 mL, 11.0 mmol), CuI (0.11 g, 0.50 mmol), A-27.3 (0.14 mL, 1.00 mmol) and K2CO3 (1.50 g, 11.0 mmol) in dry DMF (8.0 mL) is heated at 120° C. by microwave irradiation for 30 min. The mixture is poured into water and extracted with EA. The organic phase is dried and concentrated to give a crude product which is purified by flash column chromatography on silica gel (using an isocratic elution with the mixture of solvent cyclohexane/EA=8/2) to afford 0.4 g A-27.4. APCI+/−: 172 [M−H]−; HPLC (Rt): 2.57 min (Method N).

Step 2: To A-27.4 (0.61 g, 3.50 mmol) in absolute EtOH (10 mL) at 0° C. is added NaOH (8N aq. solution, 4.50 mL, 35.0 mmol) and the reaction is heated at 100° C. for 4 h. The reaction mixture is concentrated, the aq. phase washed with Et2O, and the pH adjusted to pH4 using HCl (4N aq. solution). The aq. phase is concentrated and the remaining solids treated with a mixture of DCM/MeOH=9/1, the mixture is filtered to remove insoluble solids and the filtrate is concentrated to afford 0.7 g of A-27. ES+/−: 191 [M+H]+; HPLC (Rt): 0.58 min (Method Q).

2-[1,2,3]Triazol-2-yl-nicotinic acid A-28

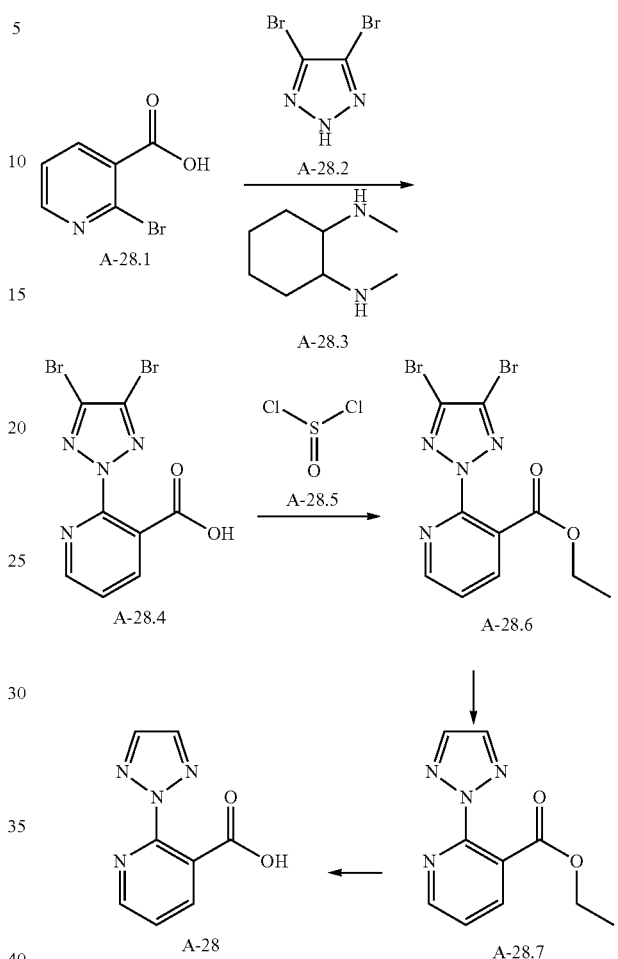

Step 1: Cs2CO3 (2.42 g, 7.43 mmol) is added to a stirred solution of A-28.2 (1.68 g, 7.43 mmol) in dry DMF (10 mL). The mixture is stirred for 10 min before A-28.1 (1.00 g, 4.95 mmol), CuI (56.6 mg, 0.30 mmol) and A-28.3 (63.4 µL, 0.45 mmol) are added and the reaction is heated to 110° C. by microwave irradiation and stirred for 30 min. After cooling, the mixture is concentrated, poured into water and extracted with Et2O. The organic phase is dried and concentrated to give the crude product which is purified by flash column chromatography on silica gel (using a solvent gradient from n-hexane/EA=8/2 to EA 100%) to provide 1.5 g of A-28.4. ES+/−: 348 [M+H]+; HPLC (Rt): 0.57 min (Method P).

Step 2: To A-28.4 (2.20 g, 5.00 mmol) in absolute EtOH (10 mL), A-28.5 (1.14 mL, 15.7 mmol) is added dropwise and the mixture is heated at reflux overnight. After removal of the solvents the residue is dissolved in DCM and the organic phase washed with NaHCO3 (aq. sat. solution). The organic phase is separated, dried and concentrated. The crude product is purified by flash column chromatography on silica gel (using an isocratic elution with the mixture of solvent cyclohexane/EA=85/15) to afford 1.6 g A-28.6 ES+/−: 377 [M+H]+; HPLC (Rt): 1.18 min (Method P).

Step 3: To A-28.6 (1.60 g, 4.30 mmol) in EtOH (20 mL) is added TEA (1.20 mL, 8.50 mmol) and Pd/C (10%, 0.40 g, 0.40 mmol) and the reaction is stirred under an atmosphere of hydrogen (2 bar) for 3 h. The mixture is filtered through a celite pad and is concentrated. The residue is taken up in DCM and washed with citric acid (10% aq. solution). The organic phase is dried and concentrated to afford 0.9 g of A-28.7. ES+/−: 219 [M+H]+; HPLC (Rt): 0.75 min (Method U).

Step 4: To a mixture of A-28.7 (1.60 g, 6.60 mmol) in water (15 mL) and THF (25 mL) is added LiOH H$_2$O (0.83 g, 20.0 mmol) and the mixture is stirred at RT for 5 h. The solvent is removed and the aq. phase is acidified to 0° C. with HCl (4N aq. solution). The mixture is concentrated and the residue is treated with DCM/MeOH=9/1. Solids are filtered off and the residue is concentrated to afford 0.8 g of A-28. ES+/−: 191 [M+H]+; HPLC (Rt): 0.59 min (Method Q).

4-[1,2,3]Triazol-2-yl-nicotinic acid A-29

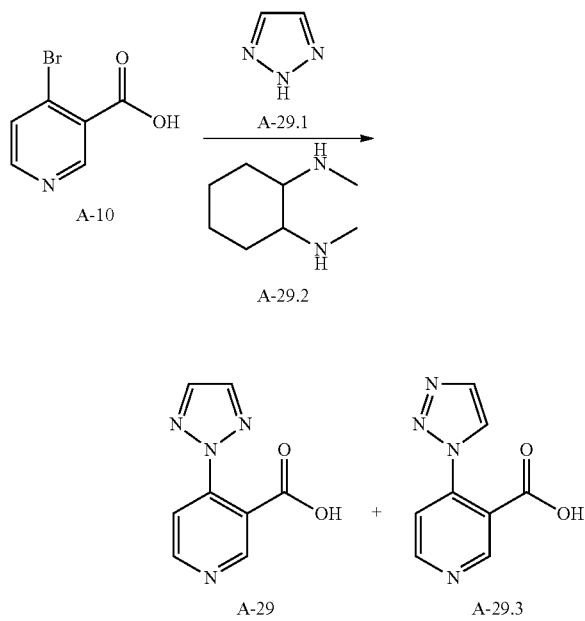

To a stirred solution of A-29.1 (0.50 g, 7.50 mmol) in 1.4-dioxane (20 mL) and H$_2$O (0.4 mL) is added K$_2$CO$_3$ (1.40 g, 9.90 mmol). The mixture is stirred for 10 min then A-10 (1.00 g, 5.00 mmol), CuI (56.0 mg, 0.30 mmol) and A-29.2 (70.0 μL, 0.40 mmol) are added and the reaction is heated at 110° C. by microwave irradiation for 60 min. After cooling, the mixture is poured into water and extracted with Et$_2$O. The aq. phase is acidified with HCl (4N aq. solution) and concentrated. The residue is treated with DCM/MeOH=8/2, solids are filtered off and the residue is concentrated to give the crude product which is purified by flash column chromatography on silica gel (using a gradient DCM/MeOH/HCOOH=98/1.8/0.2) to afford 0.4 g of A-29 ES+/−: 191 [M+H]+; HPLC (Rt): 0.25 min (Method P) and 0.30 g A-29.3 ES+/−: 191 [M+H]+; HPLC (Rt): 0.24 min (Method P).

5-Fluoro-2-(5-methyl-[1,3,4]oxadiazol-2-yl)-nicotinic acid A-30

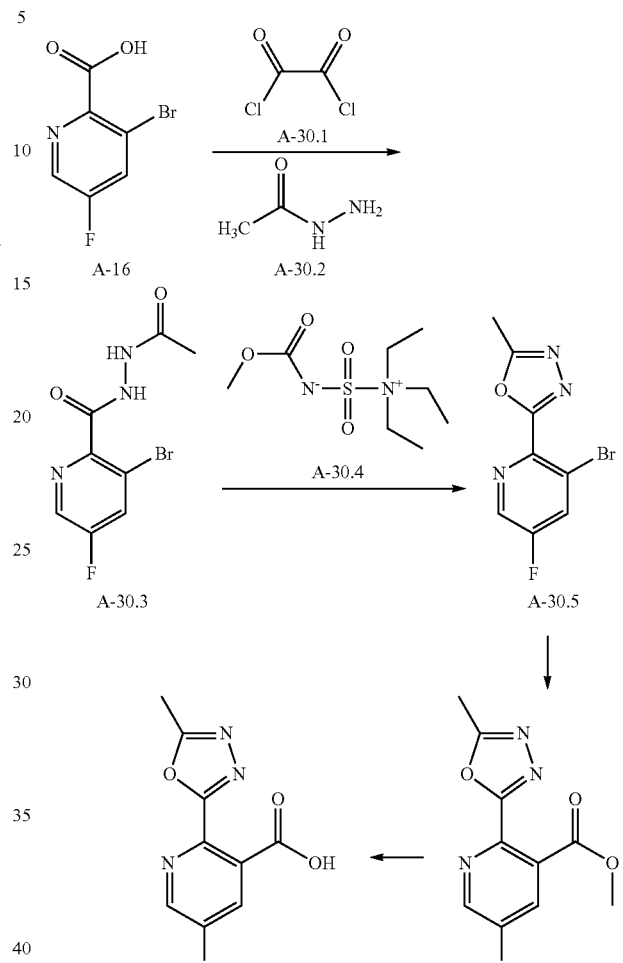

Step 1: To a mixture of A-16 (9.70 g, 40.0 mmol) in DMF (50 mL) and DCM (100 mL) is added dropwise A-30.1 (6.20 g, 50.0 mmol) and the mixture is stirred at RT for 30 min. A-30.2 (4.90 g, 70.0 mmol) is added and the reaction is stirred at RT for 30 min. The mixture is concentrated and the residue is purified by flash column chromatography on silica gel (using a solvent gradient from petroleum ether/EA=1/0 to 5/1) to provide 4.0 g of A-30.3. APCl+/−: 276 [M+H]+; HPLC (Rt): 0.52 min (Method N).

Step 2: To a mixture of A-30.3 (3.40 g, 10.0 mmol) in dry DCM (40 mL) is added A-30.4 (5.90 g, 20.0 mmol) and the reaction stirred at RT overnight. The mixture is concentrated and the residue is purified by flash column chromatography on silica gel (using a solvent gradient from petroleum ether/EA=I/O to 5/1) to provide 2.0 g of A-30.5. APCl+/−: 258 [M+H]+; HPLC (Rt): 2.58 min (Method N).

Step 3: To a mixture of A-30.5 (2.20 g, 10.0 mmol) in MeOH (300 mL) is added TEA (2.60 g, 30.0 mmol) followed by Pd(dppf)Cl$_2$.DCM (1.50 mg, 0.02 mmol). The mixture is heated to 50° C. under an atmosphere of CO (50 psi) and stirred for 16 h, then concentrated and the residue is purified by flash column chromatography on silica gel (using a solvent gradient from petroleum ether/EA=1/0 to 5/1) to provide 1.4 g of A-30.6.

Step 4: To a mixture of A-30.6 (1.20 g, 5.00 mmol) in THF (12 mL) and H₂O (1.0 mL) is added NaOH (0.40 g, 10.0 mmol) and the reaction is heated to 70° C. and stirred for 4 h. After cooling, the mixture is concentrated and the aq. phase is acidified with HCl (4N aq. solution) to adjust the pH to <6. The obtained solid is filtered and dried to provide 0.9 g of A-30. ES+/−: 224 [M+H]⁺; HPLC (Rt): 1.89 min (Method V).

5-Methoxy-2-[1,2,3]triazol-2-yl-nicotinic acid A-31

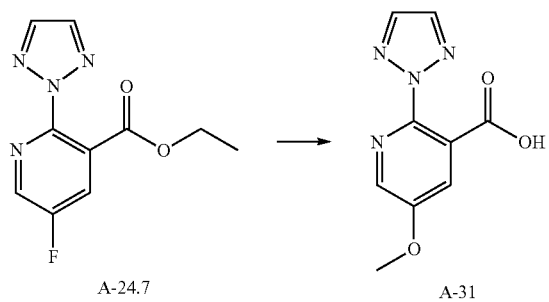

To a solution of A-24.7 (1.10 g, 2.80 mmol) in MeOH (10 mL) are added sodium methoxide (25 wt. % solution in MeOH, 3.70 mL, 14.0 mmol) and the mixture is heated at reflux for 5 h. Water and HCl (4M in dioxane) are added. The mixture is then concentrated. The residue is treated with 30 mL of DCM/MeOH 90/10. Salts are filtered off and the filtrate concentrated to afford 0.5 g of A-31. ES+/−: 221 [M+H]⁺; HPLC (Rt): 0.64 min (Method Q).

3-[1,2,3]Triazol-2-yl-isonicotinic acid A-32

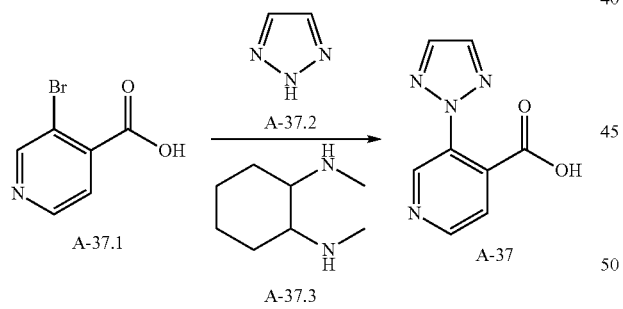

To a mixture of A-37.1 (0.20 g, 1.00 mmol) in dry DMF (3.0 mL) is added under argon atmosphere A-37.2 (114 µL, 2.00 mmol), CuI (9.50 mg, 0.05 mmol), A-37.3 (28.0 µL, 0.20 mmol) and Cs₂CO₃ (0.65 g, 2.00 mmol) and the reaction is heated to 100° C. and stirred for 1.5 h. After cooling, the mixture is acidified with HCl (1N aq. solution) and extracted with EA. The organic phase is dried and concentrated. The aq. phase is concentrated and the residue is treated with DCM/MeOH. Solids are filtered off and the residue is concentrated. Combined residues from the aq. and organic phases are purified by preparative HPLC (using a solvent gradient H₂O+0.075% TFA with 5-35% ACN) to afford 95 mg A-37 ES+/−: 191 [M+H]⁺; HPLC (Rt): 0.26 min (Method X).

Amine Intermediates

Ethyl-[(S)-1-methyl-2-(5-trifluoromethyl-pyridin-2-yloxy)-ethyl]-amine B-1

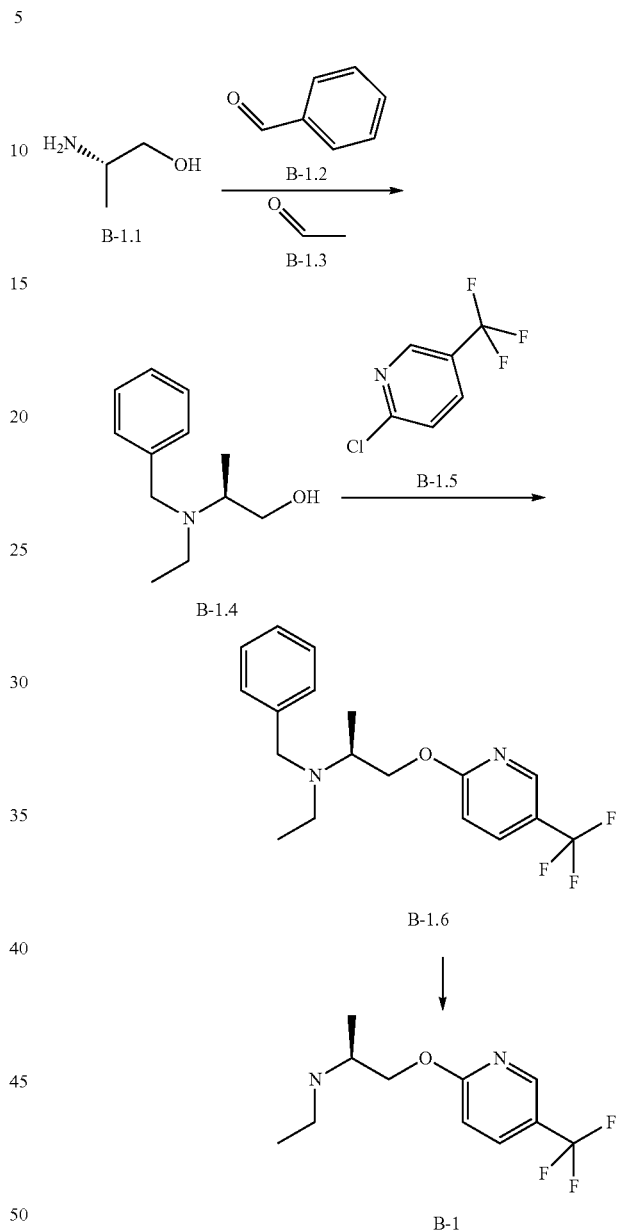

Step 1: A mixture of B-1.1 (5.00 g, 66.0 mmol), B-1.2 (6.80 mL, 66.0 mmol) in THF (180 mL) is stirred at RT for 1 h. NaBH(OAc)₃ (44.0 g, 0.20 mol) is added at 0° C. and the reaction is stirred at RT for 30 min. B-1.3 (11.0 mL, 0.20 mol) in THF (20 mL) is added dropwise within 10 min at 0° C. and the mixture is stirred at RT overnight. Additional B-1.3 (10 mL) is added and the reaction is stirred at RT for 3 h. The precipitate is filtered and washed with THF and DCM. NaHCO₃ (sat. aq. solution, 200 mL) and solid NaHCO₃ is added until gas formation subsides. The water phase is extracted with DCM, dried and concentrated to provide 12 g of compound B-1.4. ESI-MS: 194 [M+H]⁺; HPLC (Rt): 1.13 min (Method E).

Step 2: To a mixture of B-1.4 (2.75 g, 15.0 mmol) and potassium tert-butoxide (3.50 g, 31.0 mmol) in dry dioxane (80 mL) under a nitrogen atmosphere is added B-1.5 (2.80 g, 15.0 mmol). The mixture is heated to 60° C. and stirred for 2 h, poured into water and extracted with EA. The organic phase is extracted with NaCl (sat. aq. solution), dried and concentrated to provide 4.7 g of compound B-1.6. ESI-MS: 339 [M+H]⁺; HPLC (Rt): 1.31 min (Method F).

Step 3: To a mixture of B-1.6 (4.70 g, 12.0 mmol) in MeOH (40 mL) Pd/C (0.50 g) is added. The reaction is stirred at RT and under an atmosphere of hydrogen (3.5 bar) for 2 h. The catalyst is filtered off and the solvent is removed to provide 3.1 g of B-1. ESI-MS: 249 [M+H]⁺; HPLC (Rt): 1.04 min (Method F); ¹H NMR (300 MHz, DMSO-d₆) δ ppm 0.96-1.03 (m, 3 H), 1.06 (d, 3 H), 2.60 (m, 2 H), 2.99 (m, 1 H), 4.13 (dd, 1 H), 4.24 (dd, 1 H), 7.01 (d, 1 H), 8.05 (dd, 1 H), 8.56 (m, 1 H).

Ethyl-[(S)-2-(3-fluoro-5-trifluoromethyl-pyridin-2-yloxy)-1-methyl-ethyl]-amine B-2

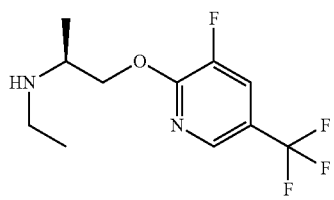

B-2

B-2 is prepared in analogy to the above described procedure with a modifation of step 3: for the elimination of the protective group Pd(OH)₂ is used instead of Pd/C. ESI-MS: 357 [M+H]⁺; HPLC (Rt): 1.32 min (Method F); ¹H NMR (400 MHz, DMSO-d₆) δ ppm 0.98-1.01 (t, 3 H); 1.08 (d, 3 H); 2.61 (m, 1 H) 2.51-2.56 (m, 2 H); 3.03 (m, 1 H); 4.21-4.26 (dd, 1 H); 4.33-4.37 (dd, 1 H); 8.19 (d, 1 H); 8.4 (m, 1 H).

[(S)-2-(5-Chloro-pyridin-2-yloxy)-1-methyl-ethyl]-ethyl-amine hydrochloride B-3

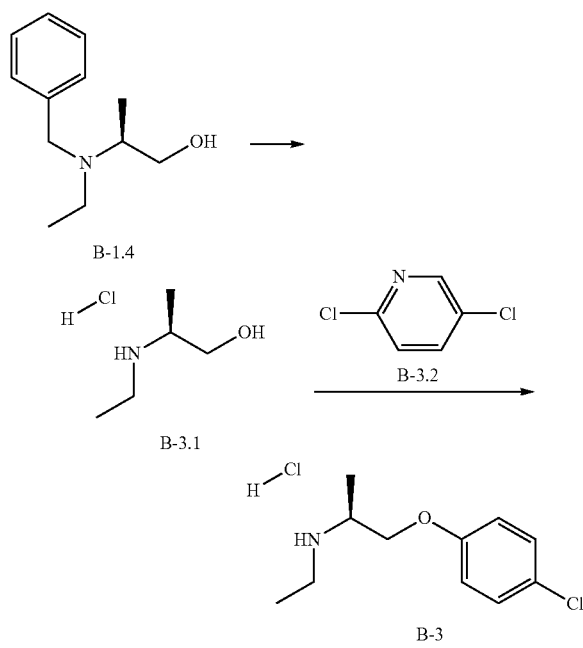

Step 1: To a mixture of B-1.4 (9.01 g, 46.62 mmol) in MeOH (200 mL) is added Pd/C (0.90 g) and the reaction is stirred at RT under an atmosphere of hydrogen (4 bar) for 4 h. The catalyst is filtered off. HCl (4M in dioxane, 14.0 mL, 56.0 mmol) is added and the resulting mixture is concentrated to provide 6.00 g of B-3.1. ESI-MS: 104 [M+H]⁺; HPLC (Rt): 0.20 min (Method L).

Step 2: To B-3.1 (2.60 g, 18.6 mmol) in dry DMF (100 mL) at 5° C. and under a nitrogen atmosphere is added NaH (3.00 g, 75.0 mmol) and the mixture is stirred at RT for 1 h. B-3.2 (4.24 g, 28.6 mmol) is added and the mixture is heated to 60-70° C. and stirred for 2 h. The reaction is treated with cold citric acid (10% aq. solution) and extracted with Et₂O. The aq. phase is separated, treated with NH₄OH until pH 10 and extracted with DCM. The organic layer is dried and concentrated. The residue is dissolved in EA and treated with HCl/Et₂O at 0° C. The solid is filtered off, washed with EA and n-hexane to provide 3.50 g of B-3. ESI-MS: 215 [M+H]⁺; HPLC (Rt): 3.17 min (Method O); ¹H NMR (500 MHz, DMSO-d₆) δ ppm 1.24 (t, 3 H), 1.34 (d, 3 H), 2.95-3.08 (m, 2 H), 3.59 (m, 1 H), 4.39-4.49 (m, 2 H), 6.91-6.97 (m, 1 H), 7.86 (dd, 1 H), 8.23 (d, 1 H), 9.09-9.23 (br. s., 2 H).

Ethyl-[(S)-1-methyl-2-(5-trifluoromethyl-pyrimidin-2-yloxy)-ethyl]-amine hydrochloride B-4

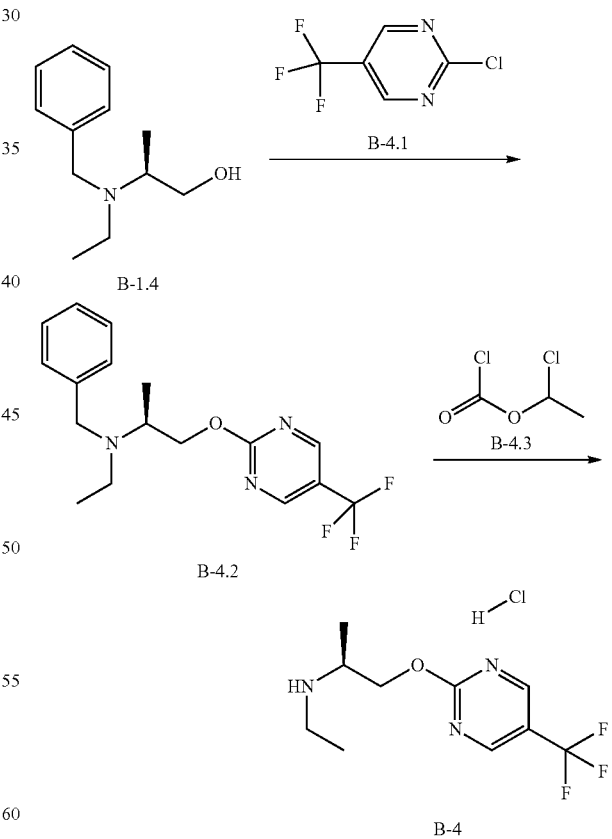

Step 1: To a mixture of B-1.4 (3.50 g, 18.1 mmol) in dry dioxane (60 mL) under a nitrogen atmosphere is added portionwise potassium tert-butoxide (4.47 g, 39.8 mmol) and the mixture is stirred for 15 min before B-4.1 (3.64 g, 19.9 mmol) is added. The mixture is heated to 60° C. and stirred overnight at RT and then concentrated. Water is added and the mixture is extracted with EA. The organic phase is dried and concentrated. The crude product is purified by flash column chromatography on silica gel (using a solvent gradient from 100% cyclohexane to 85% cyclohexane and 15% EA) to provide 1.3 g of B-4.2. ESI-MS: 340 [M+H]⁺; HPLC (Rt): 1.47 min (method P)

Step 2: To a mixture of B-4.2 (1.30 g, 3.45 mmol) in dry 1,2-dichloroethane (15 mL) at 0° C. and under a nitrogen atmosphere is added B-4.3 (0.45 mL, 4.14 mmol). The mixture is heated to reflux and stirred for 4 h. 15 mL of MeOH is added and the reaction is heated to 60° C. and stirred for 1 h. The solvent is evaporated and the crude mixture is purified by flash column chromatography on silica gel (using a solvent gradient from 100% DCM to 94% DCM and 6% MeOH+0.6% NH₃). The obtained compound is taken up into EA and HCl (2M aq. solution, 1.72 mL) is added under stirring. The solvent is removed and the residue obtained is triturated with Et₂O and filtered to give 0.4 g of B-4. ESI-MS: 250 [M+H]⁺; HPLC (Rt): 2.18 min (method N), ¹H NMR (400 MHz, DMSO-d₆) δ ppm 1.23 (t, J=7.24 Hz, 3 H) 1.36 (d, J=7.04 Hz, 3 H) 3.05 (dd, J=7.04, 3.91 Hz, 2 H) 3.62-3.72 (m, 1 H) 4.52-4.71 (m, 2 H) 9.03 (br. s., 2 H) 9.12 (d, J=0.78 Hz, 2 H)

Ethyl-[(S)-1-methyl-2-(5-trifluoromethyl-pyrazin-2-yloxy)-ethyl]-amine hydrochloride B-5

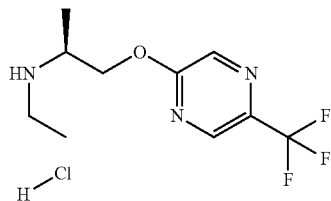

B-5

B-5 is prepared in analogy to the above described procedure. ESI-MS: 250 [M+H]⁺; HPLC (Rt): 0.71 min (Method P); ¹H NMR (300 MHz, DMSO-d₆) δ ppm 1.22 (t, 3 H), 1.35 (d, 3 H), 3.04 (m, 2 H), 3.67 (m, 1 H), 4.53 (dd, 1 H), 4.63 (dd, 1 H), 8.52 (s, 1 H), 8.79 (s, 1 H), 8.65-9.00 (br s, 2 H).

(S)-1-Methyl-2-(5-trifluoromethyl-pyridin-2-yloxy)-ethylamine B-6

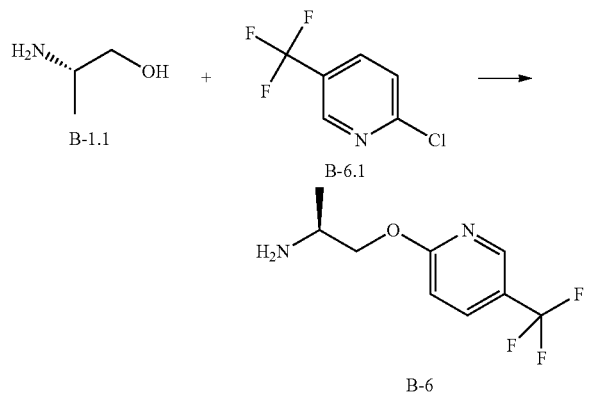

To a mixture of B-1.1 (0.80 g, 11.0 mmol) in dry DMF (5.0 mL) under a nitrogen atmosphere and at 5° C. is added portionwise NaH (0.50 g, 13.0 mmol). The mixture is stirred at RT for 1 h. B-6.1 (2.30 g, 13.0 mmol) is added and the reaction is stirred at RT for 2 h. H₂O is added and extracted with EA, the organic phase is separated, dried and concentrated. The crude product is purified by flash column chromatography on silica gel (using a solvent gradient from DCM 100% to DCM/MeOH=9/1) to afford 1.6 g of B-6. ESI-MS: 221 [M+H]⁺; HPLC (Rt): 0.66 min (Method P); ¹H NMR (500 MHz, DMSO-d₆) δ ppm 1.03-1.09 (d, 3 H), 3.16-3.23 (m, 1 H), 4.07-4.16 (m, 2 H), 7.02 (d, 1 H), 8.06 (dd, 1 H), 8.54-8.57 (m, 1 H).

Alcohol Intermediates

3-[1,2,3]Triazol-2-yl-pyridine-2-carboxylic acid ethyl-((S)-2-hydroxy-1-methyl-ethyl)-amide C-1

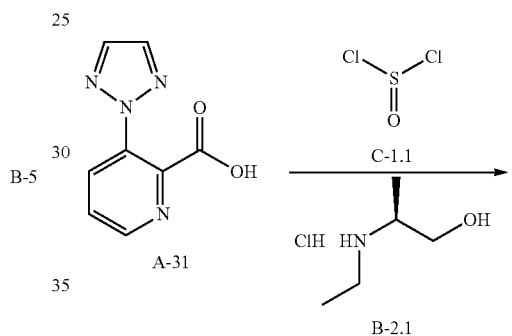

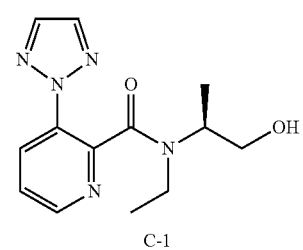

C-1

Step 1: To a mixture of A-31 (0.41 g, 2.16 mmol) in toluene (6.0 mL) is added dropwise C-1.1 (0.17 mL, 2.38 mmol). A drop of DMF is added and the mixture is heated to 100° C. and stirred for 3 h. The solvent is evaporated, the residue is taken up in dry DCM (10 mL) and a solution of B-2.1 (0.90 mL, 6.50 mmol) in dry DCM (5.0 mL) is added dropwise at 0° C. The reaction is stirred at RT overnight. Water is added and the organic layer is separated, washed with citric acid (10% aq. solution) and with KHCO₃ (aq. solution). The organic phase is dried and concentrated. The crude product is purified by flash column chromatography on silica gel (using a solvent gradient from n-Hexane/EA=8/2 to 100% EA) to provide 45 mg of C-1. ESI-MS: 276 [M+H]⁺; HPLC (Rt): 1.76 (Method R).

N-Ethyl-5-fluoro-N—((S)-2-hydroxy-1-methyl-ethyl)-2-pyrimidin-2-yl-nicotinamide C-2

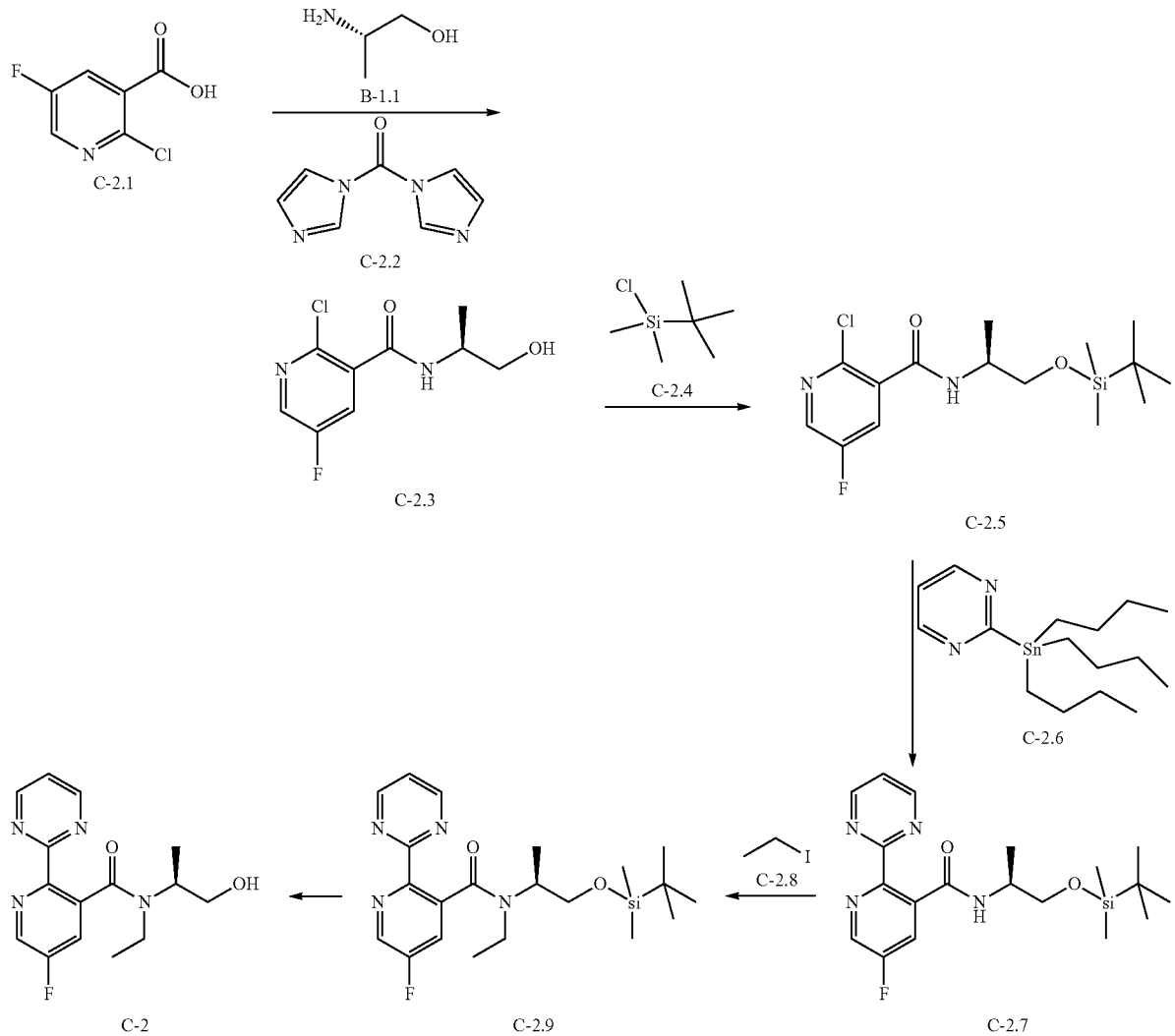

Step 1: To a mixture of C-2.1 (5.00 g, 29.0 mmol) and B-1.1 (2.30 g, 31.0 mmol) in dry DCM (80 mL) is added under a nitrogen atmosphere C-2.2 (5.10 g, 31.0 mmol). The mixture is stirred at RT overnight, then diluted with DCM and NH₄Cl (sat. aq. solution) is added. The organic layer is separated, dried and concentrated. The residue is purified by flash column chromatography on silica gel (using the eluent EA/n-Hexane/MeOH=70/30/1) to afford 3.0 g of C-2.3 ESI-MS: 233 [M+H]⁺; HPLC (Rt): 0.57 (Method P).

Step 2: To a stirred solution of C-2.3 (2.90 g, 13.0 mmol) and imidazole (0.94 g, 13.8 mmol) in dry DCM (70 mL) is added C-2.4 (2.07 g, 13.7 mmol). The mixture is stirred at RT for 2 h, water is then added, the organic layer is separated, washed with NH₄Cl (sat. aq. solution), dried and concentrated to afford 4.0 g of C-2.5 ESI-MS: 347 [M+H]⁺; HPLC (Rt): 1.42 (Method P).

Step 3: C-2.6 (0.20 mL, 0.63 mmol) is added to a stirred mixture of C-2.5 (200 mg, 0.58 mmol), CuI (5.00 mg, 0.03 mmol) and Pd(PPh₃)₄ (33.0 mg, 0.03 mmol) in dry 1,2-dimethoxyethane at RT. The mixture is degassed by nitrogen and the reaction is heated by microwave irradiation at 120° C. for 60 min. After cooling to RT, the mixture is treated with water and extracted with EA. The organic layer is separated, dried and concentrated. The residue is purified by flash column chromatography on silica gel (using an eluent of DCM/MeOH 100/3) to afford 200 mg of C-2.7 ESI-MS: 391 [M+H]⁺; HPLC (Rt): 1.23 (Method P).

Step 4: NaH (30.0 mg, 0.75 mmol) is added to a stirred mixture of C-2.7 (200 mg, 0.46 mmol) in dry DMF (5.0 mL) at 5° C. under N₂. After 30-40 min C-2.8 (85.0 mg, 0.54 mmol) is added at RT. The mixture is stirred for 3 h. The mixture is treated with water and extracted with EA. The organic layer is separated, washed with water, dried and concentrated. The residue is purified by flash column chromatography on silica gel (using an eluent of EA/MeOH 100/2) to afford 70 mg of C-2.9 ESI-MS: 419 [M+H]⁺; HPLC (Rt): 1.37 (Method P).

Step 5: TBAF (1 M in THF, 0.15 mL, 0.15 mmol) is added to a stirred mixture of C-2.9 (60.0 mg, 0.14 mmol) in dry THF (3.0 mL) under a nitrogen atmosphere at 0° C. After 1 h the solvent is evaporated. The residue is treated with DCM and washed with water. The organic layer is separated, dried and concentrated. The residue is purified by flash column chromatography on silica gel (using an eluent of EA/MeOH 100/3) to afford 30 mg of C-2.10 ESI-MS: 305 [M+H]+; HPLC (Rt): 0.60 (Method P).

Amide Intermediates

3-Bromo-5-methyl-pyridine-2-carboxylic acid ethyl-[(S)-1-methyl-2-(5-trifluoromethyl-pyridin-2-yloxy)-ethyl]-amide D-1

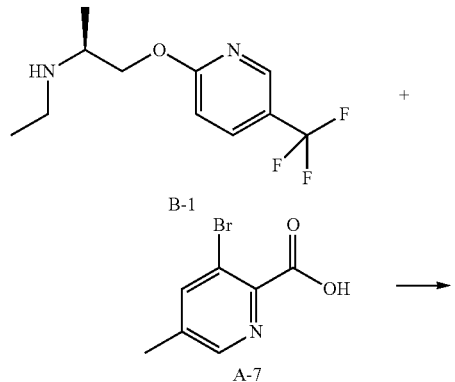

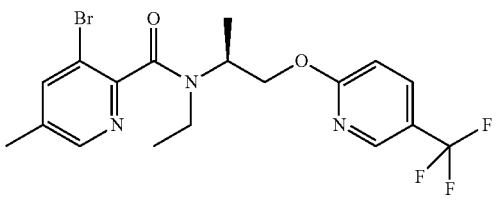

D-1

To a mixture of A-7 (104 mg, 0.50 mmol) and B-1 (100 mg, 0.40 mmol) in dry ACN (3.0 mL) is added DIPEA (209 µL, 1.20 mmol) and CIP (146 mg, 0.52 mmol) and the mixture is stirred at RT overnight. The reaction is diluted with DMF and H₂O and directly purified by HPLC-MS (using a solvent gradient H₂O/ACN with NH₄OH) to afford 100 mg of D-1. ESI-MS: 446 [M+H]+; HPLC (Rt): 1.12 min (Method F).

The following examples are prepared in analogy to the above described procedure using the corresponding acid (see Acid Intermediates) and amine (see Amine Intermediates) as described before.

| Amide | Structure | ESI-MS [M + H]+ | HPLC (Rt) [min] | HPLC method |
|---|---|---|---|---|
| D-2 | ![structure] | 418 | 1.15 | F |
| D-3 | ![structure] | 402 | 1.13 | F |
| D-4 | ![structure] | 432 | 1.07 | F |
| D-5 | ![structure] | 432 | 1.08 | F |

-continued

| Amide | Structure | ESI-MS [M + H]+ | HPLC (Rt) [min] | HPLC method |
|---|---|---|---|---|
| D-6 | 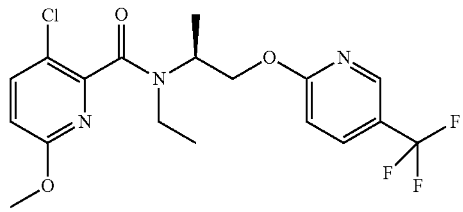 [SMILES: CCN(C(=O)c1nc(OC)ccc1Cl)[C@@H](C)COc1ccc(C(F)(F)F)cn1] | 418 | 1.15 | F |
| D-7 | 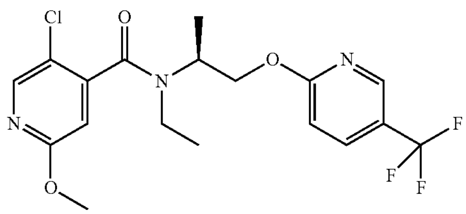 [SMILES: CCN(C(=O)c1cc(OC)ncc1Cl)[C@@H](C)COc1ccc(C(F)(F)F)cn1] | 418 | 1.14 | F |
| D-8 | 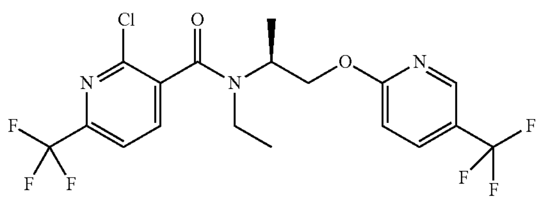 [SMILES: CCN(C(=O)c1ccc(C(F)(F)F)nc1Cl)[C@@H](C)COc1ccc(C(F)(F)F)cn1] | 456 | 1.17 | F |
| D-9 | 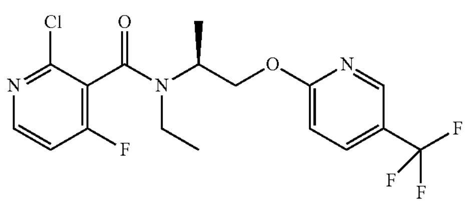 [SMILES: CCN(C(=O)c1c(F)ccnc1Cl)[C@@H](C)COc1ccc(C(F)(F)F)cn1] | 406 | 1.10 | F |
| D-10 | 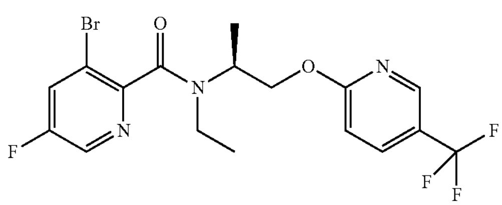 [SMILES: CCN(C(=O)c1ncc(F)cc1Br)[C@@H](C)COc1ccc(C(F)(F)F)cn1] | 450 | 1.11 | F |
| D-11 | 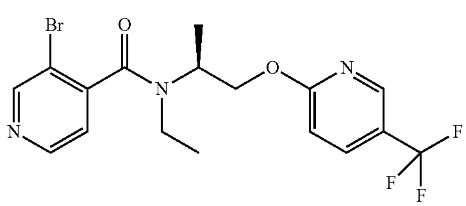 [SMILES: CCN(C(=O)c1ccncc1Br)[C@@H](C)COc1ccc(C(F)(F)F)cn1] | 432 | 1.07 | F |
| D-12 | 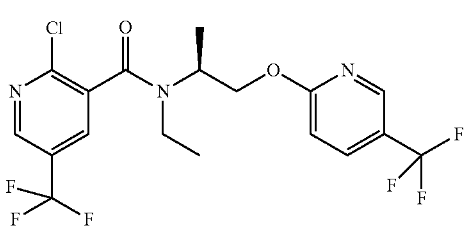 [SMILES: CCN(C(=O)c1cc(C(F)(F)F)cnc1Cl)[C@@H](C)COc1ccc(C(F)(F)F)cn1] | 456 | 1.16 | F |

| Amide | Structure | ESI-MS [M + H]+ | HPLC (Rt) [min] | HPLC method |
|---|---|---|---|---|
| D-13 | 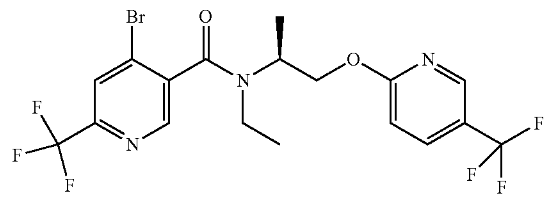 [SMILES: CCN(C(=O)c1cnc(C(F)(F)F)cc1Br)[C@@H](C)COc1ccc(C(F)(F)F)cn1] | 500 | 1.17 | F |
| D-14 | 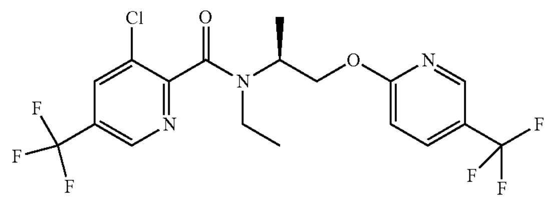 [SMILES: CCN(C(=O)c1ncc(C(F)(F)F)cc1Cl)[C@@H](C)COc1ccc(C(F)(F)F)cn1] | 456 | 1.17 | F |
| D-15 | 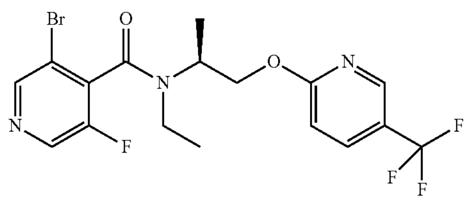 [SMILES: CCN(C(=O)c1c(F)cncc1Br)[C@@H](C)COc1ccc(C(F)(F)F)cn1] | 450 | 1.12 | F |
| D-16 | 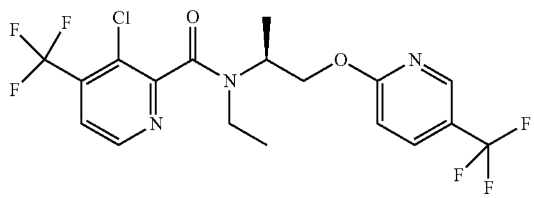 [SMILES: CCN(C(=O)c1nccc(C(F)(F)F)c1Cl)[C@@H](C)COc1ccc(C(F)(F)F)cn1] | 456 | 1.19 | F |

Preparation of Compounds of the Present Invention

Example 8

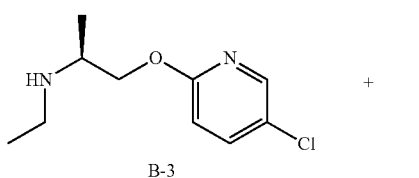

B-3

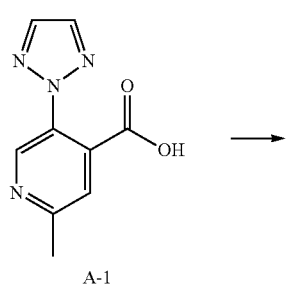

A-1

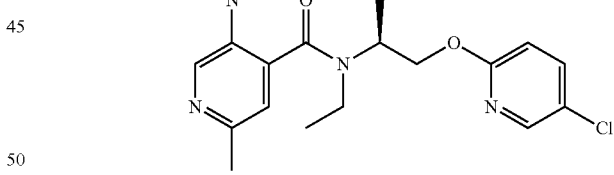

Example 8

To a mixture of A-1 (2.04 mg, 0.01 mmol) in ACN (90 µL) and DIPEA (5.20 µL, 0.03 mmol) is added B-3 (2.50 mg, 0.01 mmol) in ACN (100 µL). Then CIP (3.60 mg, 0.01 mmol) in ACN (50 µL) is added and the reaction is shaken overnight at RT. DMF (50 µL) and K₂CO₃ (3 M aq. solution, 15 µL) is added and the mixture is shaken for 20 min. The mixture is filtered through Alox, washed with DMF/MeOH=9/1 and concentrated to provide 2.2 mg of Example 8. ESI-MS: 423 [M+Na]⁺; HPLC (Rt): 0.88 min (Method S).

The following examples are prepared in analogy to the above described procedure using the corresponding acid (see Acid Intermediates) and amine (see Amine Intermediates) as described before.

| Example | Structure | ESI-MS [M + H]+ | HPLC (Rt) [min] | HPLC method |
|---|---|---|---|---|
| 11 | 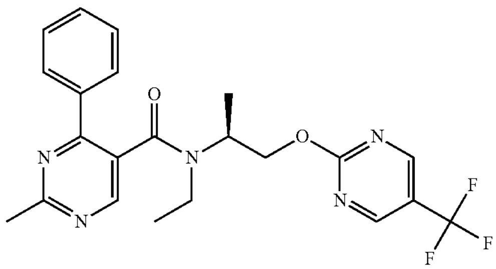 [SMILES: CCN(C(=O)c1cnc(C)nc1-c1ccccc1)[C@@H](C)COc1ncc(C(F)(F)F)cn1] | 468 [M + Na]+ | 0.40 | G |
| 12 | 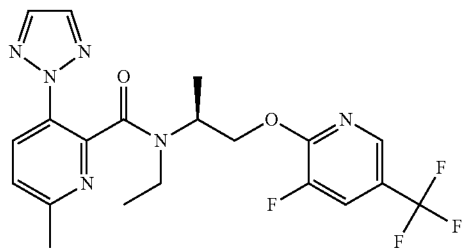 [SMILES: CCN(C(=O)c1nc(C)ccc1-n1nccn1)[C@@H](C)COc1ncc(C(F)(F)F)cc1F] | 453 | 0.90 | I |
| 15 | 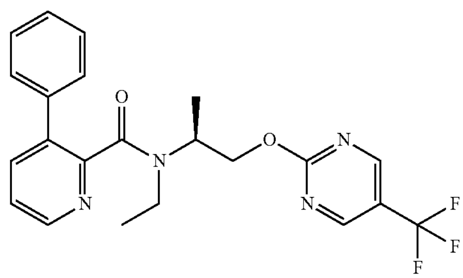 [SMILES: CCN(C(=O)c1ncccc1-c1ccccc1)[C@@H](C)COc1ncc(C(F)(F)F)cn1] | 453 [M + Na]+ | 0.85 | J |

Example 10

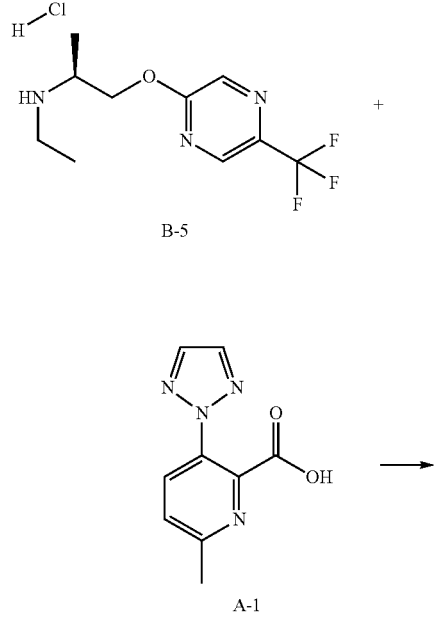

B-5

A-1

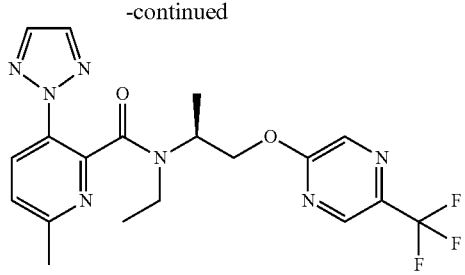

Example 10

To a mixture of A-1 (30.0 mg, 0.15 mmol) in ACN (1.0 mL) is added B-5 (35.0 mg, 0.12 mmol), DIPEA (64.0 µL, 0.37 mmol) followed by CIP (44.0 mg, 0.16 mmol) in ACN (1.0 mL) and the reaction is shaken for 1 h at RT. The mixture is diluted with DMF and directly purified by prep. HPLC-MS (using a solvent gradient $H_2O$/ACN with $NH_4OH$) to afford 40 mg of Example 10. ESI-MS: 436 [M+H]+; HPLC (Rt): 1.08 min (Method F).

The following examples are prepared in analogy to the above described procedure using the corresponding acid (see Acid Intermediates) and amine (see Amine Intermediates) as described before, adjusting the reaction times: overnight reaction for Examples 61; 90 min at 60° C. for Example 53; 3 h for Example 36, 42, 48, 52; 4 h for Example 25, 30; 5 h for Example 26, 57; 2 days for Example 51.

Examples 36, 42, 48, 52 are run in DMA instead of ACN.

For the synthesis of Examples 51, 30, 33, 36, 42, 48, 52 the work-up is done as follows: the reaction mixture is concentrated, DCM or EA is added and the organic phase is washed with water or with sat. NaHCO₃ solution and citric acid 10% solution. The organic phase is then dried and concentrated. The crude is purified by HPLC-MS or silica column.

| Example | Structure | ESI-MS [M + H]⁺ | HPLC (Rt) [min] | HPLC method |
|---------|-----------|-----------------|-----------------|-------------|
| 5 | 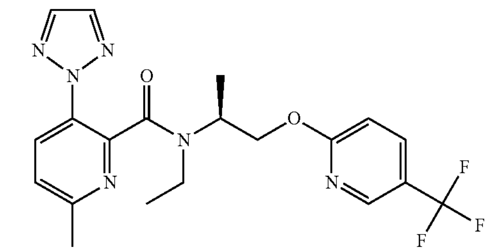 [SMILES: CCN(C(=O)c1nc(C)ccc1-n1nccn1)[C@@H](C)COc1ccc(C(F)(F)F)cn1] | 435 | 0.95 | G |
| 9 | 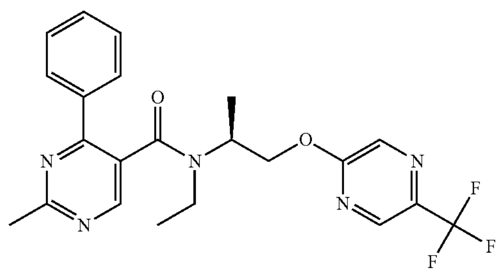 [SMILES: CCN(C(=O)c1cnc(C)nc1-c1ccccc1)[C@@H](C)COc1cnc(C(F)(F)F)cn1] | 446 | 0.89 | I |
| 22 | 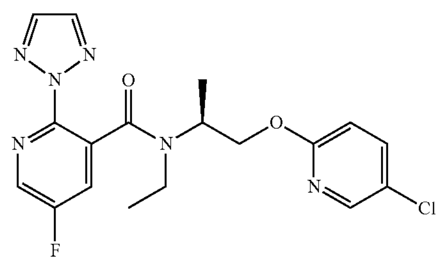 [SMILES: CCN(C(=O)c1cc(F)cnc1-n1nccn1)[C@@H](C)COc1ccc(Cl)cn1] | 427 [M + Na]⁺ | 3.39 | R |
| 26 | 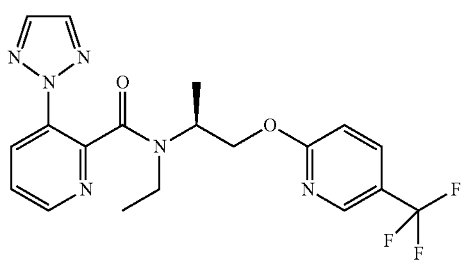 [SMILES: CCN(C(=O)c1ncccc1-n1nccn1)[C@@H](C)COc1ccc(C(F)(F)F)cn1] | 443 [M + Na]⁺ | 3.48 | R |
| 36 | 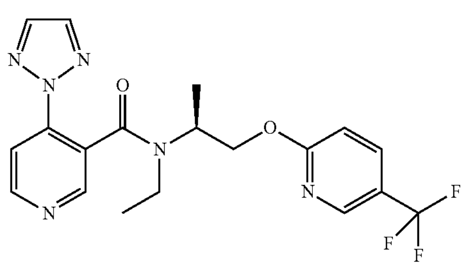 [SMILES: CCN(C(=O)c1cnccc1-n1nccn1)[C@@H](C)COc1ccc(C(F)(F)F)cn1] | 443 [M + Na]⁺ | 3.13 | R |

-continued

| Example | Structure | ESI-MS [M + H]+ | HPLC (Rt) [min] | HPLC method |
|---|---|---|---|---|
| 57 | 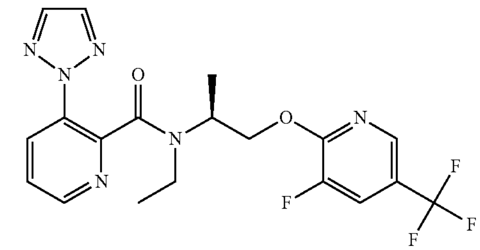 [SMILES: CCN(C(=O)c1ncccc1-n1nccn1)[C@@H](C)COc1ncc(C(F)(F)F)cc1F] | 461 [M + Na]+ | 3.58 | R |
| 61 | 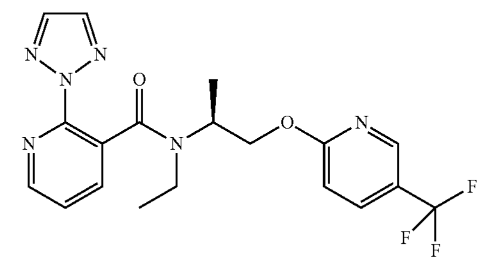 [SMILES: CCN(C(=O)c1cccnc1-n1nccn1)[C@@H](C)COc1ccc(C(F)(F)F)cn1] | 443 [M + Na]+ | 3.35 | R |
| 51 | 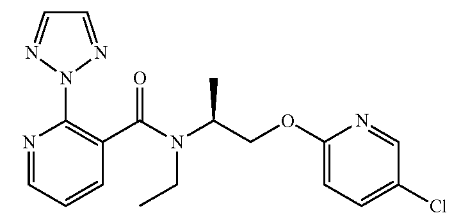 [SMILES: CCN(C(=O)c1cccnc1-n1nccn1)[C@@H](C)COc1ccc(Cl)cn1] | 409 [M + Na]+ | 3.11 | R |
| 30 | 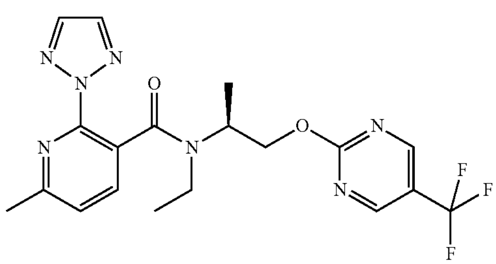 [SMILES: CCN(C(=O)c1ccc(C)nc1-n1nccn1)[C@@H](C)COc1ncc(C(F)(F)F)cn1] | 458 [M + Na]+ | 3.09 | R |
| 33 | 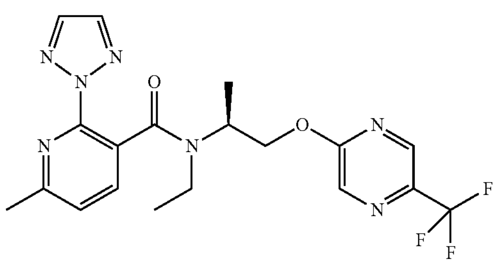 [SMILES: CCN(C(=O)c1ccc(C)nc1-n1nccn1)[C@@H](C)COc1cnc(C(F)(F)F)cn1] | 458 [M + Na]+ | 3.33 | R |
| 42 | 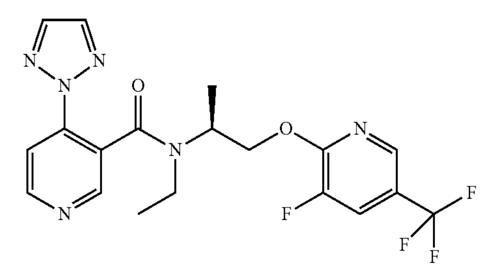 [SMILES: CCN(C(=O)c1cnccc1-n1nccn1)[C@@H](C)COc1ncc(C(F)(F)F)cc1F] | 439 | 3.38 | R |

-continued

| Example | Structure | ESI-MS [M + H]+ | HPLC (Rt) [min] | HPLC method |
|---------|-----------|-----------------|-----------------|-------------|
| 48 | 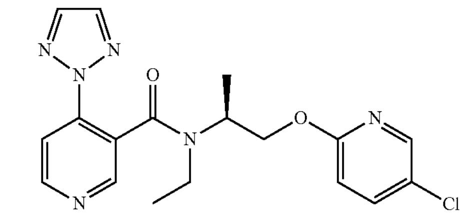 [SMILES: CCN(C(=O)c1cnccc1-n1nccn1)[C@@H](C)COc1ccc(Cl)cn1] | 409 [M + Na]+ | 3.16 | R |
| 17 | 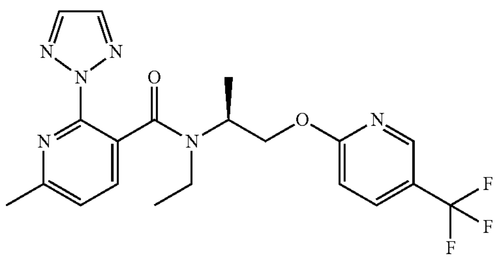 [SMILES: CCN(C(=O)c1ccc(C)nc1-n1nccn1)[C@@H](C)COc1ccc(C(F)(F)F)cn1] | 435 | 1.04 | F |
| 21 | 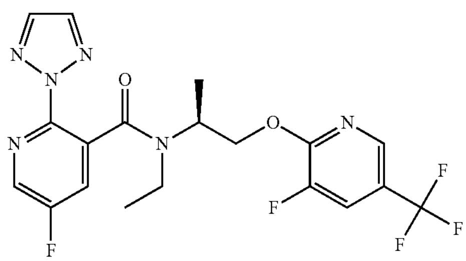 [SMILES: CCN(C(=O)c1cc(F)cnc1-n1nccn1)[C@@H](C)COc1ncc(C(F)(F)F)cc1F] | 457 | 1.08 | F |
| 23 | 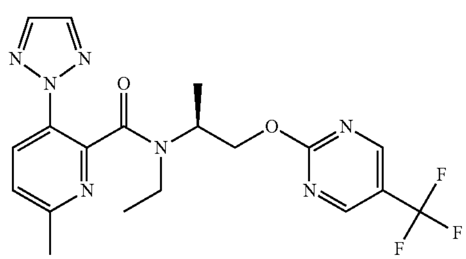 [SMILES: CCN(C(=O)c1nc(C)ccc1-n1nccn1)[C@@H](C)COc1ncc(C(F)(F)F)cn1] | 436 | 1.01 | F |
| 53 | 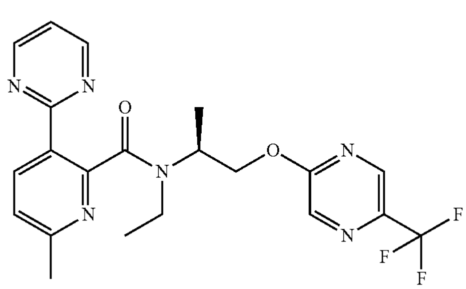 [SMILES: CCN(C(=O)c1nc(C)ccc1-c1ncccn1)[C@@H](C)COc1cnc(C(F)(F)F)cn1] | 447 | 1.08 | F |

Example 3

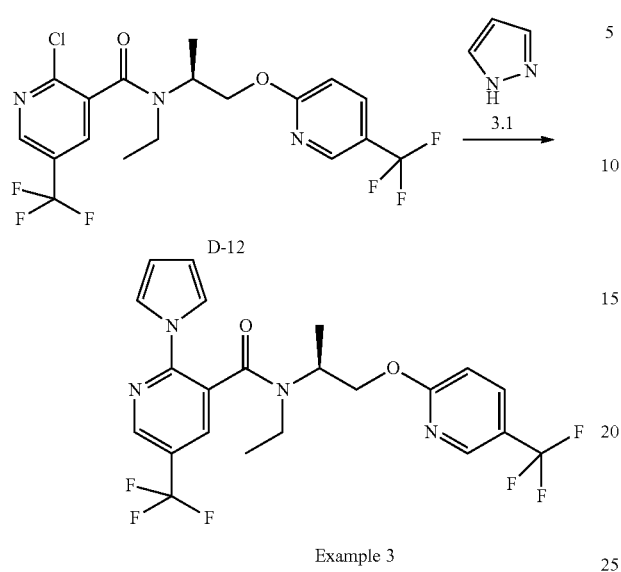

D-12 (40.0 mg, 0.09 mmol), 3.1 (59.8 mg, 0.88 mmol), K$_3$PO$_4$·nH$_2$O (40.4 mg, 0.18 mmol) and Cu$_2$O (1.26 mg, 0.01 mmol) are mixed together under a nitrogen atmosphere. The mixture is stirred at 150° C. for 30 min. DMF and MeOH are added and directly purified by prep. HPLC-MS (using a solvent gradient H$_2$O/ACN with NH$_4$OH). Fractions are then lyophilized to afford 23 mg of Example 3. ESI pos.+neg. (Loop-Inj.): 488 [M+H]$^+$; HPLC (Rt): 1.20 (Method F).

Example 6

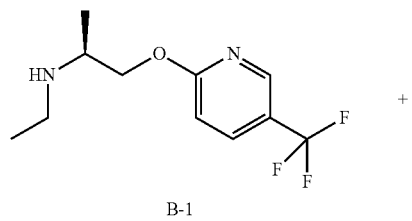

B-1

+

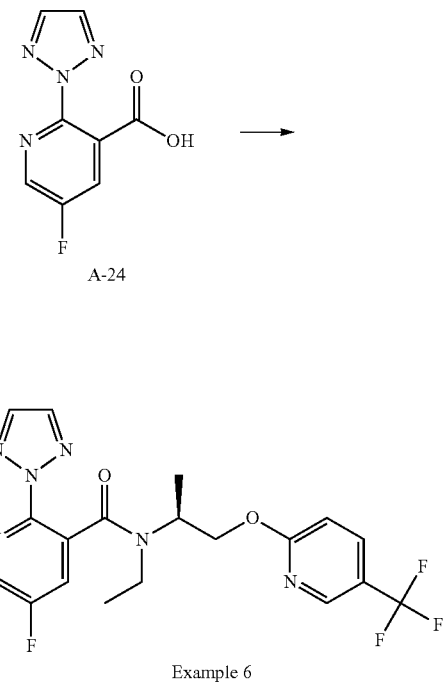

A-24

Example 6

To a mixture of B-1 (99.3 mg, 0.40 mmol), A-24 (125 mg, 0.60 mmol), DIPEA (208 μL, 1.20 mmol) dissolved in ACN (5.0 mL) is added CIP (145 mg, 0.52 mmol) and the reaction is stirred at RT for 1 h. The mixture is directly purified by prep. HPLC-MS (using a solvent gradient H$_2$O/ACN with NH$_4$OH). ACN is evaporated and the aq. phase is extracted with DCM. The organic phase is dried over MgSO$_4$ and concentrated to afford 164 mg of Example 6. ESI-MS: 439 [M+H]$^+$; HPLC (Rt): 1.04 min (Method F).

The following examples are prepared in analogy to the above described procedure using the corresponding acid (see Acid Intermediates) and amine (see Amine Intermediates) as described before, adjusting the reaction times to 2 h.

| Example | Structure | ESI-MS [M + H]$^+$ | HPLC (Rt) [min] | HPLC method |
|---|---|---|---|---|
| 72 | 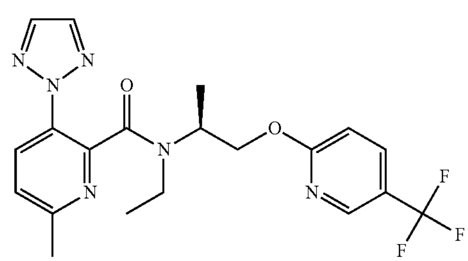 [SMILES: CCN(C(=O)c1nc(C)ccc1-n1nccn1)[C@@H](C)COc1ccc(C(F)(F)F)cn1] | 455 | 3.65 | R |

Example 20

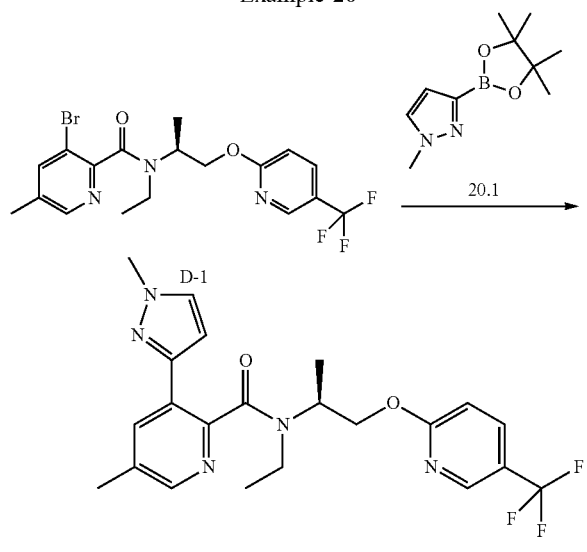

To a solution of D-1 (45.0 mg, 0.10 mmol) and 20.1 (42.0 mg, 0.20 mmol) in dry 1,4-dioxane (2.0 mL), Cs$_2$CO$_3$ (98.0 mg, 0.30 mmol) is added. The mixture is degassed with argon and Pd-PEPPSI-IPent catalyst (9.00 mg, 0.01 mmol) is added. The reaction is heated to 110° C. and stirred overnight. After cooling, the reaction is passed through a SPE Thiol cartridge, concentrated, then diluted with DMF and directly purified by HPLC-MS (using a solvent gradient H$_2$O/ACN with NH$_4$OH). Fractions are then lyophilized to afford 19 mg of Example 20. ESI pos.+neg. (Loop-Inj.): 448 [M+H]$^+$; HPLC (Rt): 1.07 (Method F).

The following examples are prepared in analogy to the above described procedure using the corresponding amide (see Amide Intermediates) as described before.

| Example | Structure | ESI pos. + neg. (Loop-Inj.) | HPLC (Rt) [min] | HPLC method |
|---|---|---|---|---|
| 32 | 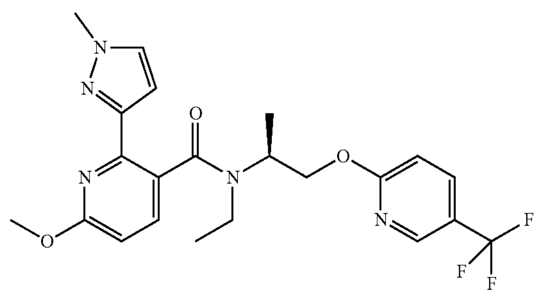 [SMILES: CCN(C(=O)c1ccc(OC)nc1-c1ccn(C)n1)[C@@H](C)COc1ccc(C(F)(F)F)cn1] | 464 | 1.12 | F |
| 27 | 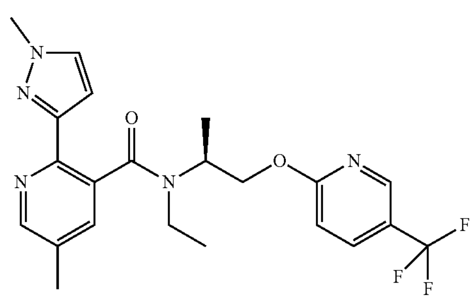 [SMILES: CCN(C(=O)c1cc(C)cnc1-c1ccn(C)n1)[C@@H](C)COc1ccc(C(F)(F)F)cn1] | 448 | 1.06 | F |
| 38 | 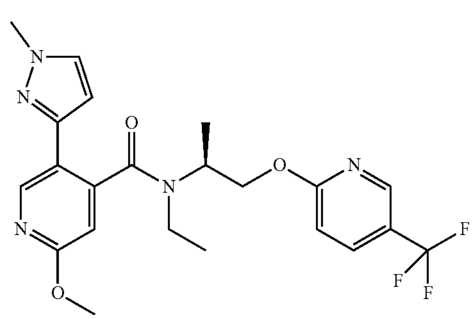 [SMILES: CCN(C(=O)c1cc(OC)ncc1-c1ccn(C)n1)[C@@H](C)COc1ccc(C(F)(F)F)cn1] | 464 | 1.09 | F |

| Example | Structure | ESI pos. + neg. (Loop-Inj.) | HPLC (Rt) [min] | HPLC method |
|---|---|---|---|---|
| 28 | 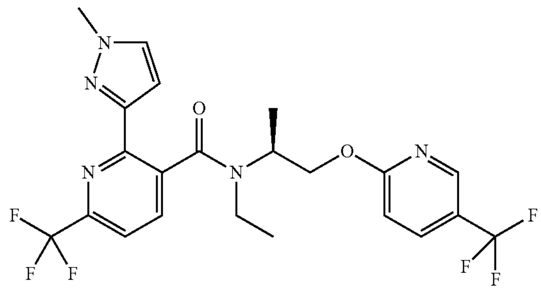 [SMILES: CCN(C(=O)c1ccc(C(F)(F)F)nc1-c1ccn(C)n1)[C@@H](C)COc1ccc(C(F)(F)F)cn1] | 502 | 1.16 | F |
| 58 | 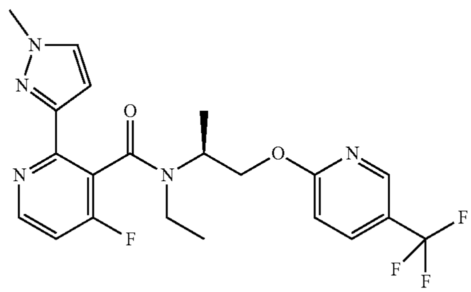 [SMILES: CCN(C(=O)c1c(F)ccnc1-c1ccn(C)n1)[C@@H](C)COc1ccc(C(F)(F)F)cn1] | 452 | 1.05 | F |
| 37 | 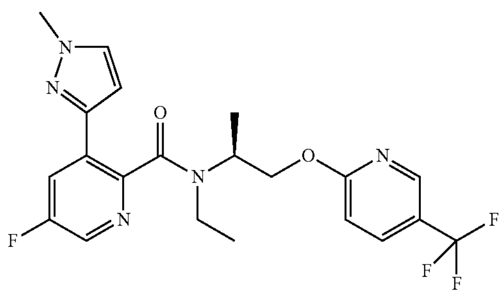 [SMILES: CCN(C(=O)c1ncc(F)cc1-c1ccn(C)n1)[C@@H](C)COc1ccc(C(F)(F)F)cn1] | 452 | 1.08 | F |
| 29 | 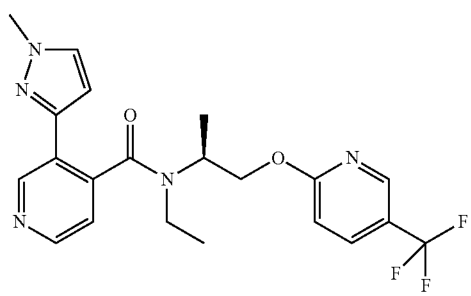 [SMILES: CCN(C(=O)c1ccncc1-c1ccn(C)n1)[C@@H](C)COc1ccc(C(F)(F)F)cn1] | 434 | 1.01 | F |
| 50 | 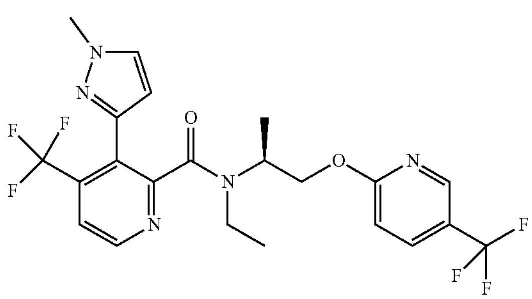 [SMILES: CCN(C(=O)c1nccc(C(F)(F)F)c1-c1ccn(C)n1)[C@@H](C)COc1ccc(C(F)(F)F)cn1] | 502 | 1.13 | F |

Example 34

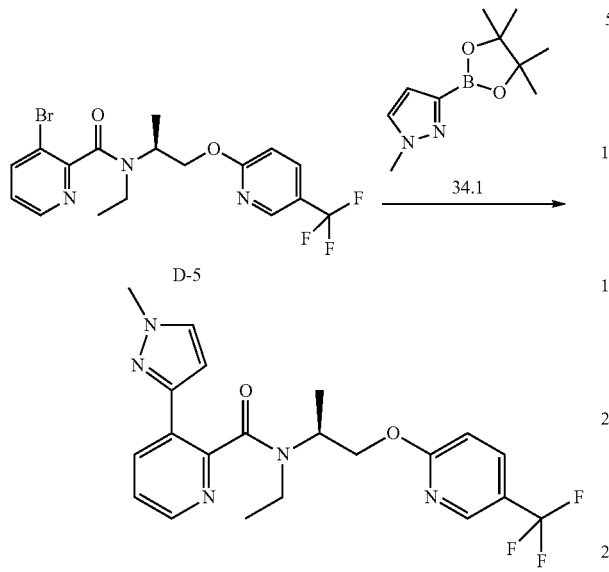

Example 34

To a solution of D-5 (30.0 mg, 0.07 mmol) and 34.1 (19.0 mg, 0.09 mmol) in dry 1,4-dioxane (2.0 mL), is added $K_2CO_3$ (3N aq. solution, 93.0 µL, 0.30 mmol). The mixture is degassed with argon and Pd(dppf)$Cl_2$.DCM (6.00 mg, 0.01 mmol) is added. The reaction is heated to 110° C. and stirred overnight, then cooled and the mixture is passed through a SPE Thiol cartridge. The solution is concentrated and purified by HPLC-MS (using a solvent gradient $H_2O$/ACN with $NH_4OH$) to afford 17 mg of Example 34. ESI pos.+neg. (Loop-Inj.): 434 [M+H]$^+$; HPLC (Rt): 1.03 min (Method F).

Example 69

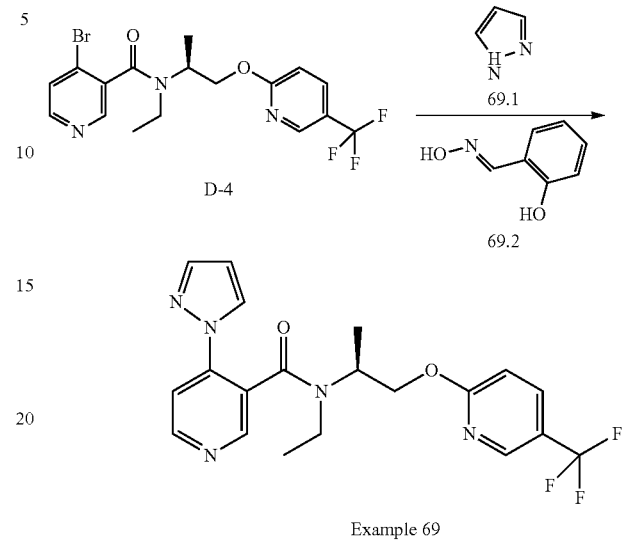

Example 69

To a solution of D-4 (43.0 mg, 0.10 mmol) and 69.1 (17 mg, 0.25 mmol) in dry ACN (2.0 mL), $Cs_2CO_3$ (65.0 mg, 0.20 mmol) is added. The mixture is degassed with argon and $Cu_2O$ (3.00 mg, 0.02 mmol) and 69.2 (11.0 mg, 0.08 mmol) are added. The reaction is heated to 80° C. and stirred for 5 days. After cooling, the reaction is diluted with MeOH, passed through a SPE Thiol cartridge and directly purified by prep. HPLC-MS (using a solvent gradient $H_2O$/ACN with $NH_4OH$). Fractions are then lyophilized to afford 12 mg of Example 69. ESI pos.+neg. (Loop-Inj.): 420 [M+H]$^+$; HPLC (Rt): 1.04 min (Method F).

The following examples are prepared in analogy to the above described procedure using the corresponding amide (see Amide Intermediates) as described before.

| Amide | Structure | ESI pos. + neg. (Loop-Inj.) | HPLC (Rt) [min] | HPLC method |
|---|---|---|---|---|
| 24 | 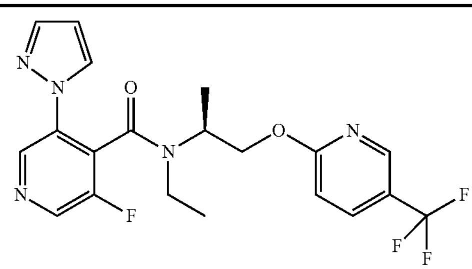 | 438 | 1.12 | F |
| 64 | 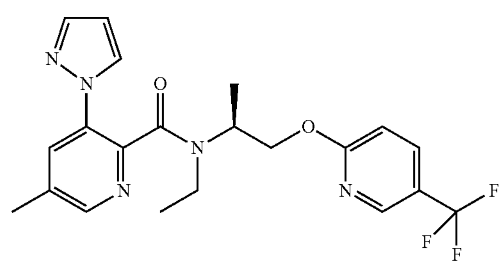 [SMILES: CCN(C(=O)c1ncc(C)cc1-n1cccn1)[C@@H](C)COc1ccc(C(F)(F)F)cn1] | 434 | 1.09 | F |

| Amide | Structure | ESI pos. + neg. (Loop-Inj.) | HPLC (Rt) [min] | HPLC method |
|---|---|---|---|---|
| 40 | 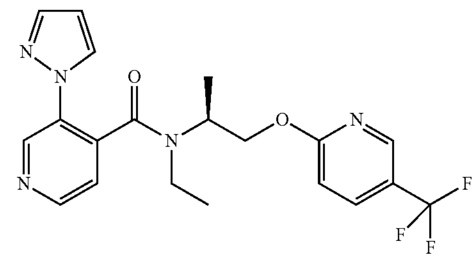 [SMILES: CCN(C(=O)c1ccncc1-n1cccn1)[C@@H](C)COc1ccc(C(F)(F)F)cn1] | 420 | 1.01 | F |

Example 60

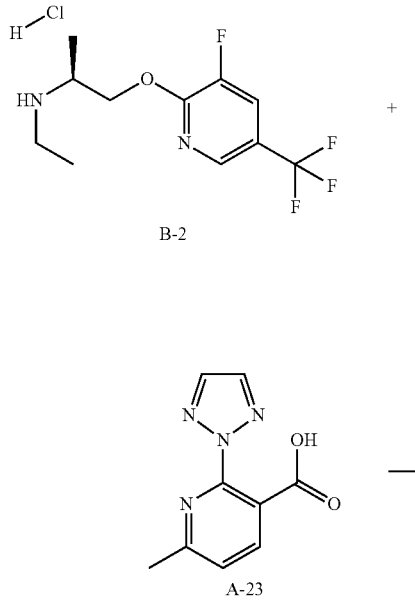

To a mixture of A-23 (40.0 mg, 0.20 mmol) in dry DMF (2.0 mL) is added under a nitrogen atmosphere HATU (82.0 mg, 0.22 mmol) and DIPEA (101 μL, 0.60 mmol) and the mixture is stirred for 10 min at RT. B-2 (85.0 mg, 0.20 mmol) is added and the mixture is stirred overnight and then directly purified by preparative HPLC-MS (using a solvent gradient H₂O/ACN with NH₄OH) to afford 61 mg of Example 60. ESI-MS: 475 [M+Na]⁺; HPLC (Rt): 3.47 min (Method R).

The following examples are prepared in analogy to the above described procedure using the corresponding acid (see Acid Intermediates) and amine (see Amine Intermediates) as described before, adjusting the reaction times 5 h for Example 56.

For the synthesis of Examples 54 the work-up is done as follows: the reaction mixture is concentrated, DCM is added and the organic phase is washed with water then dried and concentrated. The crude is purified by HPLC-MS.

| Example | Structure | ESI-MS [M + H]⁺ | HPLC (Rt) [min] | HPLC method |
|---|---|---|---|---|
| 44 | 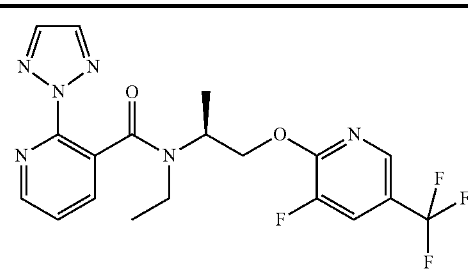 | 461 [M + Na]⁺ | 3.35 | R |

-continued
| Example | Structure | ESI-MS [M + H]+ | HPLC (Rt) [min] | HPLC method |
|---|---|---|---|---|
| 59 | 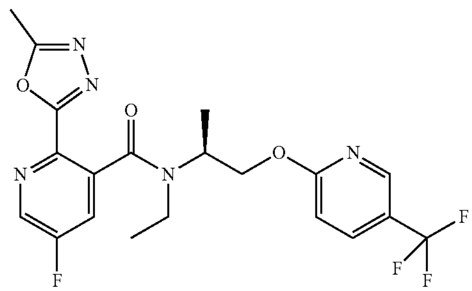 [SMILES: CCN(C(=O)c1cc(F)cnc1-c1nnc(C)o1)[C@@H](C)COc1ccc(C(F)(F)F)cn1] | 476 [M + Na]+ | 3.36 | R |
| 54 | 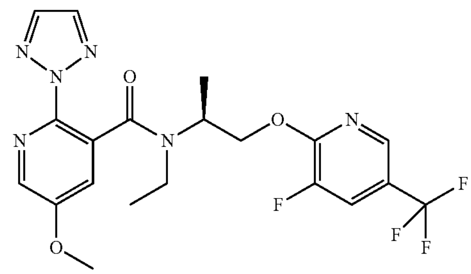 [SMILES: CCN(C(=O)c1cc(OC)cnc1-n1nccn1)[C@@H](C)COc1ncc(C(F)(F)F)cc1F] | 491 [M + Na]+ | 3.51 | R |
| 43 | 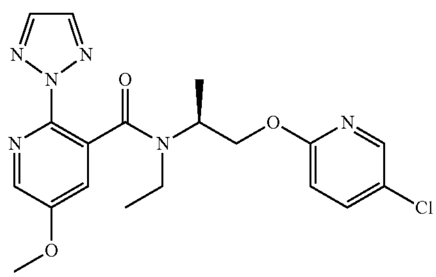 [SMILES: CCN(C(=O)c1cc(OC)cnc1-n1nccn1)[C@@H](C)COc1ccc(Cl)cn1] | 439 [M + Na]+ | 3.33 | R |
| 56 | 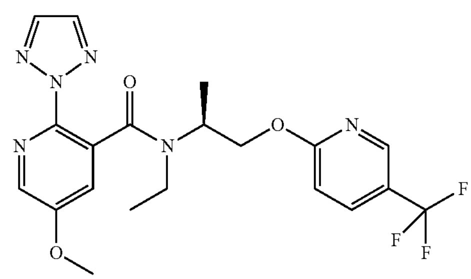 [SMILES: CCN(C(=O)c1cc(OC)cnc1-n1nccn1)[C@@H](C)COc1ccc(C(F)(F)F)cn1] | 473 [M + Na]+ | 3.44 | R |
Alternative Route for Example 56
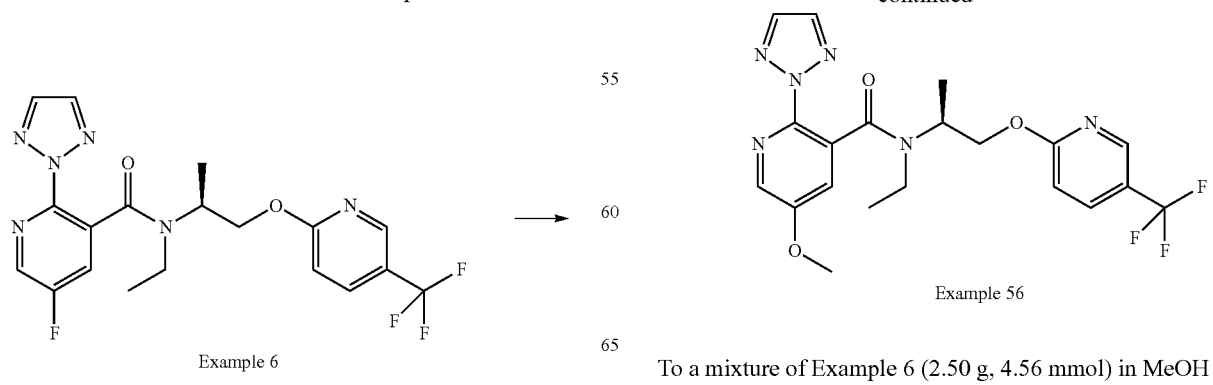
Example 6
Example 56
To a mixture of Example 6 (2.50 g, 4.56 mmol) in MeOH (12 mL) is added NaOMe (6.16 mL, 22.8 mmol) and the mixture is heated at reflux for 1 h. The solvent is evaporated, water is added and it is extracted with DCM. The organic phase is dried and concentrated. The crude is purified by flash column chromatography on silica gel (using a solvent gradient from cyclohexane/EA 88/12 to 100% EA) to afford 1.2 g of Example 56. ESI-MS: 451 [M+H]$^+$; HPLC (Rt): 3.45 min (Method B).

Example 70

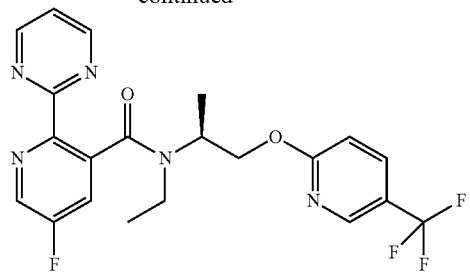

Example 70

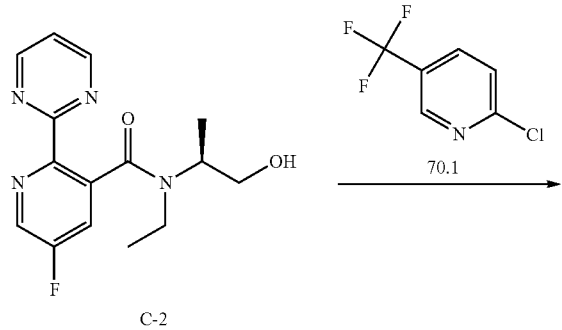

To a mixture of C-2 (45.0 mg, 0.15 mmol) in dry DMF (2.0 mL) under a nitrogen atmosphere and at 5° C. is added NaH (6.0. mg, 0.15 mmol) and the mixture is stirred at this temperature for 30 min. 70.1 (30.0 mg, 0.17 mmol) is then added and the mixture is stirred at 5° C. for 2 h. Water is added to the reaction and the product is extracted with EA. The organic layer is separated, dried and concentrated. The crude product is purified by flash column chromatography on silica gel (using the eluent DCM/MeOH=97/3) to afford 20 mg of Example 70. ESI-MS: 472 [M+Na]$^+$; HPLC (Rt): 3.33 min (Method R).

The following examples are prepared in analogy to the above described procedure using the corresponding alcohol (see Alcohol Intermediates) as described before and the corresponding aryl halide.

| Example | Structure | ESI-MS [M + H]$^+$ | HPLC (Rt) [min] | HPLC method |
|---|---|---|---|---|
| 35 | 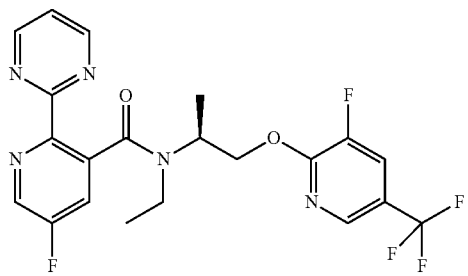 [SMILES: CCN(C(=O)c1cc(F)cnc1-c1ncccn1)[C@@H](C)COc1ncc(C(F)(F)F)cc1F] | 468 | 3.43 | R |
| 45 | 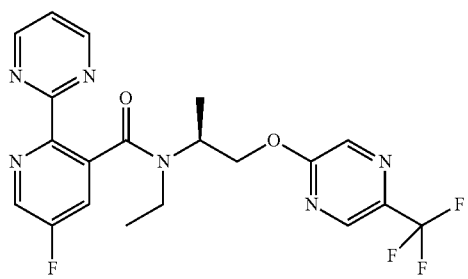 [SMILES: CCN(C(=O)c1cc(F)cnc1-c1ncccn1)[C@@H](C)COc1cnc(C(F)(F)F)cn1] | 451 | 3.18 | R |

Example 71

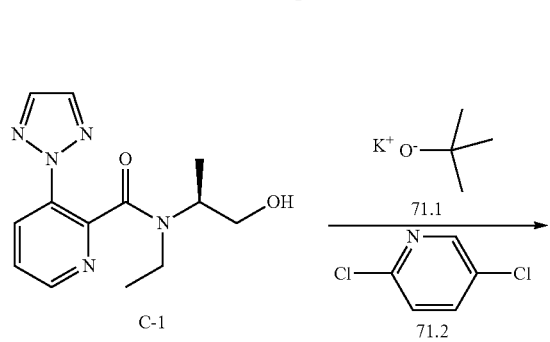

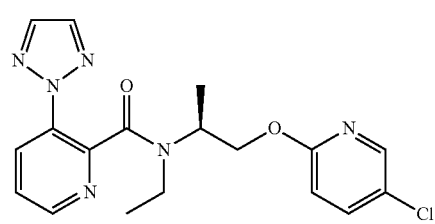

Example 71

To a mixture of C-1 (100 mg, 0.36 mmol) and 71.2 (65.0 mg, 0.44 mmol) in dry DMSO (2.0 mL) is added under a nitrogen atmosphere 71.1 (49.0 mg, 0.44 mmol) and the mixture is stirred at RT for 3 h. Water is added to the reaction and the product is extracted with EA. The organic layer is separated, dried and concentrated. The crude product is purified by flash column chromatography on silica gel (using a solvent gradient n-hexane/EA from 8/2 to 1/1) to afford 64 mg of Example 71. ESI-MS: 409 [M+Na]$^+$; HPLC (Rt): 3.36 min (Method R).

The invention claimed is:

1. A compound of formula I:

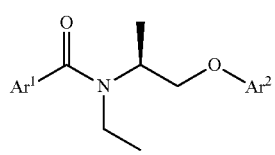

I wherein:

Ar$^1$ represents:

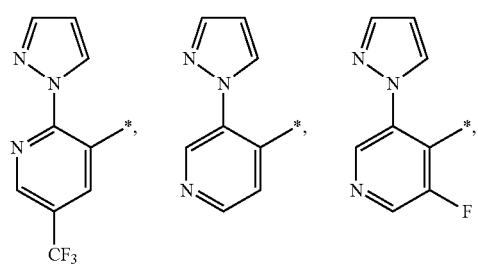

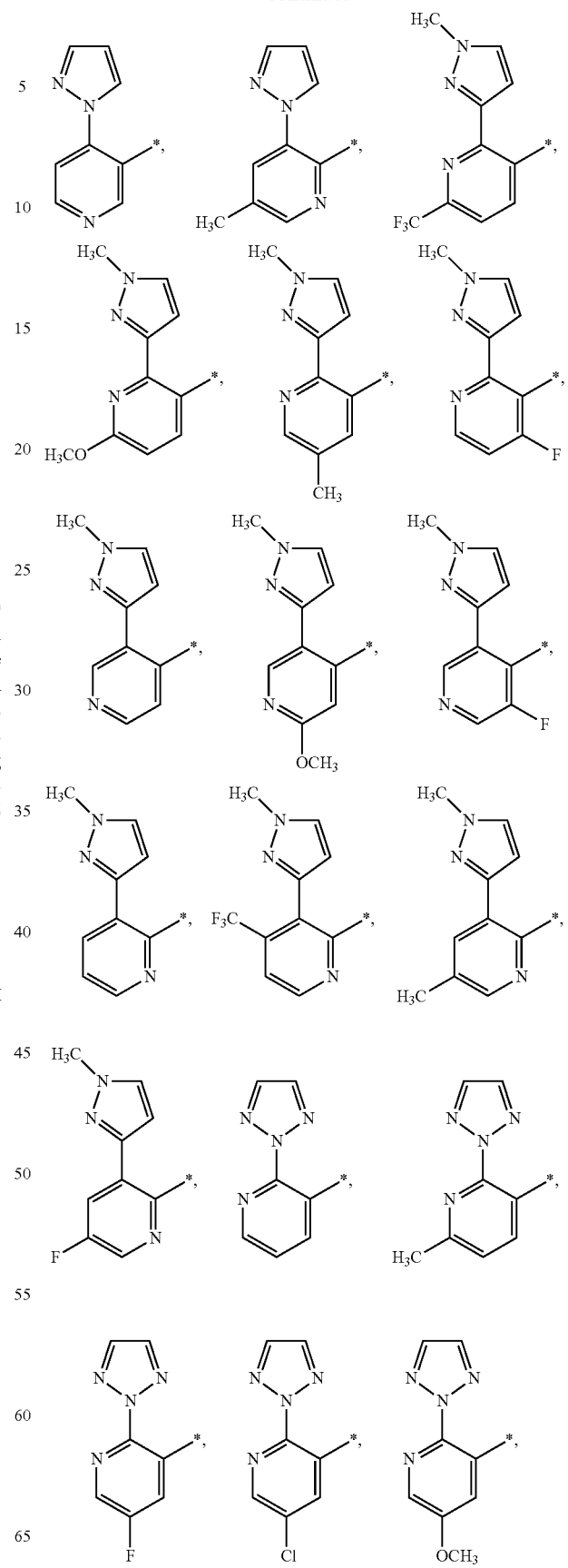

107

-continued

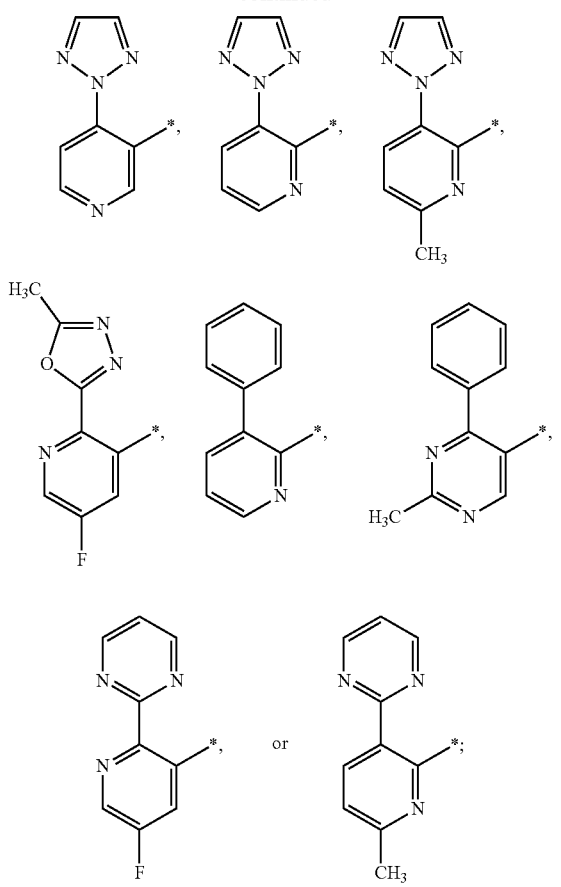

Ar² represents:

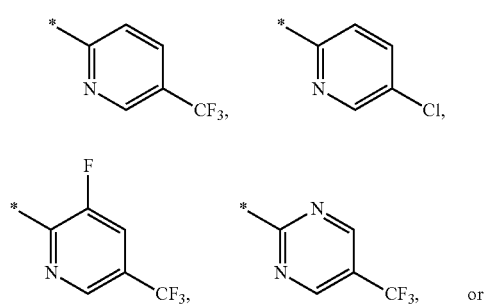

and

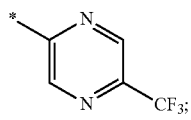

\* represents independently the point of attachment of Ar¹ to the carbonyl group and Ar² to the oxygen atom;

or a pharmaceutically acceptable salt thereof.

2. The compound according to claim 1, or a pharmaceutically acceptable salt thereof, wherein Ar¹ represents:

108

3. The compound according to claim 1, or a pharmaceutically acceptable salt thereof, wherein Ar¹ represents:

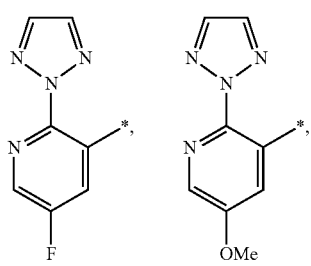

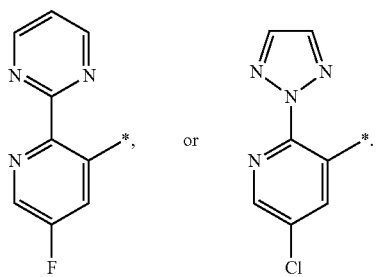
4. The compound according to claim 1, or a pharmaceutically acceptable salt thereof, wherein $Ar^2$ represents:
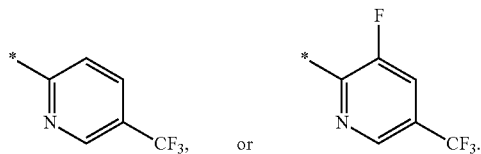 [SMILES: *c1ccc(C(F)(F)F)cn1 ; *c1ncc(C(F)(F)F)cc1F ; "or"]
5. The compound according to claim 1, wherein the compound is selected from the group consisting of:
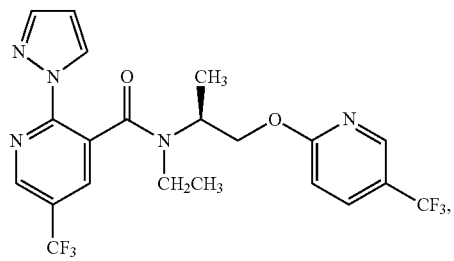
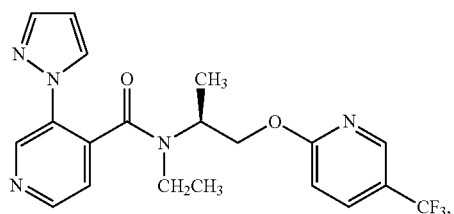
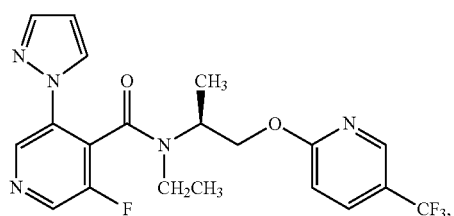
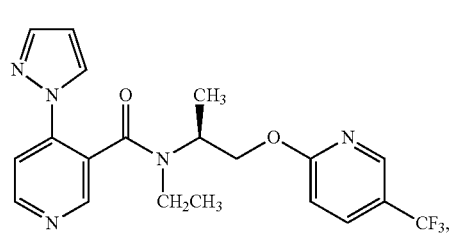
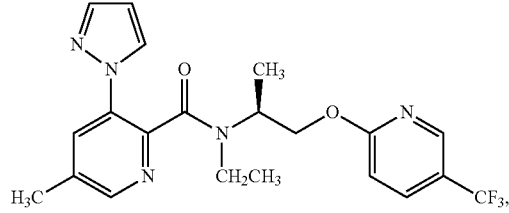
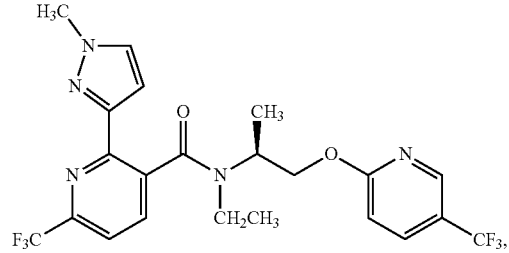
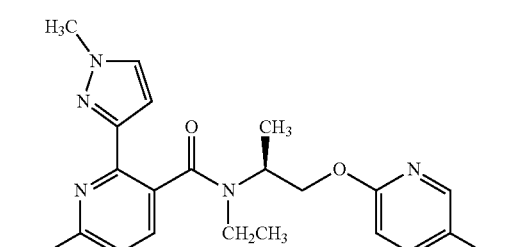
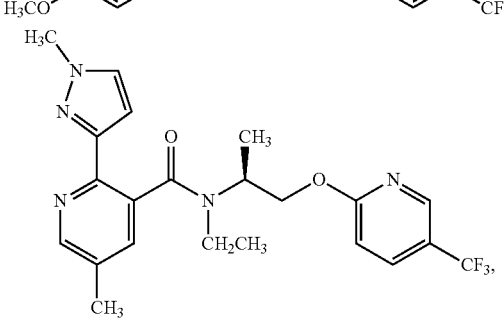
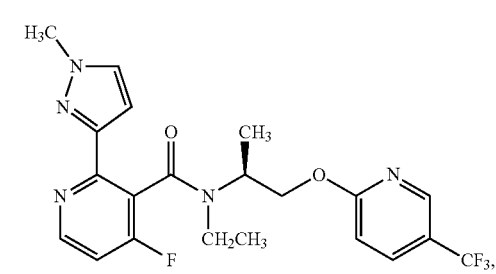
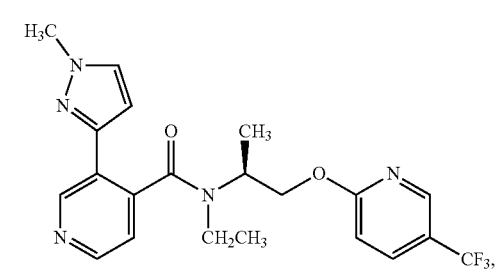

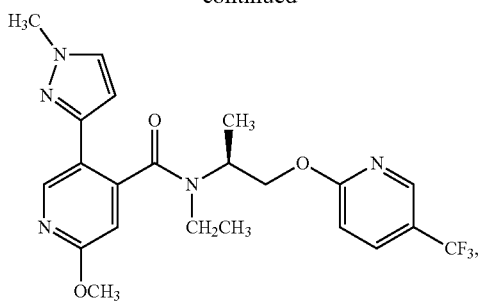
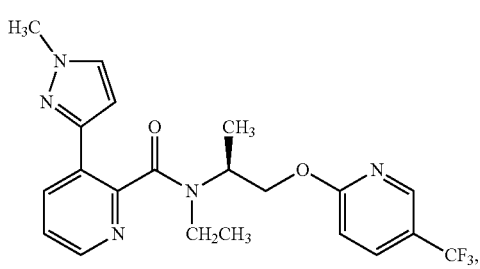
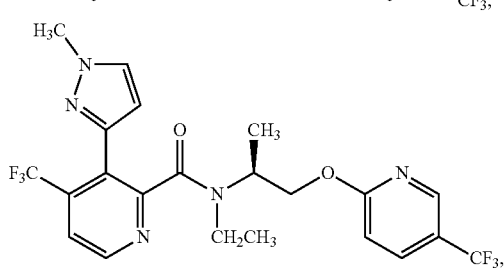
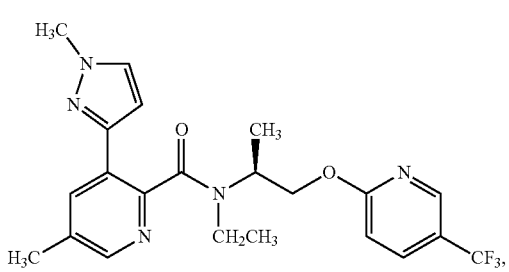
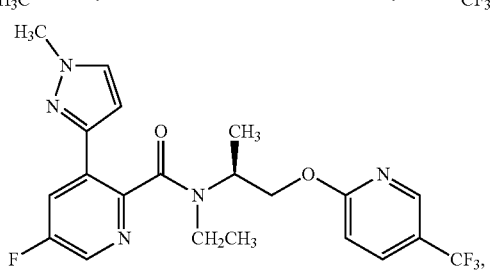
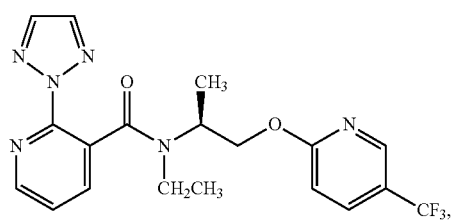
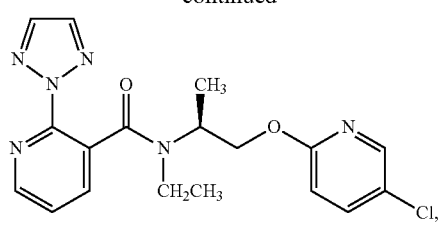
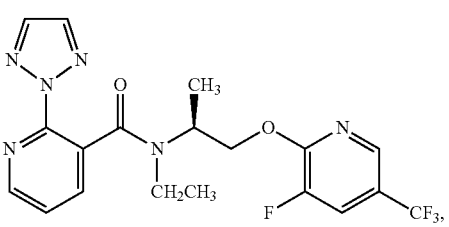
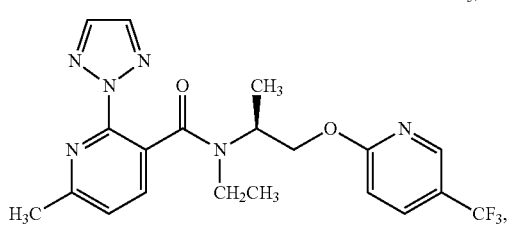
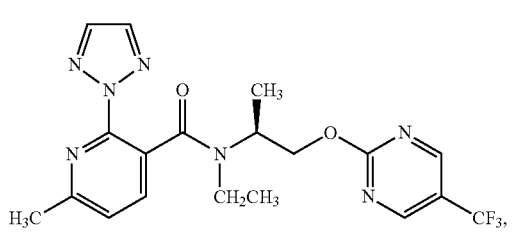
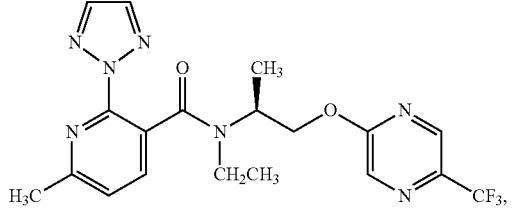
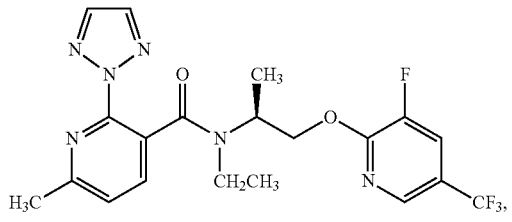
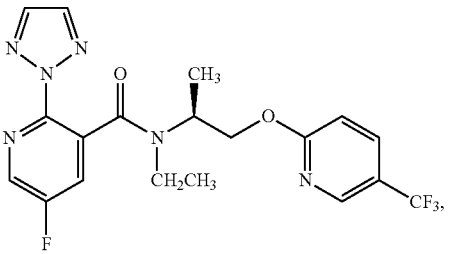

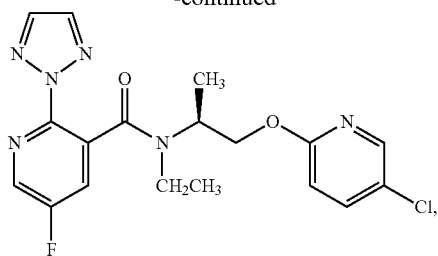
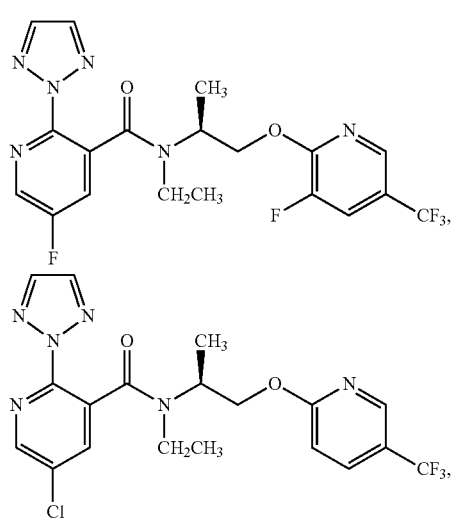
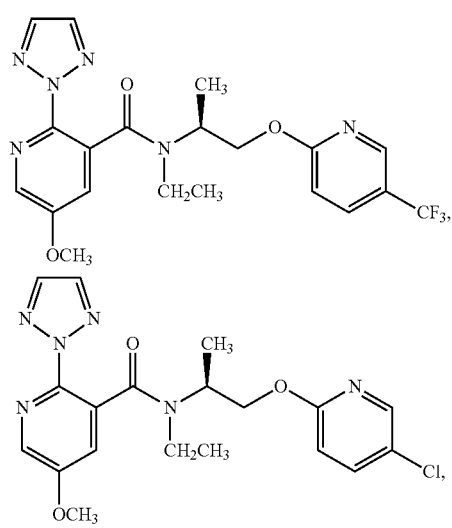
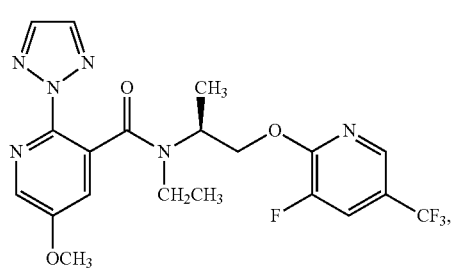
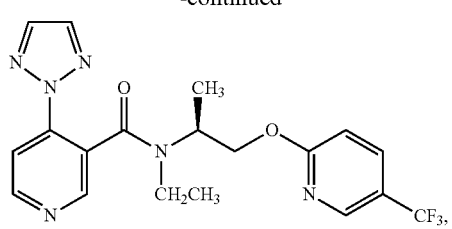
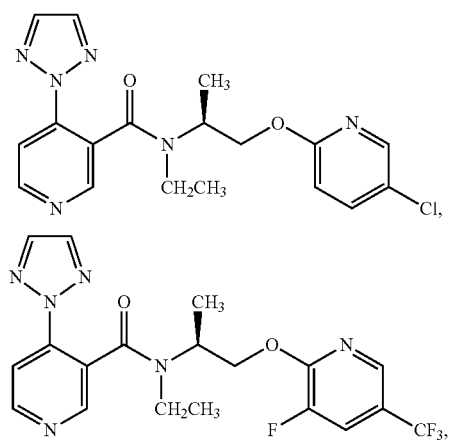
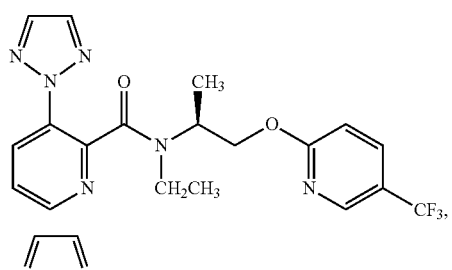
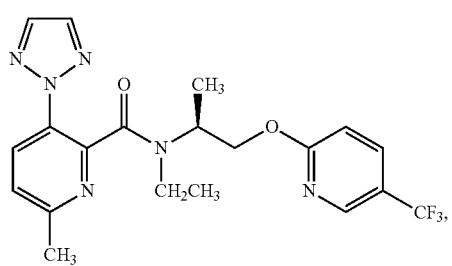

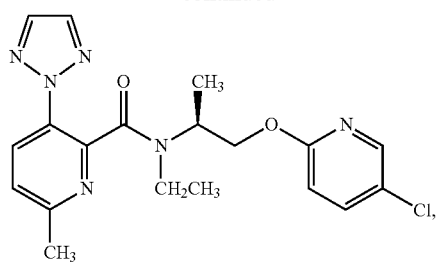
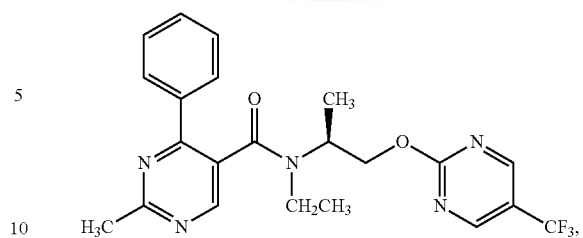
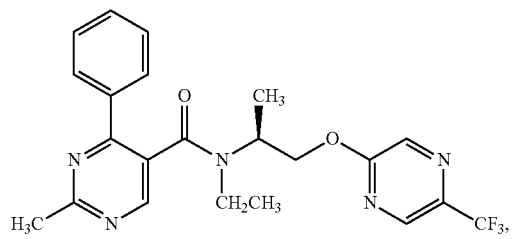
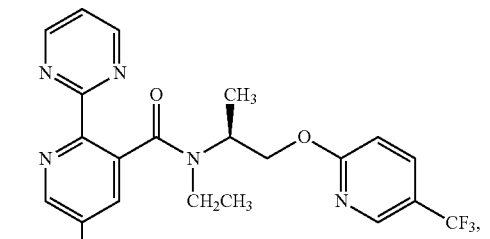
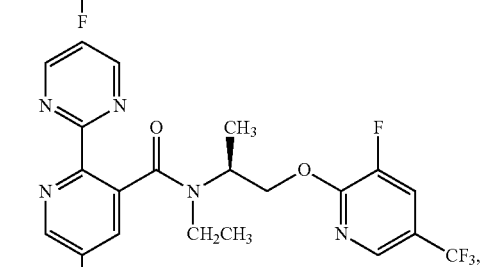
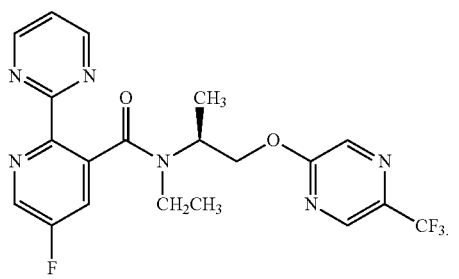
6. A pharmaceutically acceptable salt of the compound according to claim 1, wherein the compound is selected from the group consisting of:

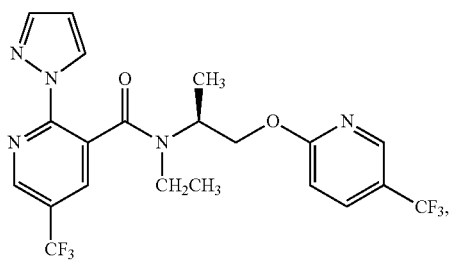
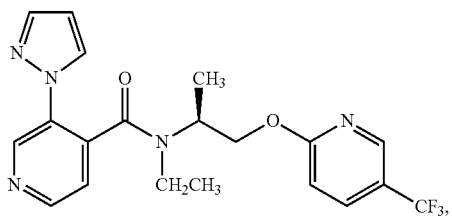
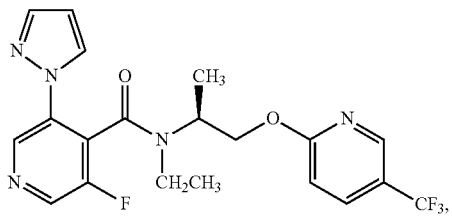
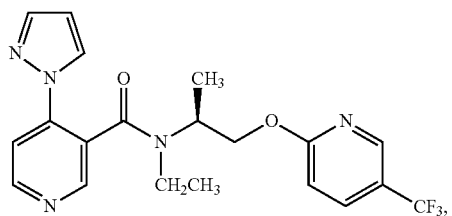
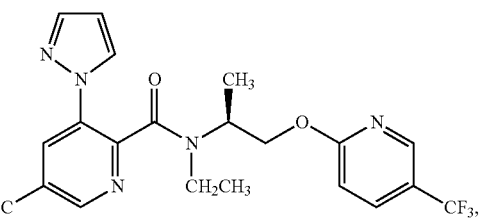
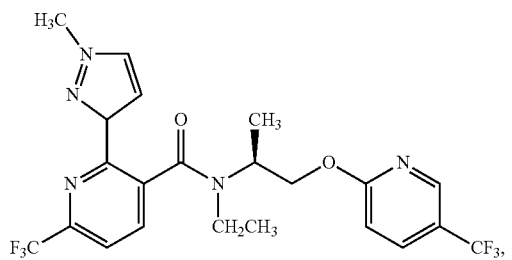
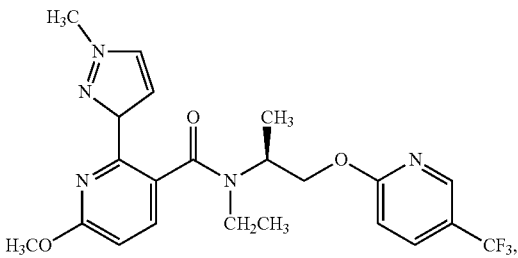
-continued
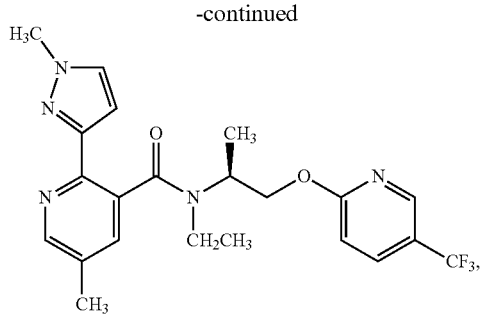
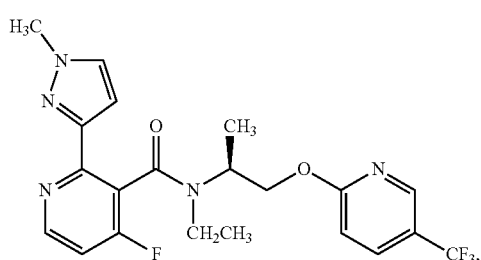
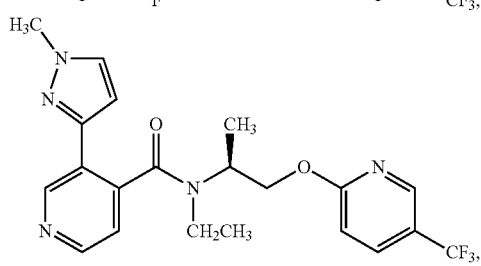
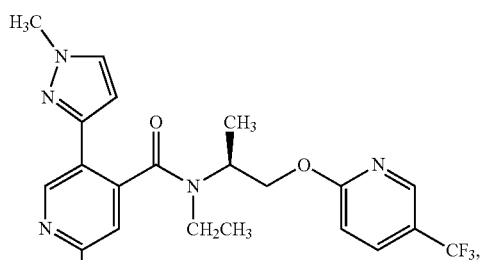
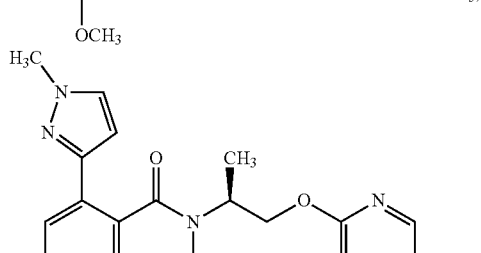
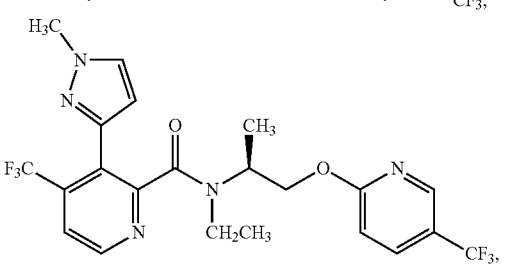

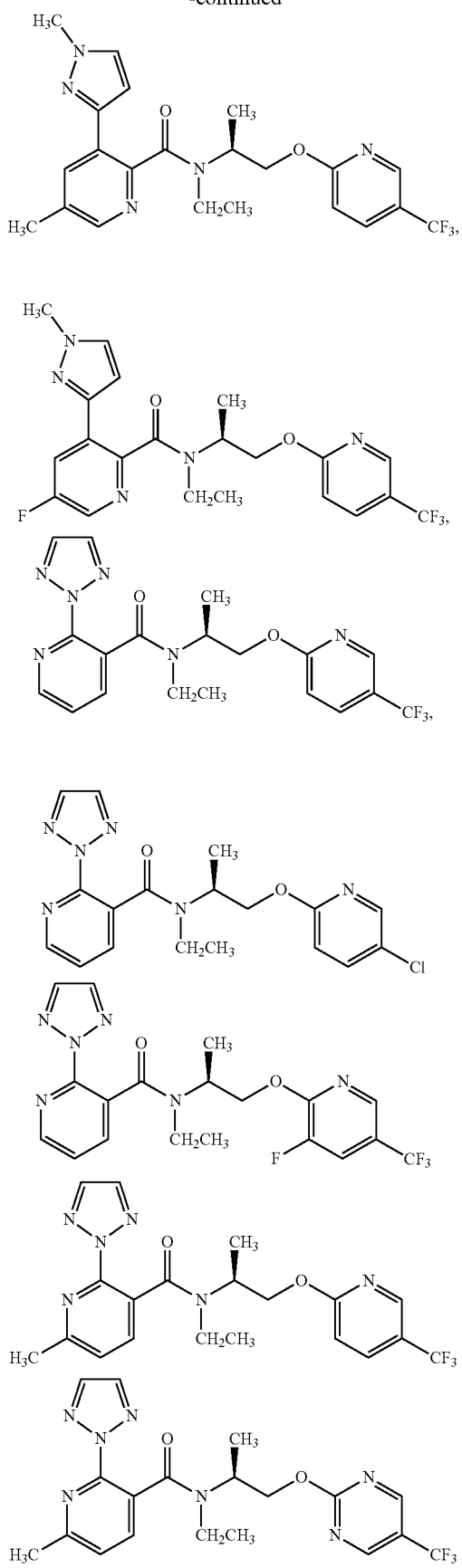
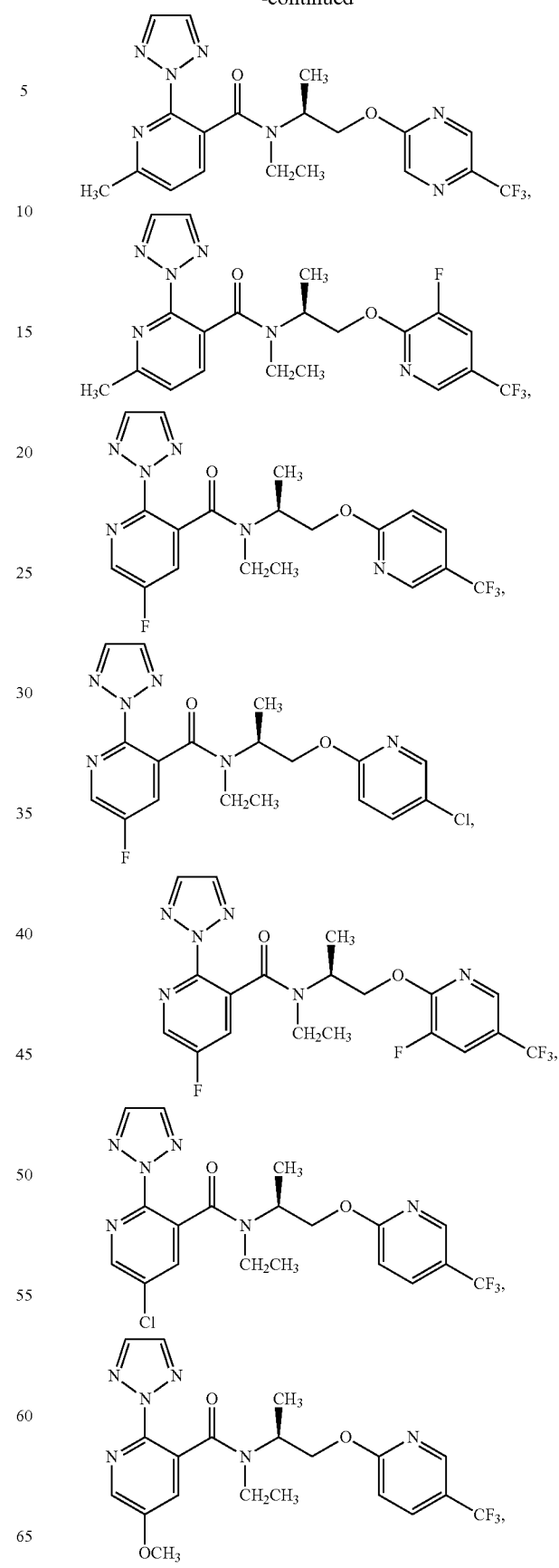

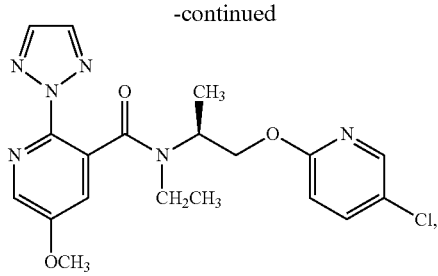
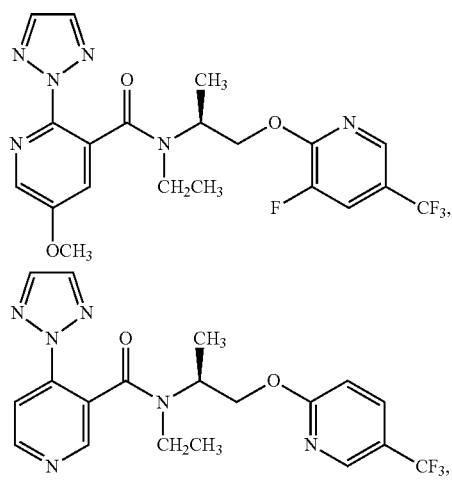
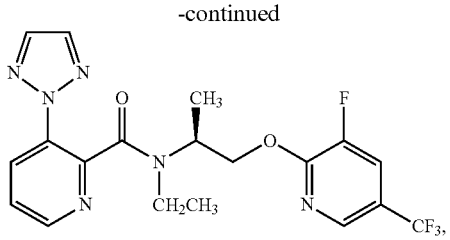
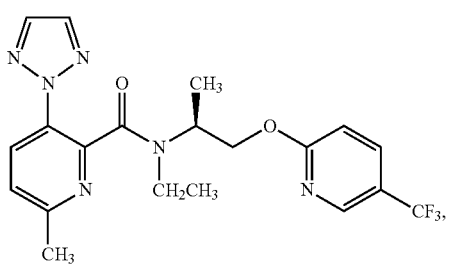
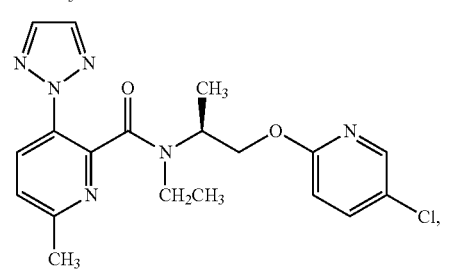
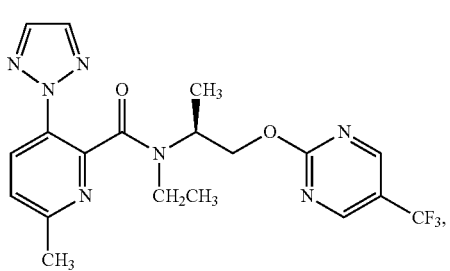
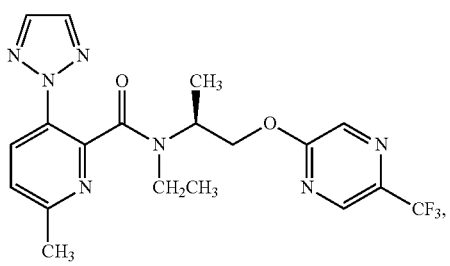
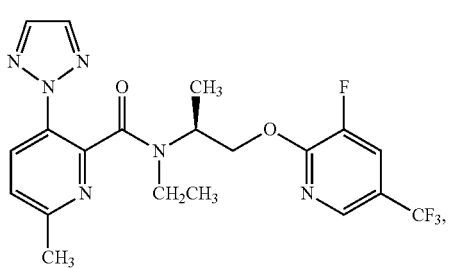

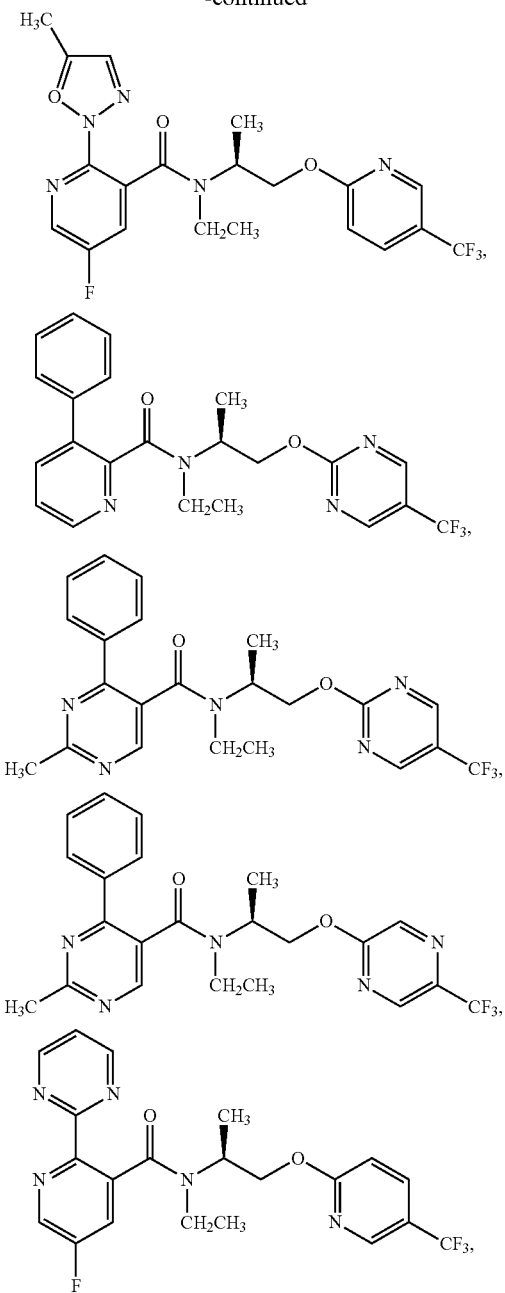

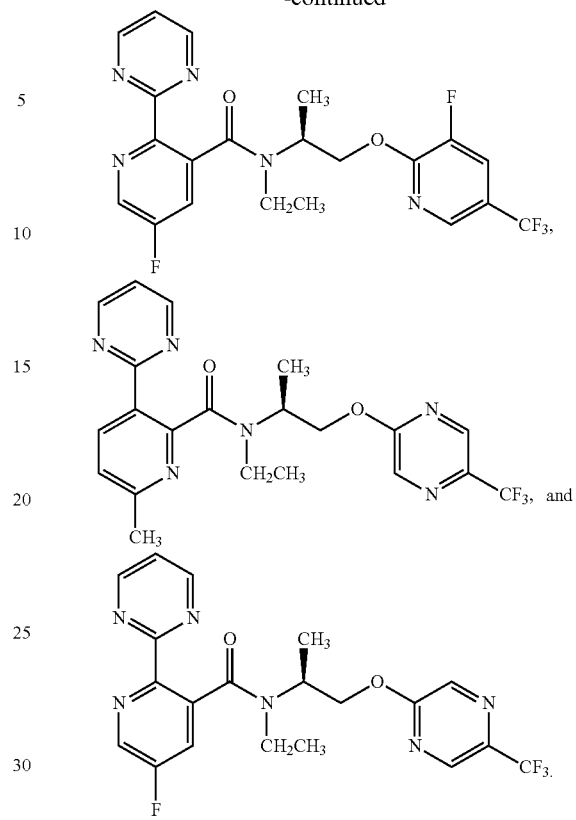

7. A pharmaceutical composition comprising a compound according to claim 1, or a pharmaceutically acceptable salt thereof, in admixture with a pharmaceutically acceptable adjuvant, diluent and/or carrier.

8. A method for antagonizing orexin type 1 receptor activity in a patient, comprising administering to a patient in need thereof a therapeutically effective amount of a compound according to claim 1, or a pharmaceutically acceptable salt thereof.

9. The method according to claim 8, wherein the patient has a psychiatric or neurological condition associated with impulse control deficit selected from the group consisting of an anxiety disorder, an attention disorder, a conduct disorder, an eating disorder, an impulse control disorder, a mood disorder, a neurodegenerative disorder, a personality disorder, a psychosexual disorder, a sexual disorder, a sleep disorder, a neurological disease, and a drug addiction.

* * * * *